(12) United States Patent
Berme et al.

(10) Patent No.: US 12,158,382 B1
(45) Date of Patent: Dec. 3, 2024

(54) FORCE MEASUREMENT SYSTEM

(71) Applicant: Bertec Corporation, Columbus, OH (US)

(72) Inventors: Necip Berme, Worthington, OH (US); Sasan Ghassab, Worthington, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/395,672

(22) Filed: Dec. 25, 2023

Related U.S. Application Data

(63) Continuation-in-part of application No. 18/120,941, filed on Mar. 13, 2023, now Pat. No. 11,850,078,
(Continued)

(51) Int. Cl.
*G01L 1/22* (2006.01)
*G01G 3/14* (2006.01)
(Continued)

(52) U.S. Cl.
CPC .......... *G01L 1/2243* (2013.01); *G01G 3/1402* (2013.01); *G01G 21/23* (2013.01);
(Continued)

(58) Field of Classification Search
CPC .... G01G 3/1402; G01G 3/1412; G01G 21/23; G01L 1/2206; G01L 1/2243; G01L 1/225; G01L 1/2287; G01L 1/26; G01L 5/1627
See application file for complete search history.

(56) References Cited

U.S. PATENT DOCUMENTS 3,693,425 A    9/1972  Starita et al.
3,927,560 A   12/1975  Farr
(Continued)

FOREIGN PATENT DOCUMENTS

CN    201302482 Y    9/2009
CN    201935729 U    8/2011
(Continued)

OTHER PUBLICATIONS

First office action on the merits (Non-Final Rejection) in U.S. Appl. No. 14/158,809, mailed on Jul. 18, 2014.
(Continued)

*Primary Examiner* — Randy W Gibson
(74) *Attorney, Agent, or Firm* — The Law Office of Patrick F. O'Reilly III, LLC

(57) ABSTRACT

A force measurement system is disclosed herein. The force measurement system includes a force measurement assembly including at least one load transducer and a data processing device. The at least one load transducer including a load transducer frame portion, the load transducer frame portion including a first transducer beam section and a second transducer beam section, the first transducer beam section being connected to a middle portion of the second transducer beam section, and one or more deformation sensing elements are disposed on the load transducer frame portion. The data processing device is operatively coupled to the one or more deformation sensing elements of the at least one load transducer, the data processing device is configured to receive the first output signals from the one or more deformation sensing elements of the at least one load transducer, and to determine a first output force from the first output signal.

20 Claims, 32 Drawing Sheets

Related U.S. Application Data which is a continuation-in-part of application No. 17/682,652, filed on Feb. 28, 2022, now Pat. No. 11,604,106, which is a continuation-in-part of application No. 17/367,599, filed on Jul. 5, 2021, now Pat. No. 11,262,258, which is a continuation-in-part of application No. 17/013,812, filed on Sep. 7, 2020, now Pat. No. 11,054,325, which is a continuation-in-part of application No. 16/735,411, filed on Jan. 6, 2020, now Pat. No. 10,765,936.

(60) Provisional application No. 62/957,178, filed on Jan. 4, 2020.

(51) Int. Cl.
*G01G 21/23* (2006.01)
*G01L 1/26* (2006.01)
*G01L 5/1627* (2020.01)

(52) U.S. Cl.
CPC ............ *G01L 1/2206* (2013.01); *G01L 1/225* (2013.01); *G01L 1/2287* (2013.01); *G01L 1/26* (2013.01); *G01L 5/1627* (2020.01)

(56) References Cited

U.S. PATENT DOCUMENTS

| | | | |
|---|---|---|---|
| 3,939,704 A | 2/1976 | Zipin | |
| 3,948,093 A | 4/1976 | Folchi et al. | |
| 4,223,752 A * | 9/1980 | Belcher | G01G 21/23 177/255 |
| 4,420,985 A | 12/1983 | Raskin | |
| 4,448,083 A | 5/1984 | Hayashi | |
| 4,542,800 A * | 9/1985 | Knothe | G01G 3/1412 73/862.633 |
| 4,573,362 A | 3/1986 | Amlani | |
| 4,674,339 A | 6/1987 | Hatamura et al. | |
| 4,686,440 A | 8/1987 | Hatamura et al. | |
| 4,775,018 A * | 10/1988 | Kroll | G01G 3/1402 177/211 |
| 4,880,069 A * | 11/1989 | Bradley | G01G 21/23 177/229 |
| 4,886,133 A * | 12/1989 | Horn | G01G 21/22 177/229 |
| 4,924,708 A | 5/1990 | Solomon et al. | |
| 4,964,211 A | 10/1990 | Arao et al. | |
| 4,993,506 A | 2/1991 | Angel | |
| 5,083,466 A | 1/1992 | Holm-Kennedy et al. | |
| 5,166,571 A | 11/1992 | Konno et al. | |
| 5,166,892 A | 11/1992 | Inoue et al. | |
| 5,183,125 A * | 2/1993 | Schurr | G01L 1/2243 177/229 |
| 5,400,661 A | 3/1995 | Cook et al. | |
| 5,510,581 A | 4/1996 | Angel | |
| 5,512,713 A | 4/1996 | Naito et al. | |
| 5,814,740 A | 9/1998 | Cook et al. | |
| 5,844,488 A | 12/1998 | Musick | |
| 5,889,208 A | 3/1999 | Nose | |
| 5,889,214 A | 3/1999 | Kang et al. | |
| 5,929,391 A * | 7/1999 | Petrucelli | G01G 3/13 177/229 |
| 5,969,268 A | 10/1999 | Sommerfeld et al. | |
| 5,987,982 A | 11/1999 | Wenman et al. | |
| 6,038,488 A | 3/2000 | Barnes et al. | |
| 6,038,933 A | 3/2000 | Meyer | |
| 6,089,106 A | 7/2000 | Patel et al. | |
| 6,113,237 A | 9/2000 | Ober et al. | |
| 6,152,564 A | 11/2000 | Ober et al. | |
| 6,295,878 B1 | 10/2001 | Berme | |
| 6,307,165 B1 * | 10/2001 | Komoto | G01G 3/1412 177/229 |
| 6,323,840 B1 | 11/2001 | Steinbrunner | |
| 6,324,919 B1 | 12/2001 | Larsen et al. | |
| 6,353,431 B1 | 3/2002 | Poole et al. | |
| 6,354,155 B1 | 3/2002 | Berme | |
| 6,389,883 B1 | 5/2002 | Berme et al. | |
| 6,402,635 B1 * | 6/2002 | Nesbit | A63B 69/3667 73/488 |
| 6,422,096 B1 | 7/2002 | Bulat | |
| 6,497,430 B1 | 12/2002 | Odom et al. | |
| 6,609,054 B2 | 8/2003 | Wallace | |
| 6,871,552 B2 | 3/2005 | Liu et al. | |
| 6,936,016 B2 | 8/2005 | Berme et al. | |
| 7,091,428 B2 * | 8/2006 | Ikeshima | G01G 3/1412 73/1.13 |
| 7,204,010 B2 | 4/2007 | Germanton | |
| 7,743,672 B2 | 6/2010 | Kurtz et al. | |
| 7,825,814 B2 | 11/2010 | Lokhorst et al. | |
| 8,181,541 B2 | 5/2012 | Berme | |
| 8,186,232 B2 | 5/2012 | McDearmon et al. | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,533,879 B1 | 9/2013 | Taylor | |
| 8,543,540 B1 | 9/2013 | Wilson et al. | |
| 8,544,347 B1 | 10/2013 | Berme | |
| 8,574,080 B2 | 11/2013 | Yamazaki et al. | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,746,085 B2 | 6/2014 | Singh et al. | |
| 8,749,501 B2 | 6/2014 | Oda et al. | |
| 8,764,532 B1 | 7/2014 | Berme | |
| 8,766,925 B2 | 7/2014 | Perlin et al. | |
| 8,844,377 B2 | 9/2014 | Yap | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 8,943,902 B2 | 2/2015 | Bosscher et al. | |
| 9,032,817 B2 * | 5/2015 | Berme | G01L 5/1627 73/862.045 |
| 9,186,091 B2 | 11/2015 | Mainini et al. | |
| 9,404,823 B1 | 8/2016 | Berme et al. | |
| 9,448,128 B2 | 9/2016 | Kim et al. | |
| 9,778,119 B2 | 10/2017 | Berme et al. | |
| 9,829,311 B1 | 11/2017 | Wilson et al. | |
| 10,085,676 B1 | 10/2018 | Berme et al. | |
| 10,126,186 B2 | 11/2018 | Berme et al. | |
| 10,216,262 B1 | 2/2019 | Berme et al. | |
| 10,222,279 B1 | 3/2019 | Legrand, III et al. | |
| 10,231,662 B1 | 3/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 7/2021 | Akbas et al. | |
| 11,158,422 B1 | 8/2021 | Berme et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |

(56) References Cited

U.S. PATENT DOCUMENTS

| | | |
|---|---|---|
| 11,348,279 B1 | 5/2022 | Akbas et al. |
| 11,392,236 B2 | 7/2022 | Jung |
| 11,393,773 B1 | 7/2022 | Bui et al. |
| 11,458,362 B1 | 10/2022 | Berme et al. |
| 11,521,373 B1 | 12/2022 | Akbas et al. |
| 11,540,744 B1 | 1/2023 | Berme |
| 11,604,106 B2 | 3/2023 | Berme et al. |
| 11,631,193 B1 | 4/2023 | Akbas et al. |
| 11,688,139 B1 | 6/2023 | Karagoz et al. |
| 11,705,244 B1 | 7/2023 | Berme |
| 11,712,162 B1 | 8/2023 | Berme et al. |
| 11,790,536 B1 | 10/2023 | Berme et al. |
| 11,798,182 B1 | 10/2023 | Karagoz et al. |
| 11,816,258 B1 | 11/2023 | Berme et al. |
| 11,826,601 B1 | 11/2023 | Berme |
| 11,850,078 B1 | 12/2023 | Berme |
| 11,857,331 B1 | 1/2024 | Berme et al. |
| 11,865,407 B1 | 1/2024 | Berme et al. |
| 2003/0216656 A1 | 11/2003 | Berme et al. |
| 2006/0038516 A1 | 2/2006 | Burse |
| 2006/0081072 A1 | 4/2006 | Park |
| 2007/0064066 A1 | 3/2007 | Piatt et al. |
| 2007/0136017 A1 | 6/2007 | Wang et al. |
| 2007/0205776 A1 | 9/2007 | Harish et al. |
| 2008/0041166 A1 | 2/2008 | Kurtz et al. |
| 2008/0228110 A1 | 9/2008 | Berme |
| 2009/0120208 A1 | 5/2009 | Meyer |
| 2010/0031746 A1 | 2/2010 | Paros et al. |
| 2010/0170349 A1 | 7/2010 | Hatanaka et al. |
| 2011/0107850 A1 | 5/2011 | Kim et al. |
| 2011/0259111 A1 | 10/2011 | Ohsato |
| 2011/0277562 A1 | 11/2011 | Berme |
| 2012/0162122 A1 | 6/2012 | Geaghan |
| 2012/0234104 A1 | 9/2012 | Seibold |
| 2012/0266648 A1 | 10/2012 | Berme et al. |
| 2012/0271565 A1 | 10/2012 | Berme et al. |
| 2013/0086974 A1 | 4/2013 | Rausche |
| 2013/0180343 A1 | 7/2013 | Furniss et al. |
| 2013/0255394 A1 | 10/2013 | Ishii et al. |
| 2013/0291653 A1 | 11/2013 | Kempainen et al. |
| 2015/0096387 A1 | 4/2015 | Berme et al. |
| 2015/0135856 A1 | 5/2015 | Kim et al. |
| 2015/0241291 A1 | 8/2015 | Riou et al. |
| 2016/0139717 A1 | 5/2016 | Filiz et al. |
| 2016/0245711 A1 | 8/2016 | Berme et al. |
| 2016/0313196 A1 | 10/2016 | Seo et al. |
| 2016/0334288 A1 | 11/2016 | Berme et al. |
| 2017/0055851 A1 | 3/2017 | Al-Ali |
| 2017/0363464 A1 | 12/2017 | Shafer et al. |
| 2018/0008168 A1 | 1/2018 | Pearlman et al. |
| 2018/0024015 A1 | 1/2018 | Berme et al. |
| 2019/0060659 A1 | 2/2019 | Ginhoux et al. |
| 2019/0078951 A1 | 3/2019 | Berme et al. |
| 2019/0310142 A1 | 10/2019 | Kim |
| 2020/0139229 A1 | 5/2020 | Berme et al. |
| 2020/0408625 A1 | 12/2020 | Berme et al. |
| 2021/0055179 A1 | 2/2021 | Park et al. |
| 2021/0137398 A1 | 5/2021 | Park et al. |
| 2021/0333163 A1 | 10/2021 | Berme et al. |
| 2022/0178775 A1 | 6/2022 | Berme et al. |

FOREIGN PATENT DOCUMENTS

| | | | |
|---|---|---|---|
| EP | 1707934 A1 | 10/2006 | |
| GB | 2538631 B | 2/2018 | |
| JP | 59094016 A | 5/1984 | |

OTHER PUBLICATIONS

Notice of Allowance in U.S. Appl. No. 14/158,809, mailed on Jan. 21, 2015.

First office action on the merits (Non-Final Rejection) in U.S. Appl. No. 14/714,797, mailed on Feb. 3, 2016.

Notice of Allowance in U.S. Appl. No. 14/714,797, mailed on Mar. 28, 2016.

Search Report from the UK Intellectual Property Office for UK Patent Appl. No. GB1608606.8, dated Jun. 8, 2016.

Examination Report from the UK Intellectual Property Office for UK Patent Appl. No. GB1608606.8, dated May 22, 2017.

First office action on the merits (Non-Final Rejection) in U.S. Appl. No. 15/224,419, mailed on Mar. 29, 2017.

Notice of Allowance in U.S. Appl. No. 15/224,419, mailed on May 19, 2017.

P. Holmberg and A. Nilsson, "The use of an adaptively temperature compensated a.c. bridge circuit for torque measurements—a robotics application", Measurement, vol. 11, issue 1, Mar. 1993, pp. 65-77.

First office action on the merits (Non-Final Rejection) in U.S. Appl. No. 15/721,951, mailed on Apr. 5, 2018.

Notice of Allowance in U.S. Appl. No. 15/721,951, mailed on Jul. 12, 2018.

First office action on the merits (Non-Final Rejection) in U.S. Appl. No. 16/186,512, mailed on Jul. 31, 2019.

Notice of Allowance in U.S. Appl. No. 16/186,512, mailed on Aug. 22, 2019.

Notice of Allowance in U.S. Appl. No. 16/735,411, mailed on May 5, 2020.

First office action on the merits (Non-Final Rejection) in U.S. Appl. No. 17/013,812, mailed on Nov. 17, 2020.

Notice of Allowance in U.S. Appl. No. 17/013,812, mailed on Mar. 1, 2020.

First office action on the merits (Non-Final Rejection) in U.S. Appl. No. 17/367,599, mailed on Aug. 27, 2021.

Notice of Allowance in U.S. Appl. No. 17/367,599, mailed on Oct. 21, 2021.

First office action on the merits (Non-Final Rejection) in U.S. Appl. No. 17/682,652, mailed on Apr. 15, 2022.

Second office action on the merits (Final Rejection) in U.S. Appl. No. 17/682,652, mailed on Jul. 25, 2022.

Notice of Allowance in U.S. Appl. No. 17/682,652, mailed on Nov. 7, 2022.

First office action on the merits (Non-Final Rejection) in U.S. Appl. No. 18/120,941, mailed on May 1, 2023.

Notice of Allowance in U.S. Appl. No. 18/120,941, mailed on Aug. 15, 2023.

\* cited by examiner

Section C-C

Section D-D

Section E-E

FORCE MEASUREMENT SYSTEM

CROSS-REFERENCE TO RELATED APPLICATIONS

This patent application is a continuation-in-part of U.S. Nonprovisional patent application Ser. No. 18/120,941, entitled "Force Measurement System", filed on Mar. 13, 2023; which is a continuation-in-part of U.S. Nonprovisional patent application Ser. No. 17/682,652, entitled "Force Measurement Assembly", filed on Feb. 28, 2022, now U.S. Pat. No. 11,604,106; which is a continuation-in-part of U.S. Nonprovisional patent application Ser. No. 17/367,599, entitled "Force Measurement System", filed on Jul. 5, 2021, now U.S. Pat. No. 11,262,258; which is a continuation-in-part of U.S. Nonprovisional patent application Ser. No. 17/013,812, entitled "Force Measurement System", filed on Sep. 7, 2020, now U.S. Pat. No. 11,054,325; which is a continuation-in-part of U.S. Nonprovisional patent application Ser. No. 16/735,411, entitled "Force Measurement System", filed on Jan. 6, 2020, now U.S. Pat. No. 10,765,936; which claims priority to U.S. Provisional Patent Application No. 62/957,178, entitled "Body Sway Measurement System", filed on Jan. 4, 2020, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a force measurement system. More particularly, the invention relates to a force measurement system having a top component that is supported on a plurality of load transducer beams.

2. Background and Related Art

The use of strain gages in load transducers to measure forces and moments is a known art. A transducer can incorporate one or more load channels. Each load channel measures one of the load components, and is comprised of one or more strain gages mounted to one or more elastic elements that deform under the applied load. An appropriate circuitry relates the resistance change in each set of gages to the applied force or moment. Strain gages have many industrial, medical, and electrical applications due to their small size, low production cost, flexibility in installation and use, and high precision.

When conventional load transducers are utilized in conjunction with force plates, unique load transducers must be designed and fabricated for force plates having a particular footprint size. Consequently, in order to fit force plates with varying footprint sizes, many different custom load transducers are required. These custom load transducers significantly increase the material costs associated with the fabrication of a force plate.

Therefore, what is needed is a load transducer that is capable of being interchangeably used with a myriad of different force plate sizes so that load transducers that are specifically tailored for a particular force plate size are unnecessary. Moreover, there is a need for a universal load transducer that is compact and uses less stock material than conventional load transducers, thereby resulting in lower material costs. Furthermore, there is a need for a force measurement assembly that utilizes the compact and universal load transducer thereon so as to result in a more lightweight and portable force measurement assembly.

In addition, a force measurement system is needed that is capable of assessing the fall risk of a subject based upon a combination of balance parameters. Also, a force measurement system is needed that employs a load transducer beam configuration that is able to be more easily machined. Further, a force measurement system is needed that includes a load transducer that minimizes twisting and has a reduced overall length.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one or more embodiments of the present invention, there is provided a force measurement system that comprises a force measurement assembly including at least one load transducer, the at least one load transducer including a load transducer frame portion, the load transducer frame portion including a first transducer beam section and a second transducer beam section, the first transducer beam section being connected to a middle portion of the second transducer beam section, and the load transducer frame portion configured to receive a load that is applied to the at least one load transducer; and one or more deformation sensing elements disposed on the load transducer frame portion, a first one of the one or more deformation sensing elements being sensitive to a first force component of the load and outputting a first output signal representative of the first force component of the load; and a data processing device operatively coupled to the one or more deformation sensing elements of the at least one load transducer, the data processing device configured to receive the first output signals from the one or more deformation sensing elements of the at least one load transducer, and the data processing device further configured to determine a first output force from the first output signal.

In a further embodiment of the present invention, the first transducer beam section of the load transducer frame portion is disposed generally perpendicular to the second transducer beam section.

In yet a further embodiment, the load transducer frame portion of the at least one load transducer is generally T-shaped; and the first transducer beam section forms the stem portion of the T-shaped load transducer frame portion and the second transducer beam section forms the arm portion of the T-shaped load transducer frame portion.

In still a further embodiment, the one or more deformation sensing elements are disposed on the first transducer beam section of the load transducer frame portion, and the second transducer beam section of the load transducer frame portion contains no deformation sensing elements.

In yet a further embodiment, the one or more deformation sensing elements of the at least one load transducer comprise one or more strain gages configured to measure a deformation of one or more portions of the first transducer beam section of the load transducer frame portion.

In still a further embodiment, the first transducer beam section of the load transducer frame portion comprises at least one first aperture disposed therein, the first transducer beam section having an outer surface and an inner surface, the inner surface circumscribing the at least one first aperture, and the at least one load transducer comprises at least one of the one or more strain gages disposed on the outer surface of the first transducer beam section generally opposite to the inner surface of the at least one first aperture.

In yet a further embodiment, the second transducer beam section of the load transducer frame portion comprises at least one second aperture disposed therein, the at least one second aperture of the second transducer beam section enhancing a measurement sensitivity of the at least one load transducer.

In still a further embodiment, the one or more deformation sensing elements of the at least one load transducer comprise a plurality of deformation sensing elements, a first one of the plurality of deformation sensing elements being sensitive to the first force component of the load and a second one of the plurality of deformation sensing elements being sensitive to a second force component of the load and/or a third force component of the load.

In yet a further embodiment, the first force component of the load comprises a vertical force, the second force component of the load comprises a first shear force in a first direction, and the third force component of the load comprises a second shear force in a second direction that is perpendicular to the first direction of the first shear force.

In still a further embodiment, the at least one load transducer of the force measurement assembly includes a plurality of load transducers spaced apart from one another, and each of the plurality of load transducers includes a load transducer frame portion, the load transducer frame portion including a first transducer beam section and a second transducer beam section, the first transducer beam section being connected to a middle portion of the second transducer beam section, and the load transducer frame portion configured to receive a load that is applied to the load transducer; and a plurality of deformation sensing elements disposed on the load transducer frame portion, a first one of the plurality of deformation sensing elements being sensitive to the first force component of the load and outputting a first output signal representative of the first force component of the load, and a second one of the plurality of deformation sensing elements being sensitive to a second force component of the load and/or a third force component of the load and outputting a second output signal representative of the second force component of the load and/or a third force component of the load. In this further embodiment, the data processing device is operatively coupled to the plurality of deformation sensing elements of the plurality of load transducers, and the data processing device is configured to receive the first and second output signals from the plurality of deformation sensing elements of the plurality of load transducers, and the data processing device is further configured to determine a first output force from the first output signal and a second output force and/or a third output force from the second output signal.

In yet a further embodiment, the first output force comprises a vertical output force, the second output force comprises a first shear output force in a first coordinate axis direction, and the third output force comprises a second shear output force in a second coordinate axis direction that is perpendicular to the first coordinate axis direction of the first shear output force.

In still a further embodiment, each of the plurality of load transducers of the force measurement assembly is diagonally arranged relative to the first coordinate axis direction of the first shear output force and a second coordinate axis direction of the second shear output force such that: (i) when a first shear force in the first coordinate axis direction is applied to the force measurement assembly, a summation of the second output signals from the plurality of deformation sensing elements of the plurality of load transducers by the data processing device produces a first shear force output value above a measurement threshold in the first coordinate axis direction, but generally cancels out in the second coordinate axis direction; and (ii) when a second shear force in the second coordinate axis direction is applied to the force measurement assembly, a summation of the second output signals from the plurality of deformation sensing elements of the plurality of load transducers by the data processing device produces a second shear force output value above a measurement threshold in the second coordinate axis direction, but generally cancels out in the first coordinate axis direction.

In yet a further embodiment, the force measurement assembly further comprises a top component configured to receive at least one portion of a body of a user, the top component being supported by the plurality of load transducers; and the first shear output force in the first coordinate axis direction comprises a shear force in a lateral direction of the user, and the second shear output force in the second coordinate axis direction comprises a shear force in a fore/aft direction of the user.

In still a further embodiment, the force measurement assembly further comprises a top component and a base component, the top component configured to receive at least one portion of a body of a user, the top component being supported on the plurality of load transducers, and the base component being disposed underneath the plurality of load transducers.

In yet a further embodiment, the top component is in a form of a top plate with the top surface for receiving the at least one portion of the body of the user.

In still a further embodiment, the base component is in a form of a bottom plate configured to be disposed on a support surface.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Figure 1:
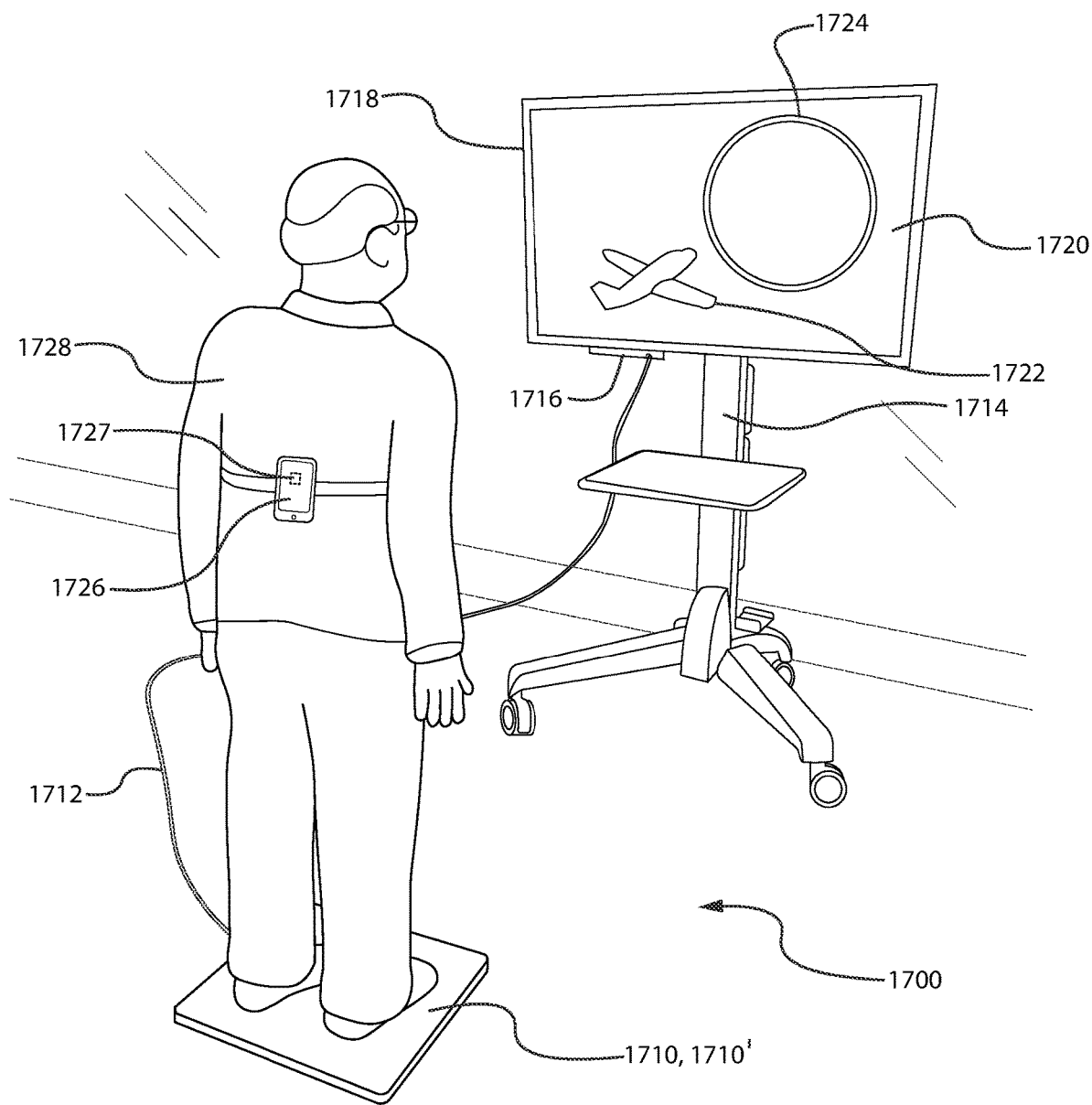
FIG. 1 is a diagrammatic perspective view of a first exemplary force measurement system for measuring the center of pressure and body sway of a subject, according to an embodiment of the invention.

It should be understood that the appended drawings are not necessarily to scale, presenting a somewhat simplified representation of various preferred features illustrative of the basic principles of the invention. The specific design features of the load transducers and the force measurement systems as disclosed herein, including, for example, specific dimensions, orientations, locations, and shapes of the various components, will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the load transducers illustrated in the drawings. In general, up or upward generally refers to an upward direction within the plane of the paper in FIG. 1 and down or downward generally refers to a downward direction within the plane of the paper in FIG. 1.

DETAILED DESCRIPTION OF EMBODIMENTS OF THE INVENTION

It will be apparent to those skilled in the art, that is, to those who have knowledge or experience in this area of technology, that many uses and design variations are possible for the improved load transducers and force measurement systems disclosed herein. The following detailed discussion of various alternative and preferred embodiments will illustrate the general principles of the invention. Other embodiments suitable for other applications will be apparent to those skilled in the art given the benefit of this disclosure.

One or more illustrative embodiments will be described with reference to FIGS. 1-6. In these one or more illustrative embodiments, a force measurement system, which may be in the form of the force measurement system 1700, 1700' depicted in FIGS. 1 and 2 includes a force measurement assembly 1710, 1710' and a data processing device 1716, wherein the data processing device 1716 is configured to determine a center of pressure for the subject 1728 using the output forces and/or moments from the force measurement assembly 1710, 1710'. The center of pressure for the subject 1728 may be computed in the manner described in U.S. Pat. No. 11,262,258, the entire disclosure of which is incorporated herein by reference (e.g., see equations (17) and (18) in U.S. Pat. No. 11,262,258). In these one or more illustrative embodiments, the force measurement system 1700, 1700' further includes an inertial measurement unit 1727 and/or camera 1729 configured to generate output data for determining one or more parameters indicative of the body sway of the subject 1728 and a mobile device 1726 having a built-in data processor (see FIGS. 1 and 2). The data processor of the mobile device 1726 is operatively coupled to the inertial measurement unit 1727 and/or camera 1729, the data processor being configured to receive the output data from the inertial measurement unit 1727 and/or camera 1729, and to determine the one or more parameters indicative of the body sway of the subject 1728. In these one or more illustrative embodiments, a fall risk of the subject 1728 may be assessed based upon a combination of the computed center of pressure and the one or more parameters indicative of the body sway determined for the subject 1728. Also, in these one or more illustrative embodiments, the center of pressure for the subject 1728 determined by the data processing device 1716 may be independently computed from the one or more parameters indicative of the body sway for the subject 1728 determined by the mobile device 1726.

Figure 2:
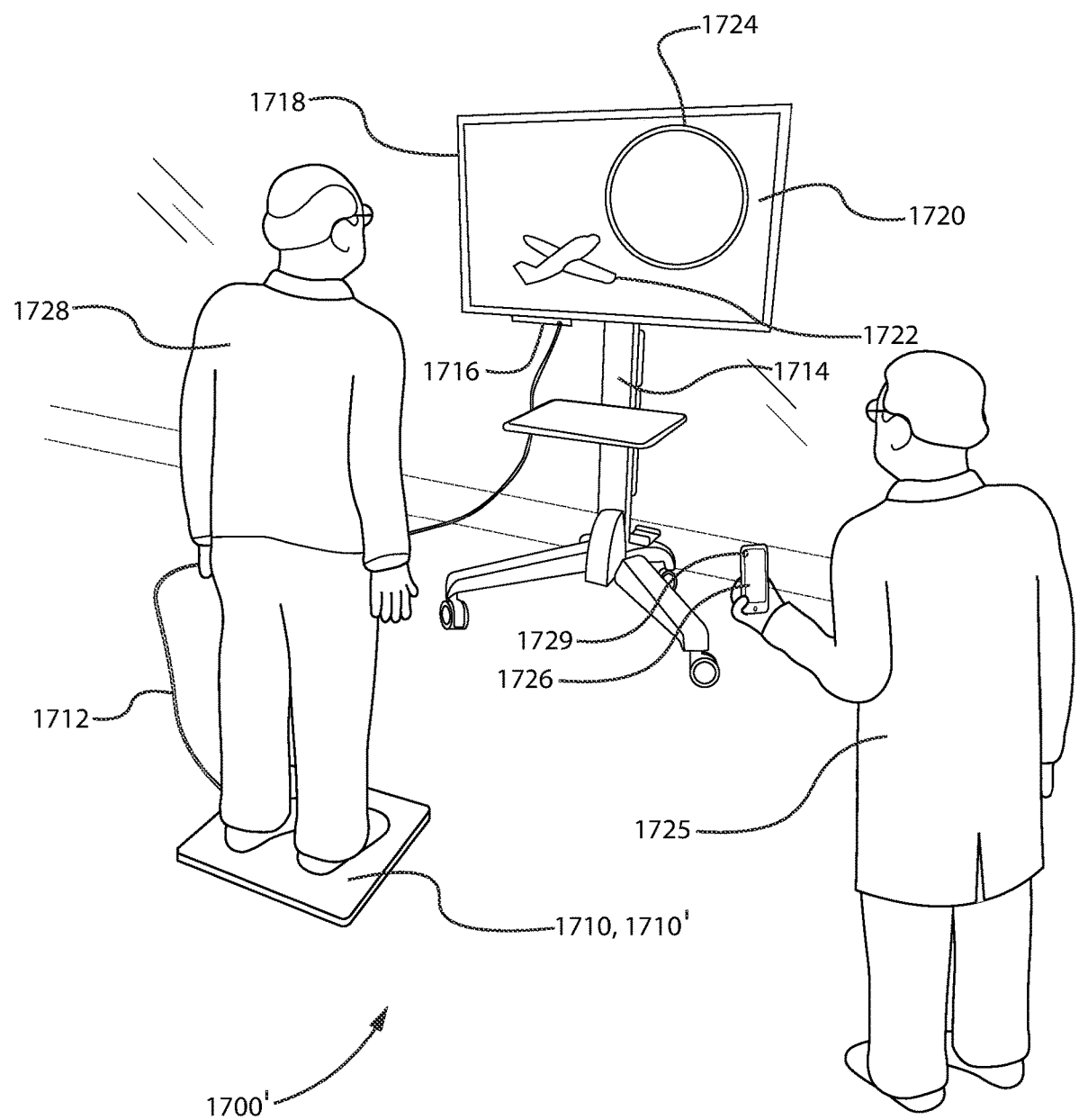
FIG. 2 is a diagrammatic perspective view of a second exemplary force measurement system for measuring the center of pressure and body sway of a subject, according to a further embodiment of the invention.

In the illustrative embodiment of FIGS. 1 and 2, the force measurement system 1700, 1700' further comprises a visual display device 1718 operatively coupled to the data processing device 1716 (e.g., a computing device or a small-form-factor personal computer, such as the Intel® NUC). The small-form-factor personal computer 1716 is one illustrative form of a data processing device and/or data processing and data acquisition device. In FIGS. 1 and 2, the small-form-factor personal computer 1716 may be mounted on the back of the visual display device 1718 (e.g., mounted on the back panel of a touchscreen visual display device with output screen 1720). In one or more embodiments, the screen images described hereinafter are displayed on the output screen 1720 of the visual display device 1718 so that the subject 1728 is able to interact with one or more visual objects in the screen images.

In the illustrative embodiment of FIGS. 1 and 2, the visual display device 1718 is disposed on an adjustable height stand or cart 1714 so that the height of the visual display device 1718 is selectively adjustable by a user. Advantageously, prior to a testing session of the subject 1728, the height of the stand 1714 may be adjusted such that the approximate center of the visual display device 1718 is generally horizontally aligned with the eyes of the standing subject (i.e., so the subject is generally looking at the central portion of the visual display device 1718 during the testing).

Referring again to FIGS. 1 and 2, it can be seen that the illustrative force measurement systems 1700, 1700' include a force measurement assembly 1710, 1710' for determining the center of pressure of the subject 1728. In particular, the force measurement assembly 1710, 1710' may comprise a static force plate that is configured to rest on the floor of the room in which the system 1700, 1700' is disposed (see FIGS. 1 and 2). As will be described in further detail hereinafter, the force plate 1710, 1710' comprises a plurality of force transducers or load cells for measuring the forces and/or moments generated on the plate surface thereof by the feet of the subject 1728. As such, the center of pressure (COP), center of gravity (COG), and/or sway angle of the subject 1728 may be determined while the subject 1728 undergoes testing on the force measurement assembly 1710, 1710'.

In addition, as illustrated in FIGS. 1 and 2, the force measurement assembly 1710, 1710' is operatively coupled to the data processing device 1716 by virtue of an electrical cable 1712. In one embodiment, the electrical cable 1712 is used for data transmission, as well as for providing power to the force measurement assembly 1710, 1710'. Various types of data transmission cables can be used for cable 1712. For example, the cable 1712 can be a Universal Serial Bus (USB) cable or an Ethernet cable. Preferably, the electrical cable 1712 contains a plurality of electrical wires bundled together, with at least one wire being used for power and at least another wire being used for transmitting data. The bundling of the power and data transmission wires into a single electrical cable 1712 advantageously creates a simpler and more efficient design. In addition, it enhances the safety of the training environment for the subject 1728. However, it is to be understood that the force measurement assembly 1710, 1710' can be operatively coupled to the data processing device 1716 using other signal transmission means, such as a wireless data transmission system. If a wireless data transmission system is employed, it is preferable to provide the force measurement assembly 1710, 1710' with a separate power supply in the form of an internal power supply or a dedicated external power supply.

Figure 3:
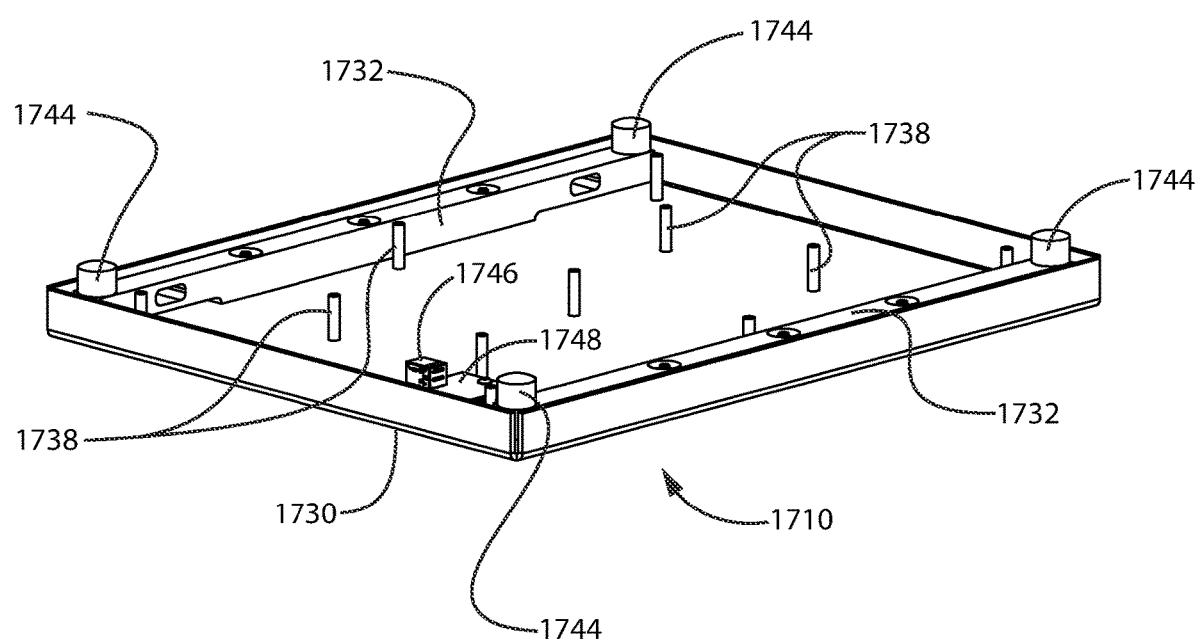
FIG. 3 is a bottom, assembled perspective view of a first type of force measurement assembly used in the force measurement systems of FIGS. 1 and 2.
Figure 4:
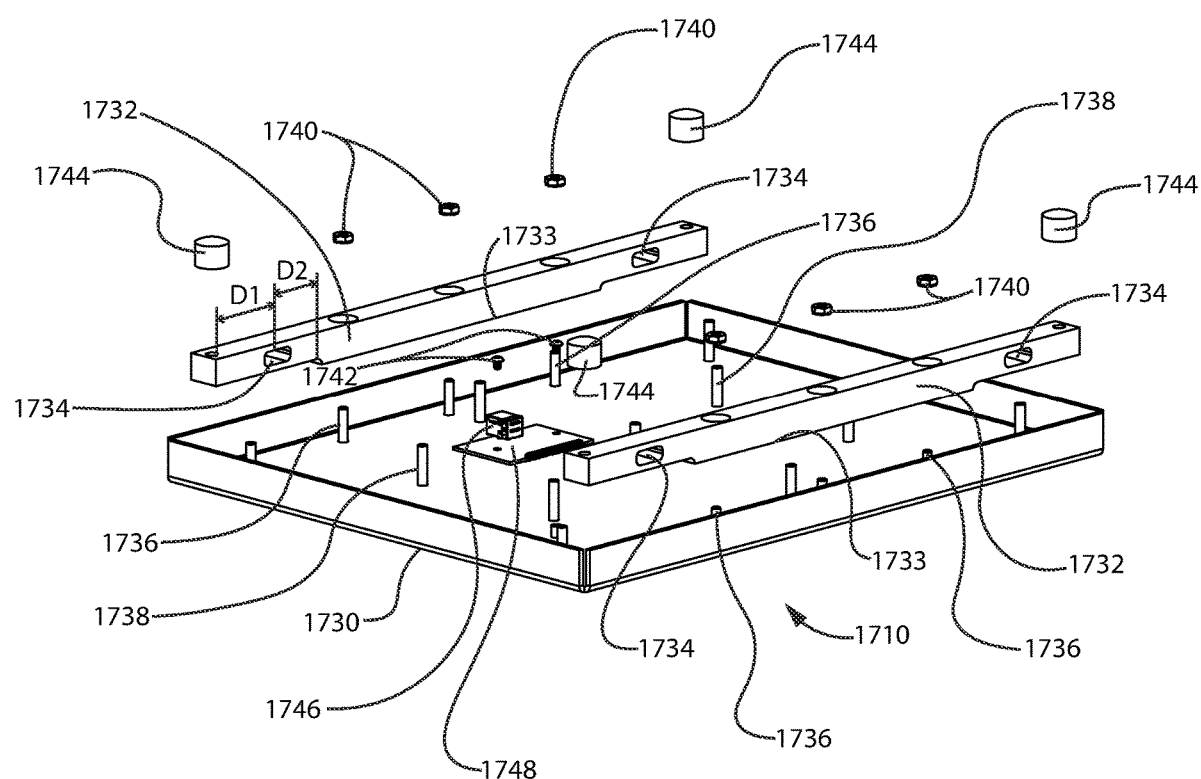
FIG. 4 is a bottom, exploded perspective view of the force measurement assembly of FIG. 3.

Now, with reference to FIGS. 3 and 4, a first illustrative type of force measurement assembly 1710 that may be used in the force measurement systems 1700, 1700' of FIGS. 1 and 2 will be described. As shown in FIGS. 3 and 4, the force measurement assembly 1710 of the illustrated embodiment is in the form of a force plate assembly with a single, continuous measurement surface that measures the vertical force (i.e., $F_Z$) exerted thereon by the subject 1728. The center of pressure (COP) for the subject 1728 may be computed based upon the fraction of the vertical force that is measured by the load cells in each of the corners of the force measurement assembly 1710. The force plate assembly 1710 includes a plate component 1730 supported on a plurality of force transducer beams 1732. As shown in FIGS. 3 and 4, the plate component 1730 comprises a top measurement surface (i.e., a planar top surface) and a plurality of side surfaces extending downward from the top measurement surface. In FIGS. 3 and 4, it can be seen that the bottom surface of the plate component 1730 comprises a first plurality of beam fastener standoffs 1736 and a second plurality of cover fastener standoffs 1738 extending downward from the bottom surface of the plate component 1730. The first plurality of beam fastener standoffs 1736 are used to secure the force transducer beams 1732 to the plate component 1730 (i.e., the first plurality of beam fastener standoffs 1736 together with the securement nuts 1740 secure the force transducer beams 1732 to the underside of the plate component 1730). The second plurality of cover fastener standoffs 1738 are used to secure the bottom cover (not shown) of the force plate assembly 1710 to the underside of the plate component 1730.

In the illustrative embodiment of FIGS. 3 and 4, each of the force transducer beams 1732 is generally in the form of a linear force transducer beam with load cells disposed at the opposite ends of the beam 1732. Each of the load cells measures the vertical force (i.e., $F_Z$) exerted on the plate component 1730 by the subject 1728. Also, as best shown in FIG. 4, each of the load cells is provided with a generally rectangular aperture 1734 disposed through the beam 1732. The apertures 1734 significantly increase the sensitivity of the force transducer beam 1732 when a load is applied thereto by reducing the cross-sectional area of the transducer beam 1732 at the locations of the apertures 1734. Referring again to FIG. 4, it can be seen that each of the force transducer beams 1732 comprises a raised portion or standoff portion 1733 so as to ensure that the total load applied to the plate component 1730 is transmitted through the load cells of the force transducer beams 1732. While not explicitly shown in the figures, it is to be understood that each of the load cells of the force transducer beams 1732 include strain gages mounted on the outer surfaces of the force transducer beams 1732 and centered on the apertures 1734 as described below for the force measurement system of FIGS. 32-34.

Referring again to FIGS. 3 and 4, it can be seen that the force measurement assembly 1710 further includes a pre-amplifier board 1748 for digitizing and conditioning the force output signal from the load cells, and one or more Universal Serial Bus (USB) ports 1746 for operatively coupling the force measurement assembly 1710 to the data processing device 1716 (i.e., the electrical cable 1712 may have a USB plug that is inserted into one of the USB ports 1746). As shown in the exploded view of FIG. 4, the pre-amplifier board 1748 may be secured to the plate component 1730 of the force measurement assembly 1710 by means of securement screws 1742. In one or more embodiments, the pre-amplifier board 1748 also may compute the output forces, the output moments, and/or the center of pressure, and then the data processing device 1716 may perform the remainder of the computations that use the output forces, the output moments, and/or the center of pressure.

Also, as shown in FIGS. 3 and 4, the force measurement assembly 1710 is provided with a plurality of support feet 1744 disposed thereunder. Preferably, each of the four (4) corners of the force measurement assembly 1710 is provided with a support foot 1744 (e.g., mounted on the bottom corner of each force transducer beam 1732. In particular, in the illustrated embodiment, each support foot 1744 is attached to an aperture in a respective corner of one of the force transducer beams 1732 by means of a fastener (e.g., a screw).

With reference again to FIG. 4, it can be seen that the load cells with apertures 1734 are located predetermined distances from the foot members 1744 at the ends of the force transducer beams 1732 so that the load measurement (i.e., of the vertical force $F_Z$) is not affected by stress concentrations on the force transducer beams 1732 resulting from moments developed at the locations of the foot members 1744. For example, as shown in FIG. 4, the center of the load cell aperture 1734 at the left end of the rearward force transducer beam 1732 is located a predetermined distance D1 (e.g., approximately 48 millimeters) from the end of the beam 1732, and the center of the load cell aperture 1734 is located a predetermined distance D2 (e.g., approximately 35 millimeters) from the end of the raised portion or standoff portion 1733 of the beam 1732. In the illustrative embodiment, the distances D1, D2 have been optimized to avoid the edge effects associated with the foot member 1744 (i.e., the accuracy of the load cell output is not adversely affected by any moment that develops at the foot member 1744 as long as the load cell is located a sufficient distance D1 away from the end of the beam 1732 with the foot member 1744). Also, in the illustrative embodiment, the distances D1, D2 have been optimized to maximize the natural frequency of the force measurement assembly 1710. A larger value of D1 minimizes the edge effects because the load cell is further away from the end of the beam 1732. However, a larger value of D1 results in a longer beam 1732 that reduces the natural frequency of the force measurement assembly 1710, and thus results in more noise. As such, the distances D1, D2 are optimized so as to result in an overall beam length that minimizes edge effects, while simultaneously minimizing noise in the load measurement.

In other embodiments, a foot member with a rounded bottom surface can also be used to eliminate the development of a moment at the end of the force transducer beam 1732 (the foot member with a rounded bottom surface allows the force transducer beam 1732 to behave like a cantilever beam). However, the optimization of the distances D1, D2 advantageously eliminates the need for a foot with a rounded bottom surface so that foot members 1744 with the flat bottom surfaces illustrated in FIGS. 3 and 4 may be used.

Next, with reference to FIGS. 5 and 6, a second illustrative type of force measurement assembly 1710' that may be used in the force measurement systems 1700, 1700' of FIGS. 1 and 2 will be described. With reference to these figures, it can be seen that, in some respects, the second illustrative embodiment is similar to that of the first illustrative embodiment of the force measurement assembly 1710 described above. Moreover, some parts are common to both such embodiments. For the sake of brevity, the description of the parts that the second embodiment of the force measurement assembly has in common with the first embodiment will not be repeated with regard to the second embodiment because these components have already been explained in detail above. Furthermore, in the interest of clarity, these components will be denoted using the same reference characters that were used in the first embodiment.

Figure 5:
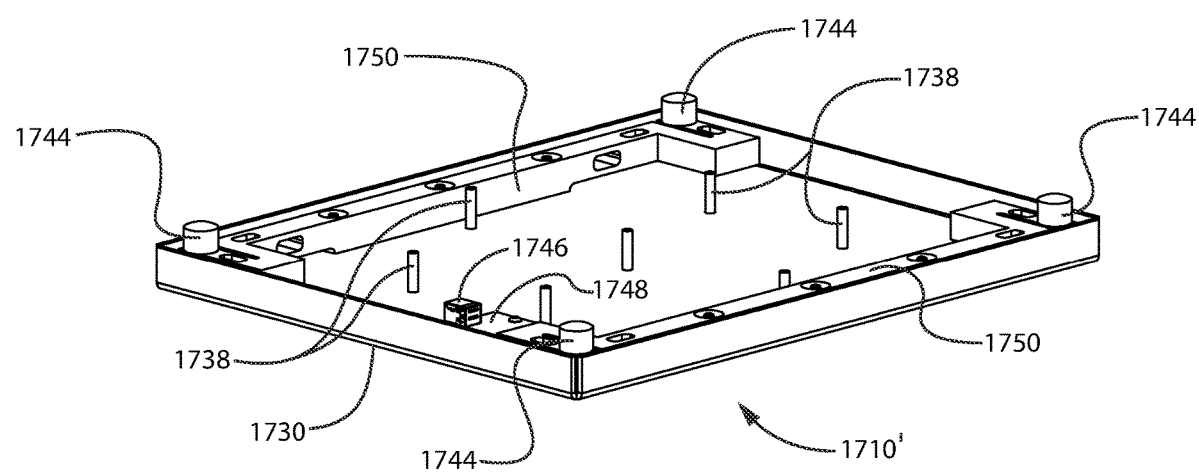
FIG. 5 is a bottom, assembled perspective view of a second type of force measurement assembly used in the force measurement systems of FIGS. 1 and 2.
Figure 6:
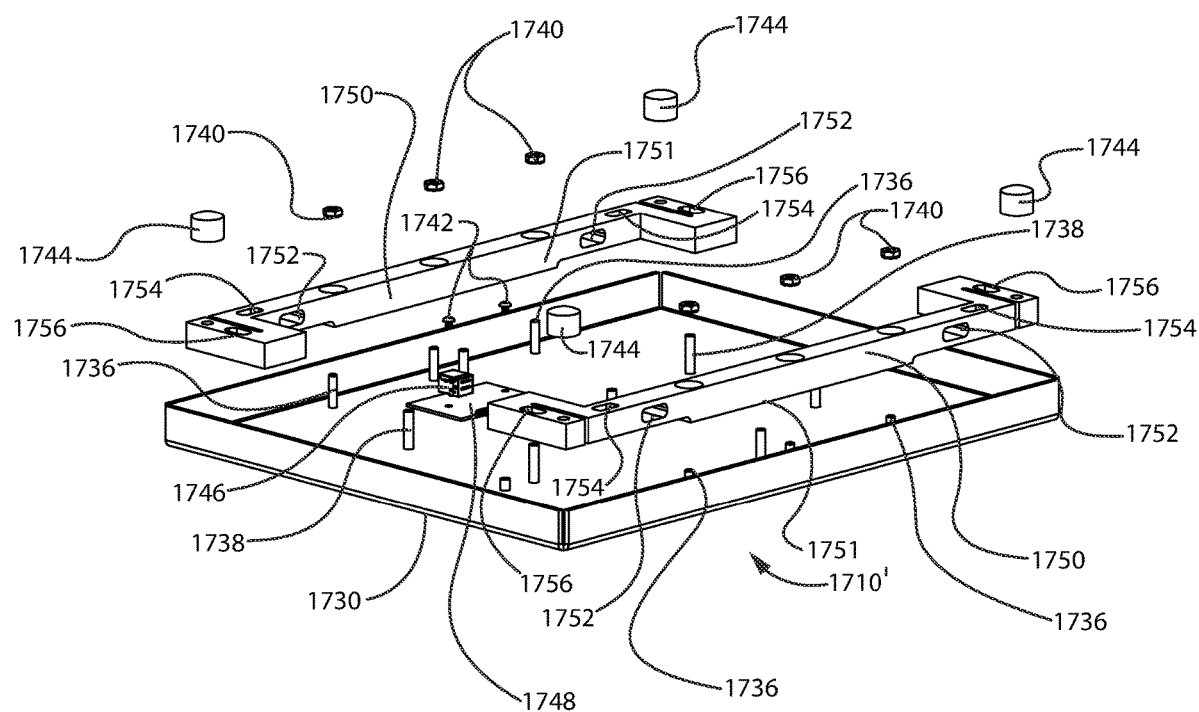
FIG. 6 is a bottom, exploded perspective view of the force measurement assembly of FIG. 5.

Turning to FIGS. 5 and 6, it can be seen that the second illustrative type of force measurement assembly 1710' utilizes a different type of force transducer beam 1750 than the force measurement assembly 1710 described above. More specifically, rather than using a force transducer beam that measures only a single force component, the force measurement assembly 1710' utilizes a multi-component force transducer beam 1750 that measures both the vertical force and the shear forces. In the illustrative embodiment of FIGS. 5 and 6, each of the force transducer beams 1750 has a linear middle portion with generally U-shaped opposed end portions. In the illustrative embodiment, the generally U-shaped end portions of the force transducer beams 1750 each contain three (3) load cells. Also, as best shown in FIG. 6, each of the load cells is provided with generally rectangular apertures 1752, 1754, 1756 disposed through the beam 1750. The first aperture 1752 is associated with the load cell that measures the vertical force (i.e., $F_Z$). The second aperture 1754 is associated with the load cell that measures the first shear force (i.e., $F_X$), while the third aperture 1756 is associated with the load cell that measures the second shear force (i.e., $F_Y$). The apertures 1752, 1754, 1756 significantly increase the sensitivity of the force transducer beam 1750 when a load is applied thereto by reducing the cross-sectional area of the transducer beam 1750 at the locations of the apertures 1752, 1754, 1756. Referring again to FIG. 6, it can be seen that each of the force transducer beams 1750 comprises a raised portion or standoff portion 1751 so as to ensure that the total load applied to the plate component 1730 is transmitted through the load cells of the force transducer beams 1750. While not explicitly shown in the figures, it is to be understood that each of the load cells of the force transducer beams 1750 include strain gages mounted on the outer surfaces of the force transducer beams 1750 and centered on the apertures 1752, 1754, 1756 as described below for the force measurement system of FIGS. 32-34.

In the force measurement systems 1700, 1700' of FIGS. 1 and 2, the mobile device with the data processor is in the form of a smartphone 1726. However, in other embodiments, the mobile device also may be in the form of a tablet computing device, a laptop computing device, or a smartwatch. For example, in the illustrative embodiment, the inertial measurement unit 1727 and/or camera 1729 of the force measurement systems 1700, 1700' may comprise the built-in inertial measurement unit and/or camera of the smartphone 1726. In another illustrative embodiment, rather than a mobile computing device, another type of computing device is used. For example, the other type of computing device may be a desktop computing device, a tower computing device, a server computing device, or a small-form-factor personal computer.

In the illustrative embodiment of FIG. 1, the mobile device 1726 (e.g., the smartphone) comprises the inertial measurement unit 1727 configured to generate the output data for determining the one or more parameters indicative of the body sway of the subject 1728 (i.e., the built-in inertial measurement unit 1727 of the smartphone 1726 is utilized). In this illustrative embodiment, the data processor of the mobile device 1726 is configured to determine the one or more parameters indicative of the body sway of the subject 1728 based upon the output data from the inertial measurement unit 1727 of the mobile device 1726. In the illustrative embodiment, the inertial measurement unit 1727 comprises at least one of an accelerometer configured to detect linear acceleration and a gyroscope configured to detect angular velocity.

For example, as part of the sway analysis, the inertial measurement unit 1727 (i.e., IMU 1727) is capable of measuring gravitational and motion components. The gravitational component makes it possible to define a true vertical vector. The body sway is the angle and translation made by the IMU 1727 around that true vertical. The calculation for the body sway can be done by a principal component analysis (PCA) to approximate the area of body sway excursion (i.e., the body sway envelope) as follows:

$$\sigma_{xy}^2 = \frac{1}{N-1} \sum_{i=1}^{N} (x_i - \bar{x})(y_i - \bar{y}) \tag{1}$$

$$\tan\theta = \frac{\sigma_{xy}^2}{\sigma_0^2 - \sigma_{yy}^2} \tag{2}$$

where $\theta$ in equation (2) above is the body sway angle. In the illustrative embodiment, the computation of the principal component analysis (PCA) set forth in equation (1) may be computed for each joint of the subject 1728.

In one alternative embodiment, the inertial measurement unit that is configured to generate the output data for determining the one or more parameters indicative of the body sway of the subject 1728 is located remotely from the mobile device 1726, rather than being a part of mobile device 1726. In this alternative embodiment, the data processor of the mobile device 1726 is configured to determine the one or more parameters indicative of the body sway of the subject 1728 based upon the output data from the remotely located inertial measurement unit. In this alternative embodiment, the data processor of the mobile device 1726 may be operatively coupled to the remotely located inertial measurement unit by a wireless connection.

In the illustrative embodiment of FIG. 2, the mobile device 1726 (e.g., the smartphone) comprises the camera 1729 configured to generate the output data for determining the one or more parameters indicative of the body sway of the subject 1728 (i.e., the built-in camera 1729 of the smartphone 1726 is utilized). For example, the mobile device 1726 (e.g., the smartphone) may be held by a remote observer 1725, and the camera 1729 of the mobile device 1726 may be focused on the subject 1728. As the subject's body moves due to his or her sway, the image of the subject 1728 is captured by the camera 1729 so that the one or more parameters indicative of the body sway of the subject 1728 may be determined from the image data of the camera 1729.

In the illustrative embodiment of FIG. 2, the data processor of the mobile device 1726 may be configured to determine the one or more parameters indicative of the body sway of the subject 1728 based upon the output data from the camera 1729 using pose estimation. For example, as part of the sway analysis, the camera 1729 is capable of capturing image data of the subject 1728. Then, the data processor of the mobile device 1726 receives the image data of the subject 1728 from the camera 1729. After receiving the image data, the data processor of the mobile device 1726 may then extract features from the image data for providing inputs to a convolutional neural network (CNN). After this step, the data processor of the mobile device 1726 may generate one or more keypoints using a keypoint subnet, and determine one or more poses of the subject 1728 based upon the position of the keypoints.

In one alternative embodiment, the camera that is configured to generate the output data for determining the one or more parameters indicative of the body sway of the subject 1728 is located remotely from the mobile device 1726, rather than being a part of mobile device 1726. In this alternative embodiment, the data processor of the mobile device 1726 is configured to determine the one or more parameters indicative of the body sway of the subject 1728 based upon the output data from the remotely located camera. In this alternative embodiment, the data processor of the mobile device 1726 may be operatively coupled to the remotely located camera by a wireless connection.

Also, in the illustrative embodiment, using the pose estimation described above, the data processor of the mobile device 1726 may determine a displacement curve for any of the keypoints of the user (e.g., a displacement curve for the shoulder joint, elbow joint, knee joint, ankle joint, etc.).

In the illustrative embodiments of FIGS. 1 and 2, the one or more parameters indicative of the body sway of the subject 1728 determined by the data processor of the mobile device 1726 are selected from the group consisting of: (i) a sway angle of the subject, (ii) sway coordinates of the subject, (iii) a sway envelope of the subject.

In the illustrative embodiments of FIGS. 1 and 2, the data processing device 1716 and/or the mobile device 1726 is programmed to determine a mathematical relationship between the center of pressure and the one or more parameters indicative of the body sway for the subject 1728 over a predetermined time period. For example, with regard to the body sway of the subject 1728, the motion of the subject 1728 is modeled as an inverted pendulum with an imaginary vertical line extending lengthwise along the body of the subject 1728. Using the inverted pendulum model, the mathematical relationship that is determined between the center of pressure and the one or more parameters indicative of the body sway for the subject 1728 may be a comparison between the location of one or more coordinate points on the imaginary vertical line extending along the subject 1728 (e.g., one or points proximate to, or higher than the center of gravity (COG) of the subject 1728) and the center of pressure of the subject 1728. Also, in the illustrative embodiments of FIGS. 1 and 2, the data processing device 1716 and/or the mobile device 1726 is programmed to determine the fall risk of the subject 1728 based upon the mathematical relationship between the center of pressure and the one or more parameters indicative of the body sway over the predetermined time period. For example, using the inverted pendulum model, the data processing device 1716 and/or the mobile device 1726 may estimate the fall risk of the subject 1728 by determining if the one or more coordinate points on the imaginary vertical line extending along the subject 1728 (e.g., one or points proximate to, or higher than the center of gravity (COG) of the subject 1728) lags behind the center of pressure of the subject 1728 (a large lag value indicates that the subject 1728 is likely to fall).

In the illustrative embodiments of FIGS. 1 and 2, the output forces and/or moments determined by the data processing device 1716 from the force measurement assembly 1710, 1710' include a shear force in a fore/aft direction of the subject 1728, and the data processing device 1716 is further configured to determine a center of pressure for the subject 1728 using the output forces and/or moments from the force measurement assembly. In these illustrative embodiments, the data processing device 1716 is additionally configured to determine the fall risk of the subject 1728 based upon a combination of the center of pressure and the shear force in the fore/aft direction of the subject 1728. For example, the data processing device 1716 may evaluate the maximum sway range of the center of pressure of the subject 1728 and the magnitude of the shear force in a fore/aft direction of the subject 1728 in order to assess the fall risk of the subject 1728. If both the value of the maximum sway range of the center of pressure of the subject 1728 and the value of the shear force in a fore/aft direction of the subject 1728 are large in magnitude, then the data processing device 1716 may conclude the subject is highly likely to sustain a fall. If at least one of the maximum sway range of the center of pressure of the subject 1728 and the shear force in a fore/aft direction of the subject 1728 is large in magnitude, then the data processing device 1716 may conclude the subject is likely to sustain a fall. If both the value of the maximum sway range of the center of pressure of the subject 1728 and the value of the shear force in a fore/aft direction of the subject 1728 are small in magnitude, then the data processing device 1716 may conclude the subject is unlikely to sustain a fall.

In one variation of the illustrative embodiments of FIGS. 1 and 2, the data processing device 1716 and/or the mobile device 1726 is further programmed to determine the fall risk of the subject based upon a relationship between the one or more parameters indicative of the body sway for the subject 1728 determined by the mobile device 1726 and the shear force in the fore/aft direction of the subject 1728 determined by the data processing device 1716 from the output data of the force measurement assembly 1710, 1710'. For example, the data processing device 1716 and/or the mobile device 1726 may evaluate the magnitude of the maximum sway angle for the subject 1728 and the magnitude of the shear force in a fore/aft direction of the subject 1728 in order to assess the fall risk of the subject 1728. If both the value of the maximum sway angle of the subject 1728 and the value of the shear force in a fore/aft direction of the subject 1728 are large in magnitude, then the data processing device 1716 and/or the mobile device 1726 may conclude the subject is highly likely to sustain a fall. If at least one of the maximum sway angle of the subject 1728 and the shear force in a fore/aft direction of the subject 1728 is large in magnitude, then the data processing device 1716 and/or the mobile device 1726 may conclude the subject is likely to sustain a fall. If both the value of the maximum sway angle of the subject 1728 and the value of the shear force in a fore/aft direction of the subject 1728 are small in magnitude, then the data processing device 1716 and/or the mobile device 1726 may conclude the subject is unlikely to sustain a fall.

Referring again to FIG. 1, in the illustrative embodiment, the visual display device 1718 of the illustrative force measurement systems 1700, 1700' may be configured to display at least one manipulatable element (e.g., an airplane 1722) of an interactive game on the output screen so that the at least one manipulatable element is visible to the subject 1728. In the illustrative embodiment, the data processing device 1716 and/or the mobile device 1726 is programmed to control the movement of the at least one manipulatable element (e.g., an airplane 1722) of the interactive game displayed on the visual display device 1718 by using the center of pressure and the one or more parameters indicative of the body sway for the subject 1728 (e.g., if the user leans forward, the airplane decreases in altitude, while, if the user leans backward, the airplane increases in altitude). In the exemplary interactive game, the fore/aft leaning of the subject 1728 could guide the airplane 1722 through rings or hoops 1724 located at different altitudes in the sky. In the illustrative embodiment, the data processing device 1716 and/or the mobile device 1726 may be further programmed to determine the fall risk of the subject 1728 based upon the performance of the subject 1728 while playing the interactive game (e.g., in the airplane game, the fall risk of the subject 1728 may increase as the number of rings or hoops missed by the subject 1728 increases).

In an alternative embodiment, rather than using the mobile device 1726 to determine the one or more parameters indicative of the body sway for the subject 1728, other suitable means may be used for determining the one or more body sway parameters. For example, to measure the body sway of the subject 1728, one end of an extendable elongated attachment member (e.g., a string) may be attached to the belt of the subject 1728, and the other fixed end of the extendable elongated attachment member (e.g., the string) may be attached to a goniometer (e.g., similar to an extendable dog leash). As another example, to measure the body sway of the subject 1728, a distance measuring laser targeting the mid-portion of the subject 1728 may be used. Also, rather than using a distance measuring laser, an infrared detector or ultrasonic detector may be used to measure the distance to the mid-portion of the subject 1728.

Figure 7:
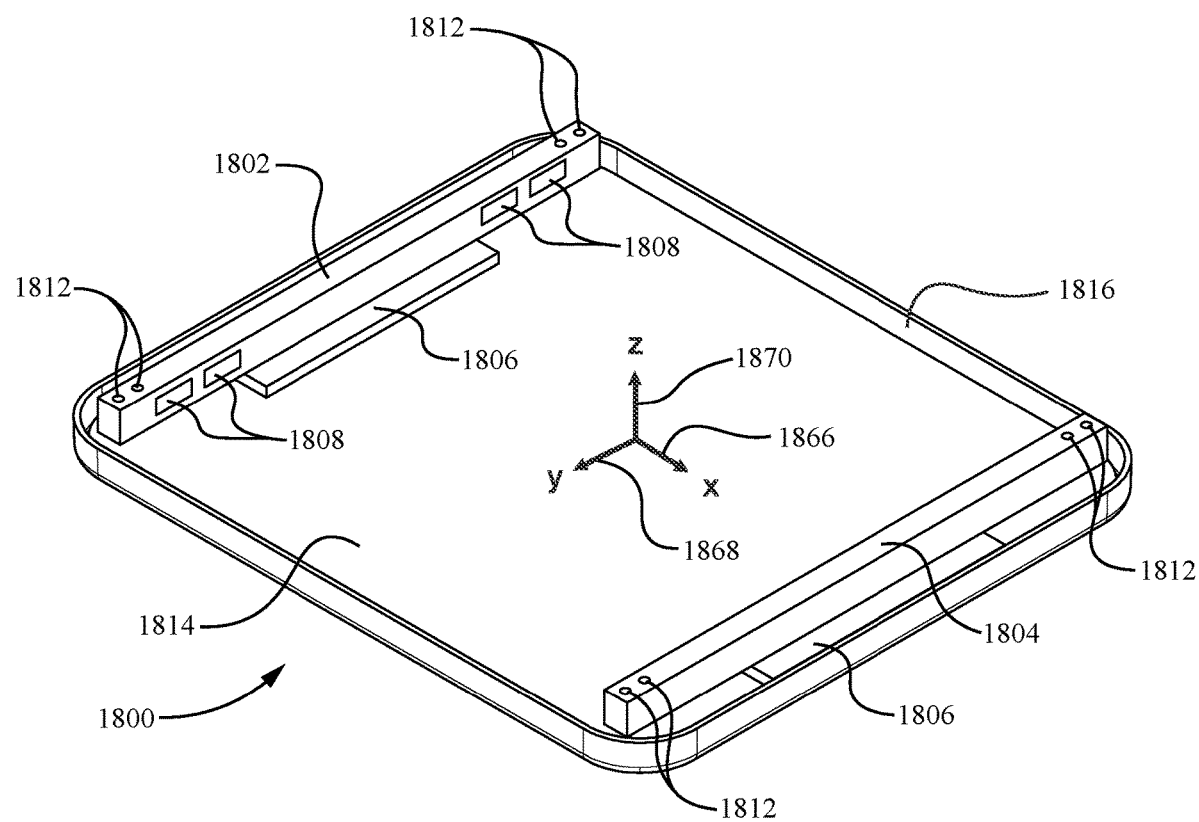
FIG. 7 is a bottom, assembled perspective view of a force measurement assembly, according to still a further embodiment of the invention.
Figure 8:
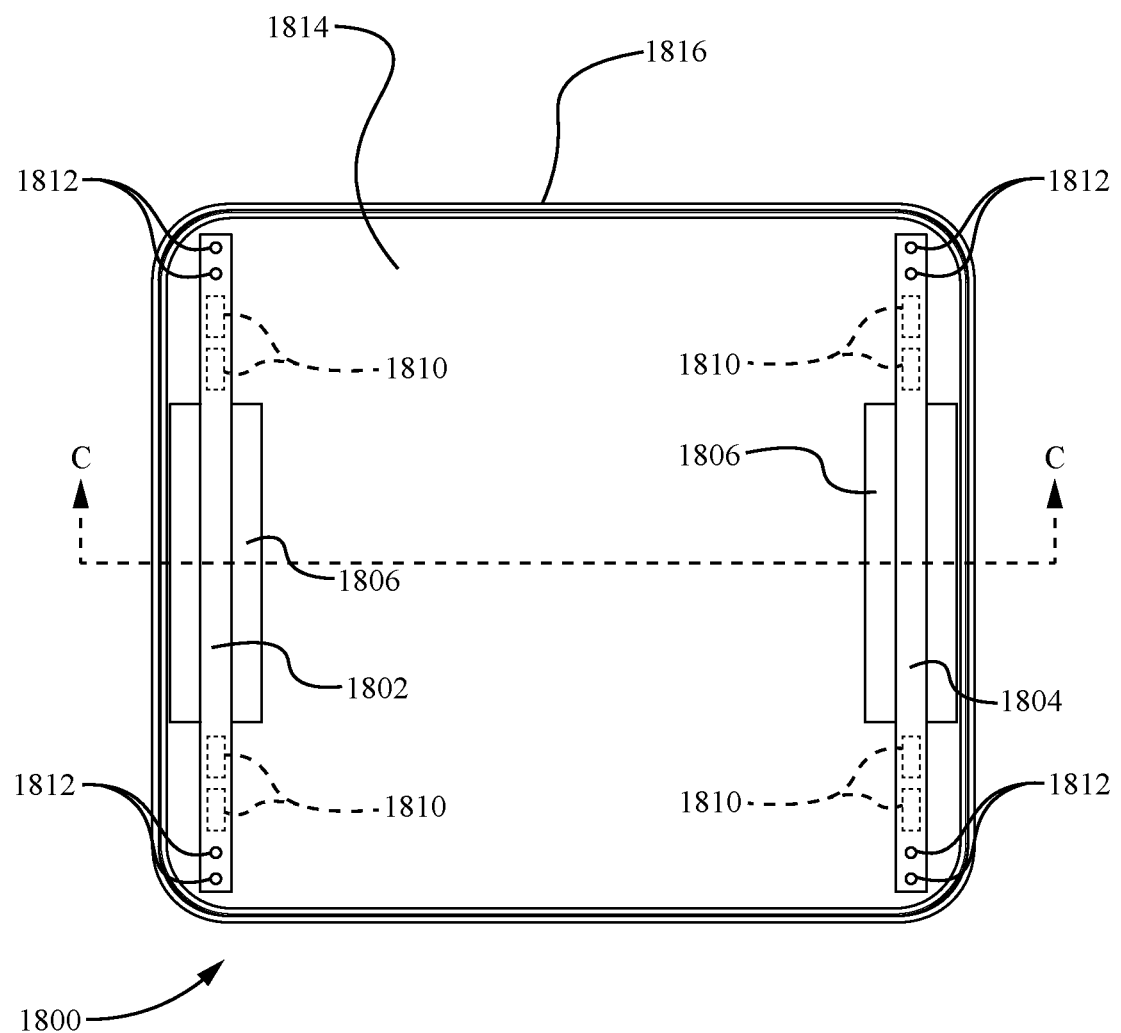
FIG. 8 is a bottom plan view of the force measurement assembly of FIG. 7.
Figure 9:
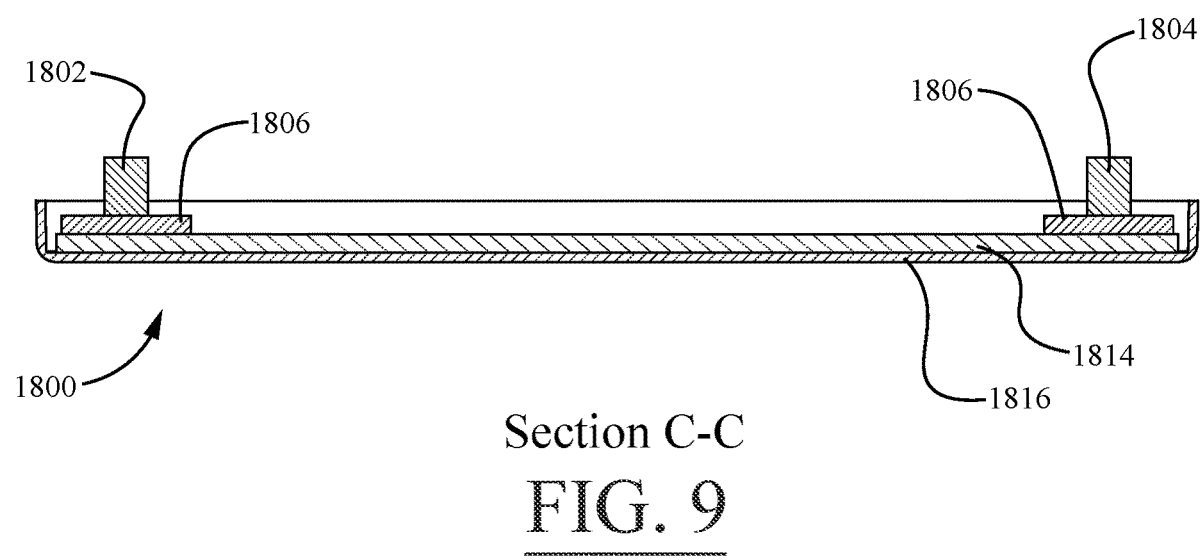
FIG. 9 is a transverse cross-sectional view of the force measurement assembly of FIG. 7, wherein the transverse section is cut through the cutting plane line C-C in FIG. 8.

FIGS. 7-9 illustrate a force measurement assembly 1800 according to a further embodiment of the present invention. In the illustrative embodiment, the force measurement assembly 1800 of FIGS. 7-9 may be provided as part of a force measurement system, and thus may be operatively coupled to a data acquisition/data processing device (e.g., the data acquisition/data processing device 2130 described in conjunction with FIG. 34 below). The functionality of the force measurement system comprising the force measurement assembly 1800 and the data acquisition/data processing device would be generally the same as that described below for the embodiment of FIGS. 32-34, and thus need not be described in detail in conjunction with the description of the force measurement assembly 1800 of FIGS. 7-9. The force measurement assembly 1800 illustrated in FIGS. 7-9 is configured to receive a user/subject thereon, and is capable of measuring the forces and/or moments applied to its measurement surface by the user/subject.

Referring again to FIGS. 7-9, it can be seen that the force measurement assembly 1800 of the illustrated embodiment is in the form of a force plate assembly with a top measurement surface. The force plate assembly includes a top base plate 1814 supported on a plurality of load transducer beams 1802, 1804. In the illustrated embodiment, each load transducer beam 1802, 1804 may be mounted to the underside of the top base plate 1814 by a respective mounting plate 1806. Also, as shown in FIGS. 7-9, the force measurement assembly 1800 further comprises an outer top plate component 1816 that is supported on the top base plate 1814. In the illustrated embodiment, the top base plate 1814 may be formed from aluminum. In the illustrated embodiment, the outer top plate component 1816 may be formed from a suitable polymeric material or plastic (e.g., injection-molded plastic), and may be clipped onto the top base plate 1814.

In the illustrated embodiment of FIGS. 7-9, the force measurement assembly 1800 comprises a pair of spaced-apart load transducer beams 1802, 1804 that are disposed underneath, and near each of the respective sides of the outer top plate component 1816. In the illustrative embodiment of FIGS. 7-9, each of the force transducer beams 1802, 1804 is generally in the form of a linear force transducer beam with load cells disposed at the opposite ends of the beam 1802, 1804. In the illustrated embodiment, the frame portion of each load transducer 1802, 1804 is milled as one solid and continuous piece of a single material. That is, the frame portion of the load transducer beam 1802, 1804 is of unitary or one-piece construction. The frame portion of the load transducer beam 1802, 1804 is preferably machined in one piece from aluminum, titanium, steel, or any other suitable material that meets strength and weight requirements.

Also, as depicted in FIGS. 7 and 8, the load transducer beams 1802, 1804 each comprise a plurality of mounting apertures 1812 (e.g., a pair of mounting apertures 1812) disposed therethrough near the respective beam ends for accommodating fasteners (e.g., screws) that attach the load transducer beams 1802, 1804 to mounting feet of the force plate or force measurement assembly. The load applied to the load transducer beams 1802, 1804 is conveyed through the plurality of beam portions between the mounting plates 1806 and the mounting feet.

Referring collectively to FIGS. 7 and 8, it can be seen that a plurality of deformation sensing elements (e.g., strain gages 1808, 1810) are disposed on the outer surfaces of the frame portions of the load transducer beams 1802, 1804. In particular, in the illustrative embodiment, the strain gages 1810 disposed on the top surfaces of the load transducer beams 1802, 1804 (see FIG. 8) are sensitive to a first force component (i.e., the z-component of the force, $F_Z$) of the load and output one or more first output signals representative of the first force component ($F_Z$) or vertical force ($F_Z$). Also, in the illustrative embodiment, the strain gages 1808 disposed on the inwardly facing side surfaces of the load transducer beams 1802, 1804 (see FIG. 7) are sensitive to a second force component (i.e., the x-component of the force, $F_X$) of the load and output one or more second output signals representative of the second force component ($F_X$) or shear force ($F_X$) in a lateral direction. In the illustrative embodiment, the inwardly facing side surface of the load transducer beam 1802, 1804 on which the strain gages 1808 are disposed is perpendicular or generally perpendicular to the top surface of the load transducer beam 1802, 1804 on which the strain gages 1810 are disposed. Also, in the illustrative embodiment, the first output signals from the strain gages 1810 may be used to determine a center of pressure for the user/subject. More specifically, referring to the perspective view of FIG. 7, it can be seen that the center of pressure coordinates ($x_P$, $y_P$) for the force measurement assembly 1800 may be determined in accordance with x and y coordinate axes 1866, 1868. In FIG. 7, the vertical component of the force ($F_Z$) is defined by the z coordinate axis 1870.

In the illustrative embodiment, the strain gages 1808, 1810 in each strain gage pair at the ends of the load transducer beams 1802, 1804 may be spaced apart from one another by a distance of approximately 1.0 to 2.0 inches, or more preferably, a distance of approximately 1.5 inches.

Figure 10:
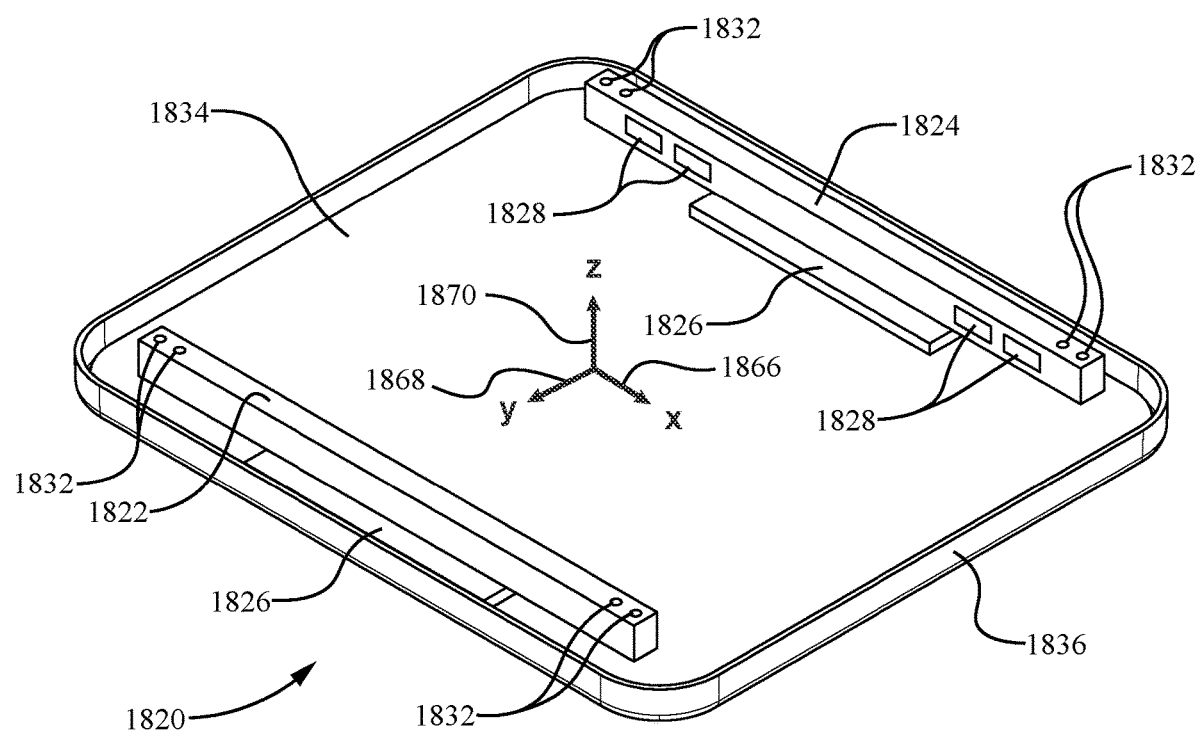
FIG. 10 is a bottom, assembled perspective view of a force measurement assembly, according to yet a further embodiment of the invention.
Figure 11:
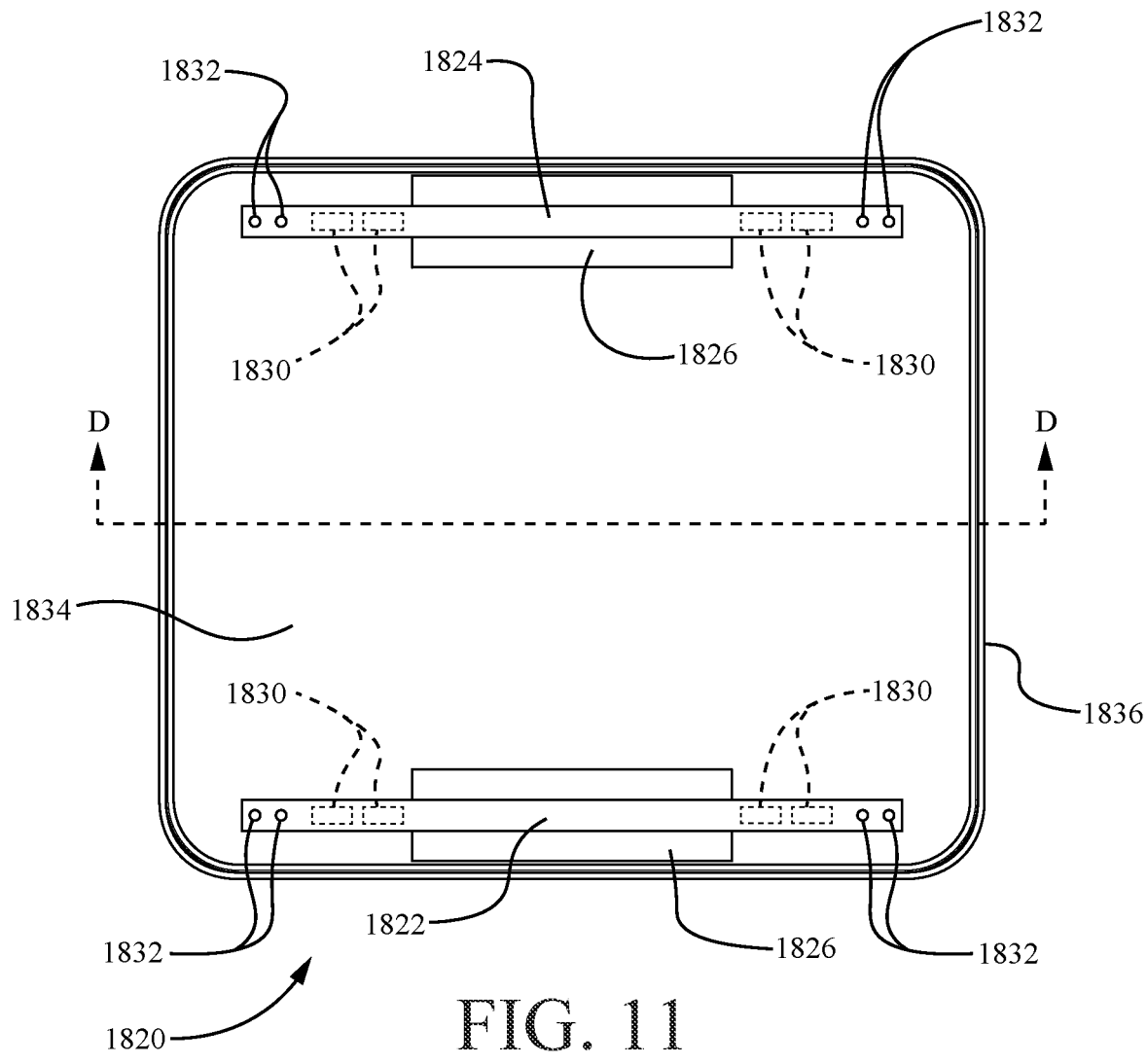
FIG. 11 is a bottom plan view of the force measurement assembly of FIG. 10.
Figure 12:
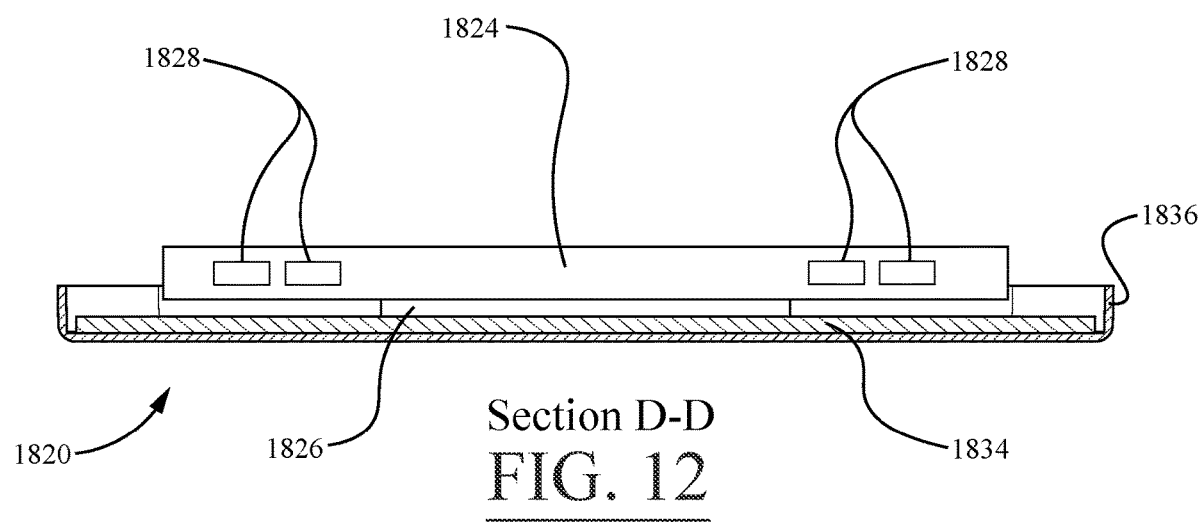
FIG. 12 is a transverse cross-sectional view of the force measurement assembly of FIG. 10, wherein the transverse section is cut through the cutting plane line D-D in FIG. 11.

FIGS. 10-12 illustrate a force measurement assembly 1820 according to yet a further embodiment of the present invention. In the illustrative embodiment, similar to the force measurement assembly 1800 described above, the force measurement assembly 1820 of FIGS. 10-12 may be provided as part of a force measurement system, and thus may be operatively coupled to a data acquisition/data processing device (e.g., the data acquisition/data processing device 2130 described in conjunction with FIG. 34 below). The functionality of the force measurement system comprising the force measurement assembly 1820 and the data acquisition/data processing device would be generally the same as that described below for the embodiment of FIGS. 32-34, and thus need not be described in detail in conjunction with the description of the force measurement assembly 1820 of FIGS. 10-12. Also, like the force measurement assembly 1800 described above, the force measurement assembly 1820 illustrated in FIGS. 10-12 is configured to receive a user/subject thereon, and is capable of measuring the forces and/or moments applied to its measurement surface by the user/subject.

Referring again to FIGS. 10-12, it can be seen that the force measurement assembly 1820 of the illustrated embodiment is in the form of a force plate assembly with a top measurement surface. The force plate assembly includes a top base plate 1834 supported on a plurality of load transducer beams 1822, 1824. In the illustrated embodiment, each load transducer beam 1822, 1824 may be mounted to the underside of the top base plate 1834 by a respective mounting plate 1826. Also, as shown in FIGS. 10-12, the force measurement assembly 1820 further comprises an outer top plate component 1836 that is supported on the top base plate 1834. In the illustrated embodiment, the top base plate 1834 may be formed from aluminum. In the illustrated embodiment, the outer top plate component 1836 may be formed from a suitable polymeric material or plastic (e.g., injection-molded plastic), and may be clipped onto the top base plate 1834.

In the illustrated embodiment of FIGS. 10-12, the force measurement assembly 1820 comprises a pair of spaced-apart load transducer beams 1822, 1824 that are disposed underneath, and near each of the respective sides of the outer top plate component 1836. In the illustrative embodiment of FIGS. 10-12, each of the force transducer beams 1822, 1824 is generally in the form of a linear force transducer beam with load cells disposed at the opposite ends of the beam 1822, 1824. In the illustrated embodiment, the frame portion of each load transducer 1822, 1824 is milled as one solid and continuous piece of a single material. That is, the frame portion of the load transducer beam 1822, 1824 is of unitary or one-piece construction. The frame portion of the load transducer beam 1822, 1824 is preferably machined in one piece from aluminum, titanium, steel, or any other suitable material that meets strength and weight requirements.

Also, as depicted in FIGS. 10 and 11, the load transducer beams 1822, 1824 each comprise a plurality of mounting apertures 1832 (e.g., a pair of mounting apertures 1832) disposed therethrough near the respective beam ends for accommodating fasteners (e.g., screws) that attach the load transducer beams 1822, 1824 to mounting feet of the force plate or force measurement assembly. The load applied to the load transducer beams 1822, 1824 is conveyed through the plurality of beam portions between the mounting plates 1826 and the mounting feet.

Referring collectively to FIGS. 10-12, it can be seen that a plurality of deformation sensing elements (e.g., strain gages 1828, 1830) are disposed on the outer surfaces of the frame portions of the load transducer beams 1822, 1824. In particular, in the illustrative embodiment, the strain gages 1830 disposed on the top surfaces of the load transducer beams 1822, 1824 (see FIG. 11) are sensitive to a first force component (i.e., the z-component of the force, $F_Z$) of the load and output one or more first output signals representative of the first force component ($F_Z$) or vertical force ($F_Z$). Also, in the illustrative embodiment, the strain gages 1828 disposed on the inwardly facing side surfaces of the load transducer beams 1822, 1824 (see FIGS. 10 and 12) are sensitive to a second force component (i.e., the y-component of the force, $F_Y$) of the load and output one or more second output signals representative of the second force component ($F_Y$) or shear force ($F_Y$) in a fore/aft direction. In the illustrative embodiment, the inwardly facing side surface of the load transducer beam 1820, 1824 on which the strain gages 1828 are disposed is perpendicular or generally perpendicular to the top surface of the load transducer beam 1822, 1824 on which the strain gages 1830 are disposed. Also, in the illustrative embodiment, the first output signals from the strain gages 1830 may be used to determine a center of pressure for the user/subject. More specifically, referring to the perspective view of FIG. 10, it can be seen that the center of pressure coordinates ($x_P$, $v_P$) for the force measurement assembly 1820 may be determined in accordance with x and y coordinate axes 1866, 1868. In FIG. 10, the vertical component of the force ($F_Z$) is defined by the z coordinate axis 1870.

In the illustrative embodiment, the strain gages 1828, 1830 in each strain gage pair at the ends of the load transducer beams 1822, 1824 may be spaced apart from one another by a distance of approximately 1.0 to 2.0 inches, or more preferably, a distance of approximately 1.5 inches.

Figure 13:
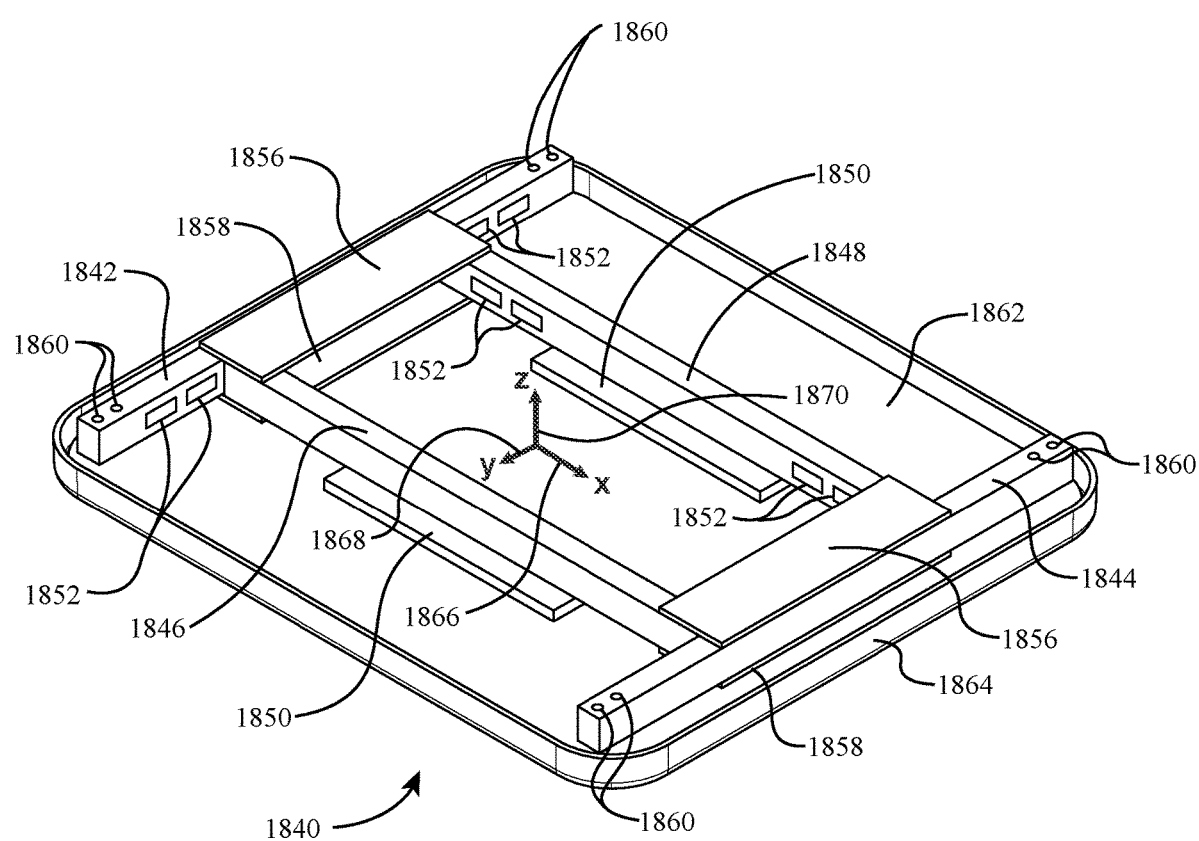
FIG. 13 is a bottom, assembled perspective view of a force measurement assembly, according to still a further embodiment of the invention.
Figure 14:
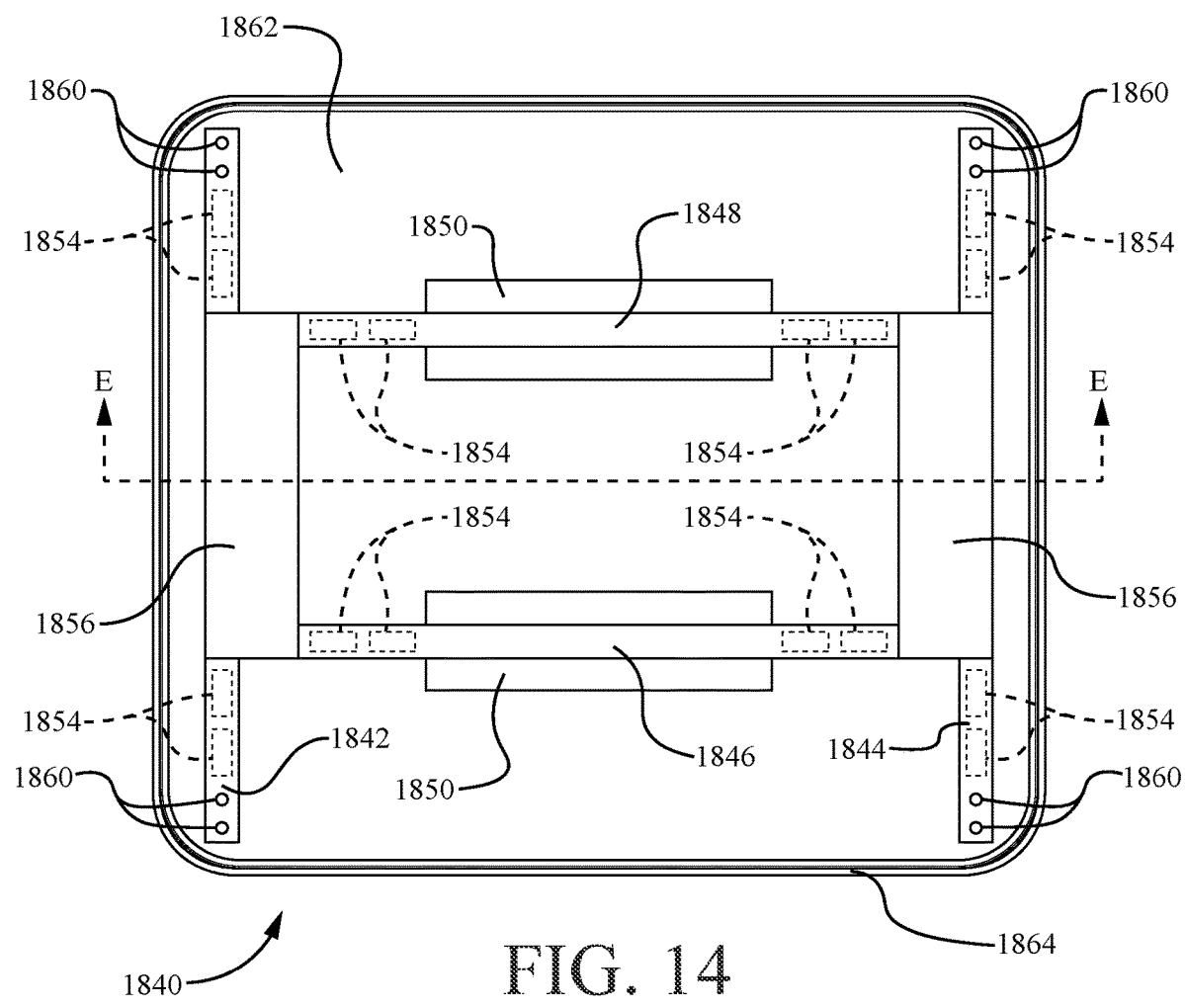
FIG. 14 is a bottom plan view of the force measurement assembly of FIG. 13.
Figure 15:
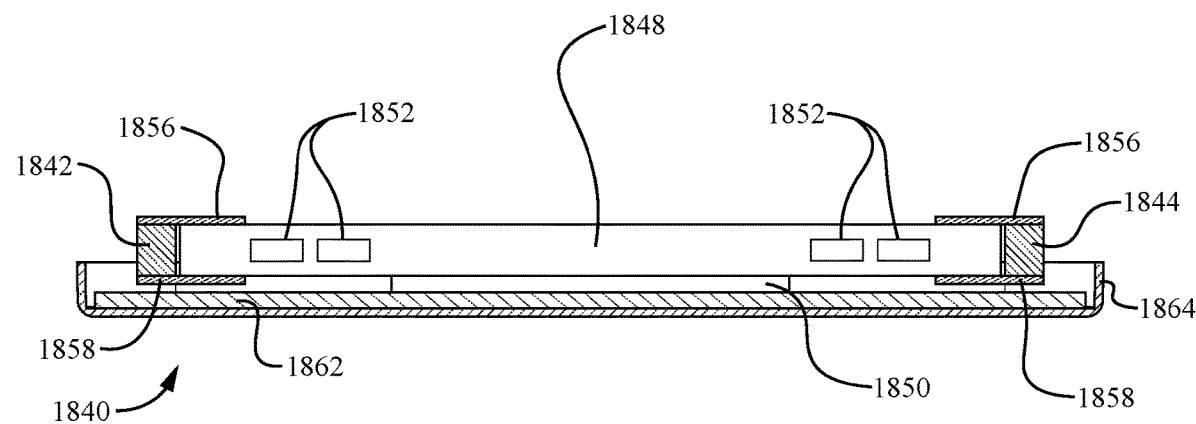
FIG. 15 is a transverse cross-sectional view of the force measurement assembly of FIG. 13, wherein the transverse section is cut through the cutting plane line E-E in FIG. 14.

FIGS. 13-15 illustrate a force measurement assembly 1840 according to yet a further embodiment of the present invention. In the illustrative embodiment, the force measurement assembly 1840 of FIGS. 13-15 may be provided as part of a force measurement system, and thus may be operatively coupled to a data acquisition/data processing device (e.g., the data acquisition/data processing device 2130 described in conjunction with FIG. 34 below). The functionality of the force measurement system comprising the force measurement assembly 1840 and the data acquisition/data processing device would be generally the same as that described below for the embodiment of FIGS. 32-34, and thus need not be described in detail in conjunction with the description of the force measurement assembly 1840 of FIGS. 13-15. Also, like the force measurement assembly 1800 described above, the force measurement assembly 1840 illustrated in FIGS. 13-15 is configured to receive a user/subject thereon, and is capable of measuring the forces and/or moments applied to its measurement surface by the user/subject.

Referring again to FIGS. 13-15, it can be seen that the force measurement assembly 1840 of the illustrated embodiment is in the form of a force plate assembly with a top measurement surface. The force plate assembly includes a top base plate 1862 supported on a plurality of load transducer beams 1842, 1844, 1846, 1848. In the illustrated embodiment, each load transducer beam 1842, 1844, 1846, 1848 may be mounted to the underside of the top base plate 1862 by a respective mounting plate 1850, 1858. Also, as shown in FIGS. 13-15, the force measurement assembly 1840 further comprises an outer top plate component 1864 that is supported on the top base plate 1862. In the illustrated embodiment, the top base plate 1862 may be formed from aluminum. In the illustrated embodiment, the outer top plate component 1864 may be formed from a suitable polymeric material or plastic (e.g., injection-molded plastic), and may be clipped onto the top base plate 1862.

In the illustrated embodiment of FIGS. 13-15, the force measurement assembly 1840 comprises a first pair of spaced-apart load transducer beams 1842, 1844 that are disposed underneath, and near each of the respective sides of the outer top plate component 1864. In the illustrative embodiment of FIGS. 13-15, each of the force transducer beams 1842, 1844 is generally in the form of a linear force transducer beam with load cells disposed at the opposite ends of the beam 1842, 1844. In the illustrated embodiment, the frame portion of each load transducer 1842, 1844 is milled as one solid and continuous piece of a single material. That is, the frame portion of the load transducer beam 1842, 1844 is of unitary or one-piece construction. The frame portion of the load transducer beam 1842, 1844 is preferably machined in one piece from aluminum, titanium, steel, or any other suitable material that meets strength and weight requirements.

In the illustrated embodiment of FIGS. 13-15, the force measurement assembly 1840 further comprises a second pair of spaced-apart load transducer beams 1846, 1848 that are disposed between the load transducer beams 1842, 1844, and are disposed inwardly from the load cells of load transducer beams 1842, 1844. In the illustrative embodiment of FIGS. 13-15, each of the force transducer beams 1846, 1846 is generally in the form of a linear force transducer beam with load cells disposed at the opposite ends of the beam 1846, 1848. In the illustrated embodiment, the frame portion of each load transducer 1846, 1848 is milled as one solid and continuous piece of a single material. That is, the frame portion of the load transducer beam 1846, 1848 is of unitary or one-piece construction. The frame portion of the load transducer beam 1846, 1848 is preferably machined in one piece from aluminum, titanium, steel, or any other suitable material that meets strength and weight requirements. As shown in FIGS. 13-15, the end portions of the load transducer beams 1846, 1848 are rigidly connected to the middle portions of the load transducer beams 1842, 1844 by lower beam connector plates 1856 and upper beam connector plates 1858.

In the illustrated embodiment, the load transducer beams 1842, 1844, 1846, 1848 have a modular construction such that a single load transducer beam of the same type is configured to be interchangeably used for each of the load transducer beams 1842, 1844, 1846, 1848 (i.e., a modular load transducer beam is able to be positioned in any of the four (4) different positions on the force measurement assembly 1840, and the modular load transducer beam is configured to be combined with the other load transducer beams on the force measurement assembly 1840 to form the combined measurement structure). Advantageously, the use of a modular load transducer beam obviates the need for unique parts for each of the load transducer beams 1842, 1844, 1846, 1848).

Also, as depicted in FIGS. 13 and 14, the load transducer beams 1842, 1844 each comprise a plurality of mounting apertures 1860 (e.g., a pair of mounting apertures 1860) disposed therethrough near the respective beam ends for accommodating fasteners (e.g., screws) that attach the load transducer beams 1842, 1844 to mounting feet of the force plate or force measurement assembly.

Referring collectively to FIGS. 13-15, it can be seen that a plurality of deformation sensing elements (e.g., strain gages 1852, 1854) are disposed on the outer surfaces of the frame portions of the load transducer beams 1842, 1844, 1846, 1848. In particular, in the illustrative embodiment, the strain gages 1854 disposed on the top surfaces of the load transducer beams 1842, 1844, 1846, 1848 (see FIG. 14) are sensitive to a first force component (i.e., the z-component of the force, $F_Z$) of the load and output one or more first output signals representative of the first force component ($F_Z$) or vertical force ($F_Z$). Also, in the illustrative embodiment, the strain gages 1852 disposed on the inwardly facing side surfaces of the load transducer beams 1842, 1844 (see FIG. 13) are sensitive to a second force component (i.e., the x-component of the force, $F_X$) of the load and output one or more second output signals representative of the second force component ($F_X$) or shear force ($F_X$) in a lateral direction. In addition, in the illustrative embodiment, the strain gages 1852 disposed on the inwardly facing side surfaces of the load transducer beams 1846, 1848 (see FIGS. 13 and 15) are sensitive to a third force component (i.e., the y-component of the force, $F_Y$) of the load and output one or more third output signals representative of the second force component ($F_Y$) or shear force ($F_Y$) in a fore/aft direction. In the illustrative embodiment, the inwardly facing side surface of the load transducer beam 1842, 1844, 1846, 1848 on which the strain gages 1852 are disposed is perpendicular or generally perpendicular to the top surface of the load transducer beam 1842, 1844, 1846, 1848 on which the strain gages 1854 are disposed. Also, in the illustrative embodiment, the first output signals from the strain gages 1854 may be used to determine a center of pressure for the user/subject. More specifically, referring to the perspective view of FIG. 13, it can be seen that the center of pressure coordinates ($x_P$, $y_P$) for the force measurement assembly 1840 may be determined in accordance with x and y coordinate axes 1866, 1868. In FIG. 13, the vertical component of the force ($F_Z$) is defined by the z coordinate axis 1870.

Further, in the illustrative embodiment, the data processing device is further configured to determine a torque about the vertical axis 1870 for the user/subject using the output data from the force measurement assembly 1840 (e.g., in a golf application of the force measurement assembly 1840).

In the illustrative embodiment, the strain gages 1852, 1854 in each strain gage pair at the ends of the load transducer beams 1842, 1844, 1846, 1848 may be spaced apart from one another by a distance of approximately 1.0 to 2.0 inches, or more preferably, a distance of approximately 1.5 inches.

One or more further illustrative embodiments will be described with reference to FIGS. 16-23. In these one or more further illustrative embodiments, with reference initially to FIG. 19, the force measurement system comprises a plurality of force measurement assemblies 1900a, 1900b, 1900c, 1900d, 1900e, 1900f, where at least some of the plurality of force measurement assemblies (e.g., force measurement assemblies 1900a, 1900b) are configured to be independently displaceable from other ones of the plurality of force measurement assemblies (e.g., force measurement assemblies 1900c, 1900d, 1900e, 1900f) such that one or more particular ones of the plurality of force measurement assemblies that are disposed underneath a subject varies over time. In these one or more further embodiments, each of the plurality of force measurement assemblies 1900a, 1900b, 1900c, 1900d, 1900e, 1900f includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject. Also, in these one or more further embodiments, the force measurement system further comprises one or more data processing devices operatively coupled to each of the force transducers of each of the force measurement assemblies, the one or more data processing devices configured to receive each of the one or more signals that are representative of the one or more measured quantities and to convert the one or more signals into load output data, the load output data comprising one or more forces and/or one or more moments.

Figure 16:
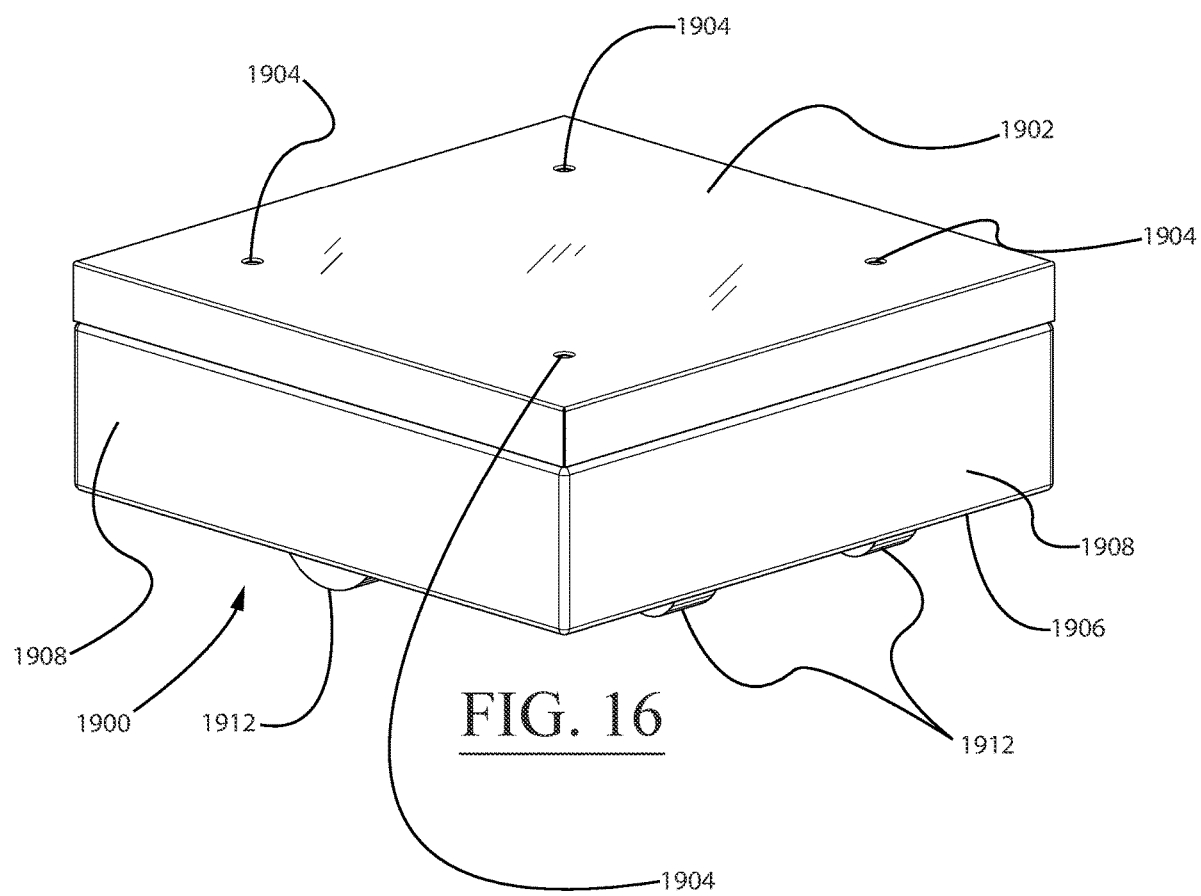
FIG. 16 is a top perspective view of an independently displaceable force measurement assembly of a force measurement system, according to yet a further embodiment of the invention.
Figure 17:
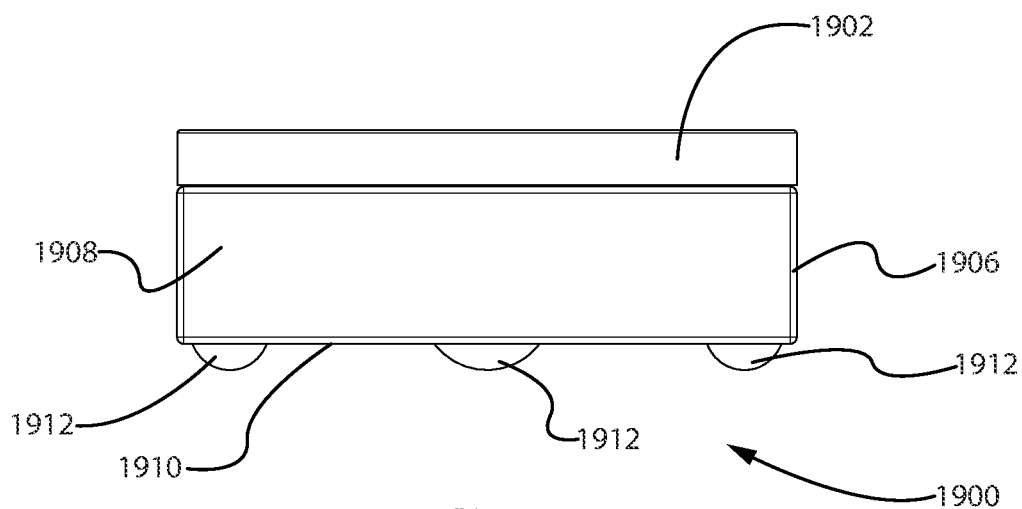
FIG. 17 is a side elevational view of the force measurement assembly of FIG. 16.
Figure 18:
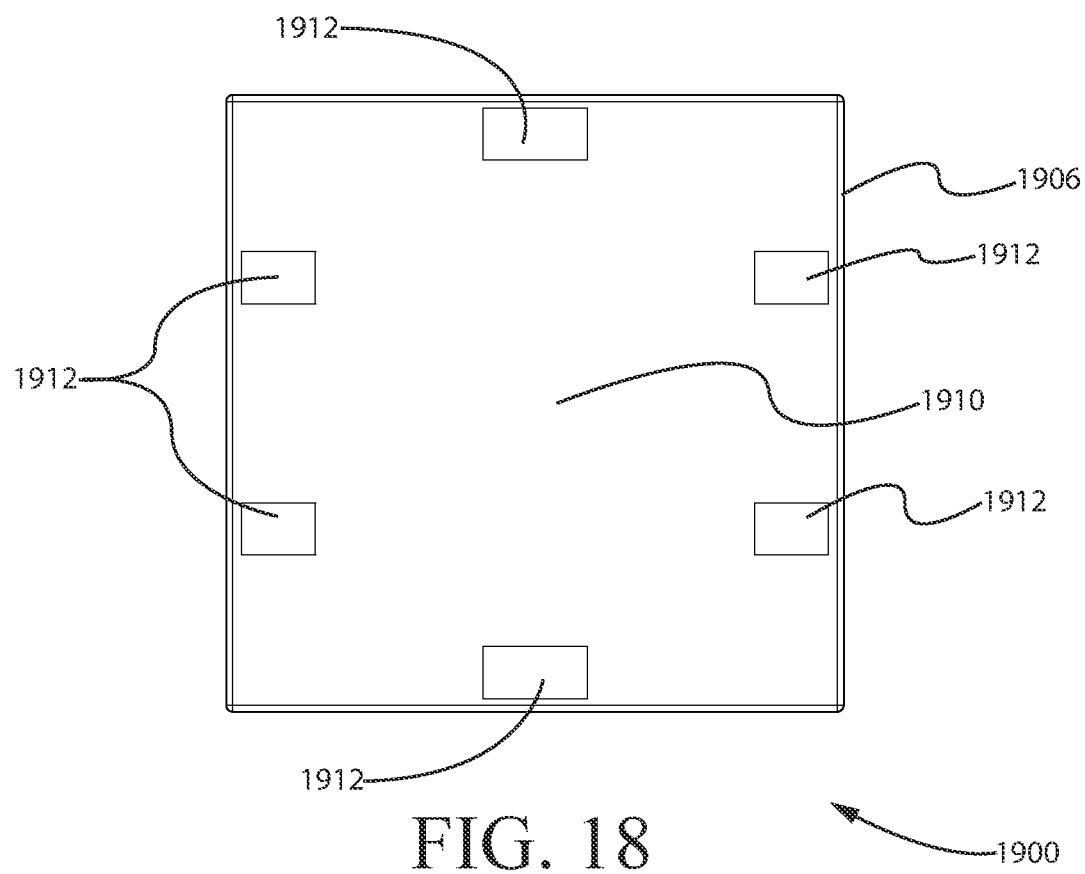
FIG. 18 is a bottom plan view of the force measurement assembly of FIG. 16.
Figure 19:
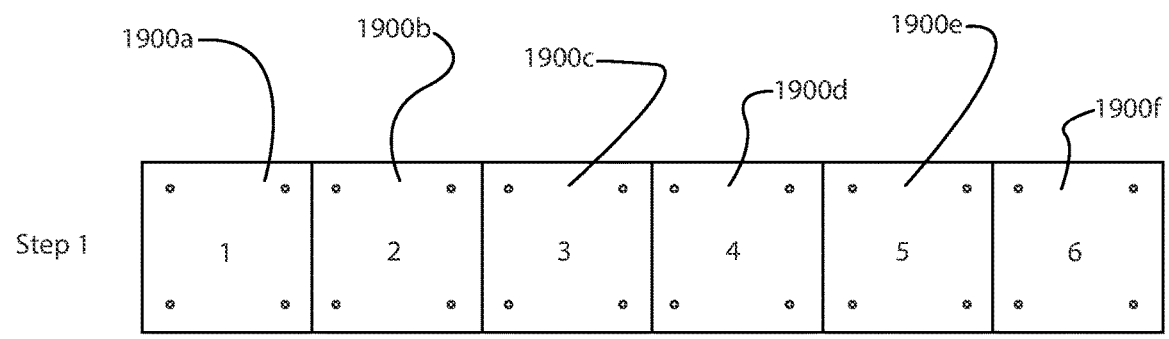
FIG. 19 is a top plan view of a force measurement system comprising a plurality of independently displaceable force measurement assemblies, wherein the plurality of independently displaceable force measurement assemblies are arranged in a first linear arrangement.
Figure 20:
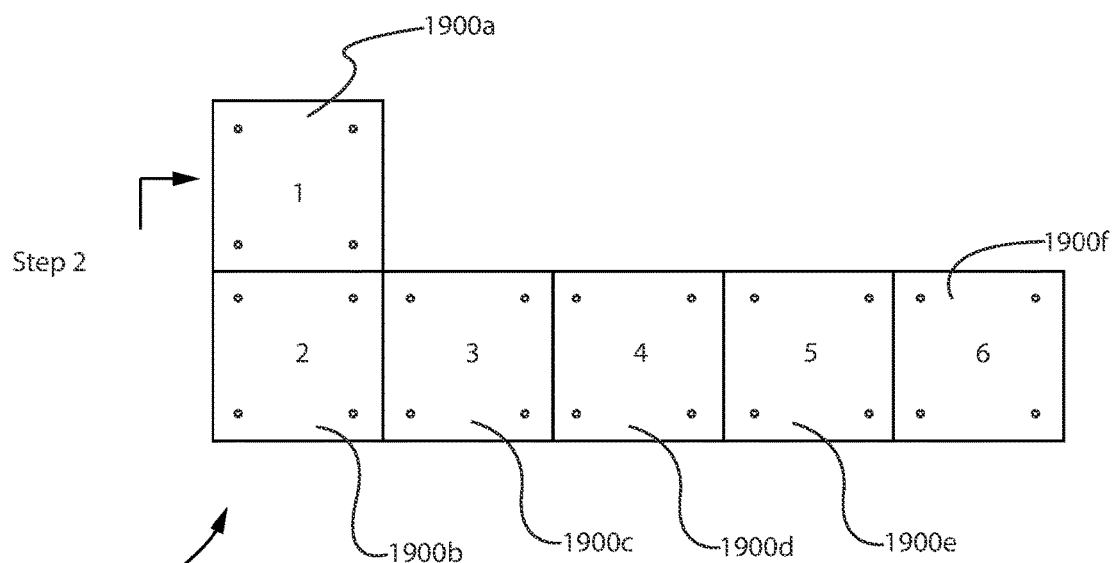
FIG. 20 is another top plan view of the force measurement system of FIG. 19, wherein one of the force measurement assemblies is shown being displaced to a first position along a side of the other force measurement assemblies in the system.
Figure 21:
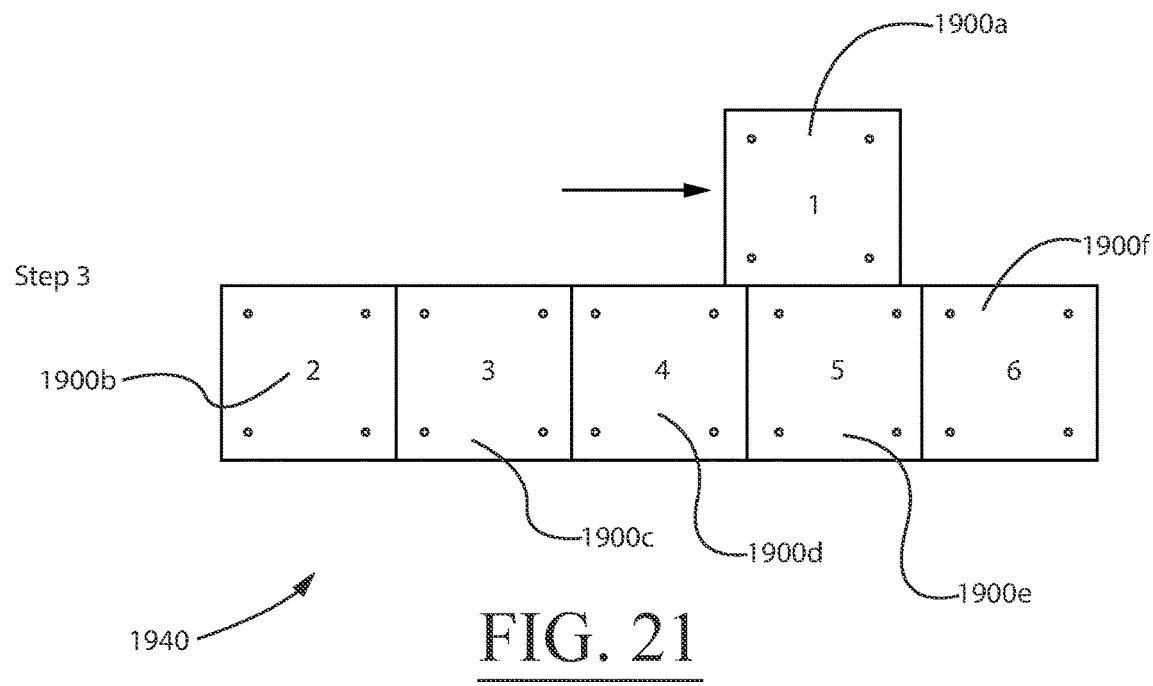
FIG. 21 is yet another top plan view of the force measurement system of FIG. 19, wherein the displaced one of the force measurement assemblies is shown being displaced to a further second position along the side of the other force measurement assemblies in the system.
Figure 22:
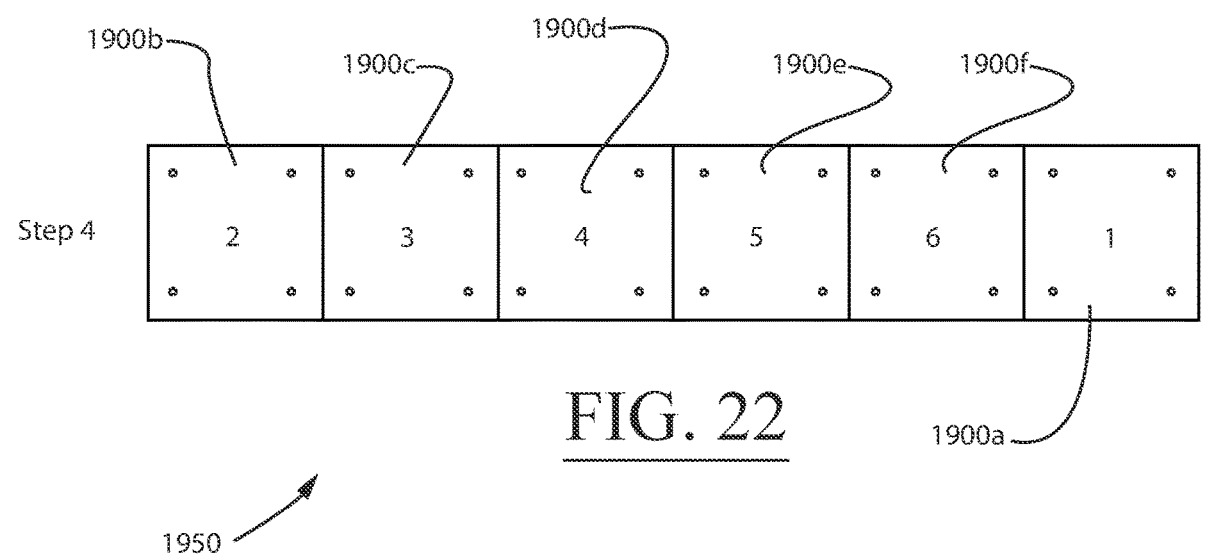
FIG. 22 is still another top plan view of the force measurement system of FIG. 19, wherein the displaced one of the force measurement assemblies is shown being displaced to a third position in front of the other force measurement assemblies in the system.

An illustrative one 1900 of the independently displaceable force measurement assemblies 1900a, 1900b, 1900c, 1900d, 1900e, 1900f is shown in FIGS. 16-18. With initial reference to the perspective view of FIG. 16, it can be seen that the independently displaceable force measurement assembly 1900 includes a force plate 1902 mounted on a top of a displaceable support carriage 1906. The displaceable support carriage 1906 is configured to be selectively displaced on a support surface (e.g., a floor of a building). In the illustrative embodiment, the force plate 1902 may be attached to the displaceable support carriage 1906 by a plurality of fastener members 1904 (e.g., four (4) recessed screws). With combined reference to FIGS. 16-18, in the illustrative embodiment, the displaceable support carriage 1906 comprises a plurality of side panels 1908 and a bottom panel 1910 for covering internal components (e.g., portions of the wheels 1912, the wheel actuators, etc.) of the support carriage 1906. In the illustrative embodiment, the force plate 1902 of the force measurement assembly 1900 may be in the form of one of the force plates 1710, 1710', 1800, 1820, 1840 described above.

Referring again to FIGS. 16-18, in the illustrative embodiment, the displaceable support carriage 1906 comprises a plurality of wheels 1912 disposed on a bottom of the displaceable support carriage 1906 for selectively displacing the force measurement assembly 1900 on the support surface. In the illustrative embodiment, the wheels 1912 do not pivot about a vertical axis (i.e., the wheels are non-steerable), and a turning direction of the force measurement assembly 1900 is determined by selectively activating one or more of the plurality of wheels 1912 in a first rotational direction and selectively activating one or more other ones of the plurality of wheels 1912 in a second rotational direction, where the first rotational direction is opposite to the second rotational direction. In the illustrative embodiment, a skid steering technique may be used for turning the displaceable support carriage 1906. For example, when it is desired to turn the displaceable support carriage 1906 to the right, the wheels 1912 on the left side of the displaceable support carriage 1906 are rotated in a forward direction, while the wheels 1912 on the right side of the displaceable support carriage 1906 are rotated in a reverse direction. When it is desired for the displaceable support carriage 1906 to go straight, all of the wheels 1912 are rotated in a forward direction. In the illustrative embodiment, the wheels 1912 are driven in a selected forward or reverse direction by actuators that are under the control of the one or more data processing devices such that the one or more data processing devices are able to control the movement of the individual force measurement assemblies 1900, 1900a, 1900b, 1900c, 1900d, 1900e, 1900f in the force measurement system.

In an alternative embodiment, one or more of the plurality of wheels 1912 on the displaceable support carriage 1906 are pivotable (i.e., steerable), and a turning direction of the force measurement assembly 1900 is determined by rotating the one or more of the plurality of wheels 1912 to a selected angular position.

Now, turning to FIGS. 19-22, a first illustrative arrangement of force measurement assemblies 1900a, 1900b, 1900c, 1900d, 1900e, 1900f will be described. Initially, in the initial configuration 1920 of FIG. 19, all of the force measurement assemblies 1900a, 1900b, 1900c, 1900d, 1900e, 1900f are arranged in a linear configuration. Then, in the next configuration 1930 of FIG. 20, it can be seen that the rearmost force measurement assembly 1900a is starting to be displaced along the side of the other force measurement assemblies 1900b, 1900c, 1900d, 1900e, 1900f. In the configuration 1940 of FIG. 21, the force measurement assembly 1900a has traveled further along the side of the other force measurement assemblies 1900b, 1900c, 1900d, 1900e, 1900f. Finally, in the configuration 1950 of FIG. 22, the force measurement assembly 1900a has reached its final displacement location in front of the other force measurement assemblies 1900b, 1900c, 1900d, 1900e, 1900f.

In the first illustrative arrangement of FIGS. 19-22, one or more of the plurality of force measurement assemblies (e.g., force measurement assembly 1900a) are configured to be continually displaced from a posterior position behind a subject to an anterior position in front of the subject in order to maintain a generally consistent quantity of the plurality of force measurement assemblies disposed underneath the subject while the subject is walking or running on the plurality of force measurement assemblies 1900a, 1900b, 1900c, 1900d, 1900e, 1900f. In the arrangement of FIGS. 19-22, when the one or more of the plurality of force measurement assemblies (e.g., force measurement assembly 1900a) are displaced from the posterior position behind the subject to the anterior position in front of the subject, the one or more of the plurality of force measurement assemblies (e.g., force measurement assembly 1900a) are displaced along a side of the plurality of force measurement assemblies disposed underneath the subject (e.g., along a side of the force measurement assemblies 1900b, 1900c, 1900d, 1900e, 1900f).

Figure 23:
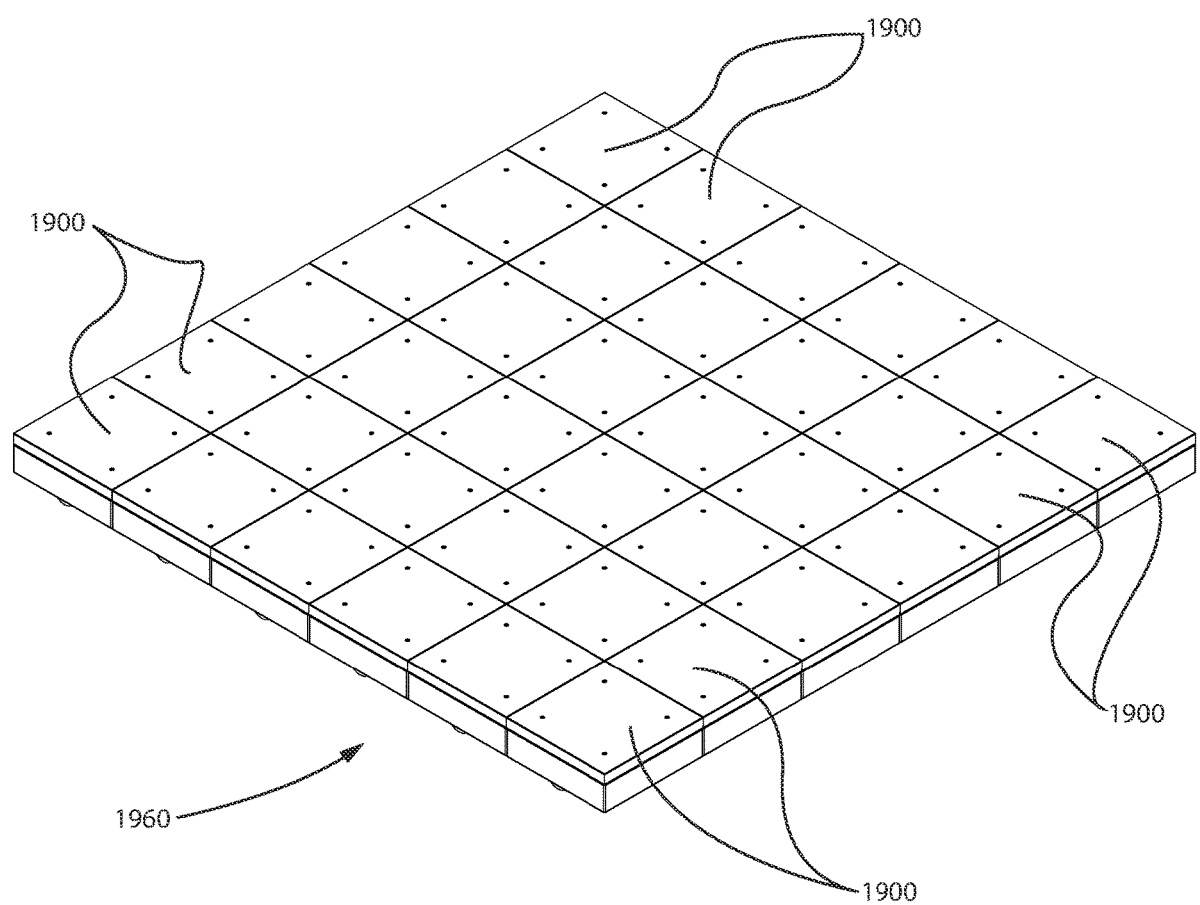
FIG. 23 is a perspective view of a force measurement system comprising a plurality of independently displaceable force measurement assemblies arranged in a matrix configuration.
Figure 24:
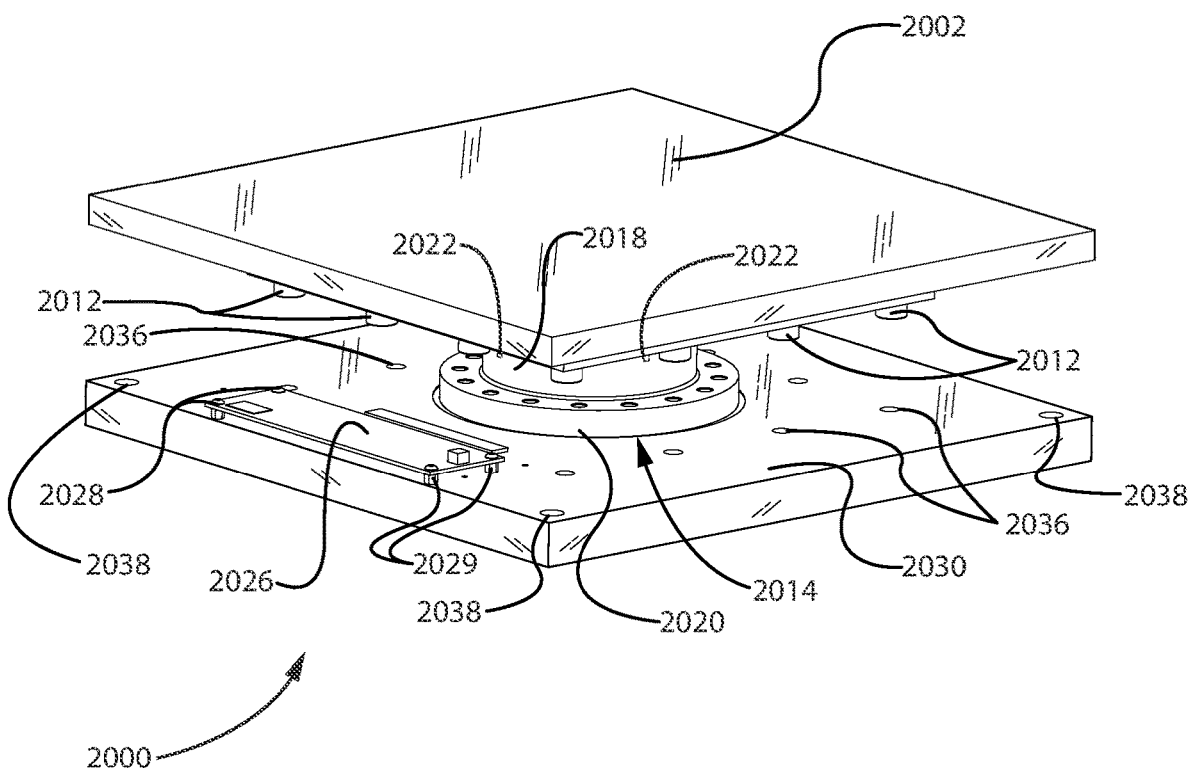
FIG. 24 is an assembled perspective view of a force measurement assembly, according to still a further embodiment of the invention.

A second illustrative arrangement 1960 of force measurement assemblies 1900 will be described with reference to FIG. 23. In the illustrative arrangement 1960 of FIG. 23, a plurality of independently displaceable force measurement assemblies 1900 are arranged in a matrix configuration (e.g., a 6×6 matrix containing a total of thirty-six (36) independently displaceable force measurement assemblies 1900). The force measurement assemblies 1900 of the matrix configuration 1960 in FIG. 23 can be displaced in a manner similar to that described above for the arrangement of FIGS. 19-22.

In the force measurement systems of FIGS. 19-22 described above, there is no physical connection between individual ones of the plurality of force measurement assemblies 1900, 1900a, 1900b, 1900c, 1900d, 1900e, 1900f such that the individual ones of the plurality of force measurement assemblies 1900, 1900a, 1900b, 1900c, 1900d, 1900e, 1900f are capable of being independently displaced along virtually any path on a support surface. Because the plurality of force measurement assemblies 1900, 1900a, 1900b, 1900c, 1900d, 1900e, 1900f are independently displaceable while a subject is walking or running on the force measurement assemblies 1900, 1900a, 1900b, 1900c, 1900d, 1900e, 1900f, a small footprint of force measurement assemblies 1900, 1900a, 1900b, 1900c, 1900d, 1900e, 1900f can advantageously be used.

Also, in the force measurement systems of FIGS. 19-22 described above, a gap is provided between each of the force measurement assemblies 1900, 1900a, 1900b, 1900c, 1900d, 1900e, 1900f so as to prevent interaction between adjacent ones of the plurality of force measurement assemblies 1900, 1900a, 1900b, 1900c, 1900d, 1900e, 1900f. The top surfaces of each of the plurality of force measurement assemblies 1900, 1900a, 1900b, 1900c, 1900d, 1900e, 1900f remain upwardly facing when the plurality of force measurement assemblies 1900, 1900a, 1900b, 1900c, 1900d, 1900e, 1900f are being independently displaced. Also, when plurality of force measurement assemblies 1900, 1900a, 1900b, 1900c, 1900d, 1900e, 1900f are being independently displaced, the top surface of each of the plurality of force measurement assemblies 1900, 1900a, 1900b, 1900c, 1900d, 1900e, 1900f remains generally parallel to the top surfaces of the other ones of the plurality of force measurement assemblies 1900, 1900a, 1900b, 1900c, 1900d, 1900e, 1900f.

FIGS. 24-27 illustrate a force measurement assembly 2000 according to a further embodiment of the present invention. As will be described in further detail hereinafter, in the illustrative embodiment, the force measurement assembly 2000 of FIGS. 24-27 may be provided as part of a force plate array with a plurality of force plate assemblies (see FIGS. 28-31). As shown in FIGS. 24-27, the force measurement assembly 2000 comprises a single force transducer 2014 supporting the top component 2002. As such, in this illustrative embodiment, the single force transducer 2014 supports the entire weight of the top component 2002 and there are no other force transducers disposed underneath the top component 2002. In the illustrative embodiment, the single force transducer 2014 is disposed proximate to a center of the top component 2002. In order to support the entire weight of the top component 2002 and the subject disposed thereon during the use of the force measurement assembly 2000, the single force transducer 2014 may have an outer diameter than is between approximately one-third and approximately one-half the width dimension of the top component 2002. Similar to the force measurement assemblies described above, the force measurement assembly 2000 illustrated in FIGS. 24-27 is configured to receive a user/subject thereon, and is capable of measuring the forces and/or moments applied to its measurement surface by the user/subject.

Figure 25:
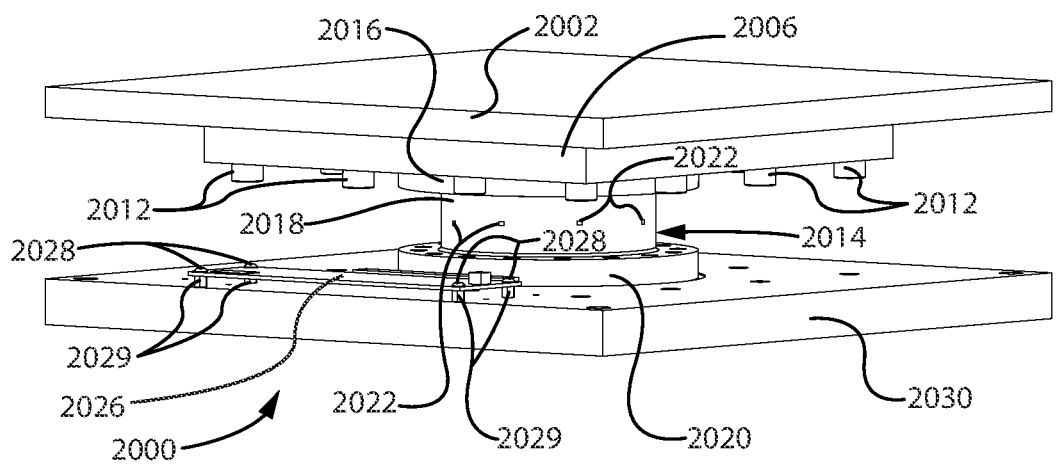
FIG. 25 is another assembled perspective view of the force measurement assembly of FIG. 24.
Figure 26:
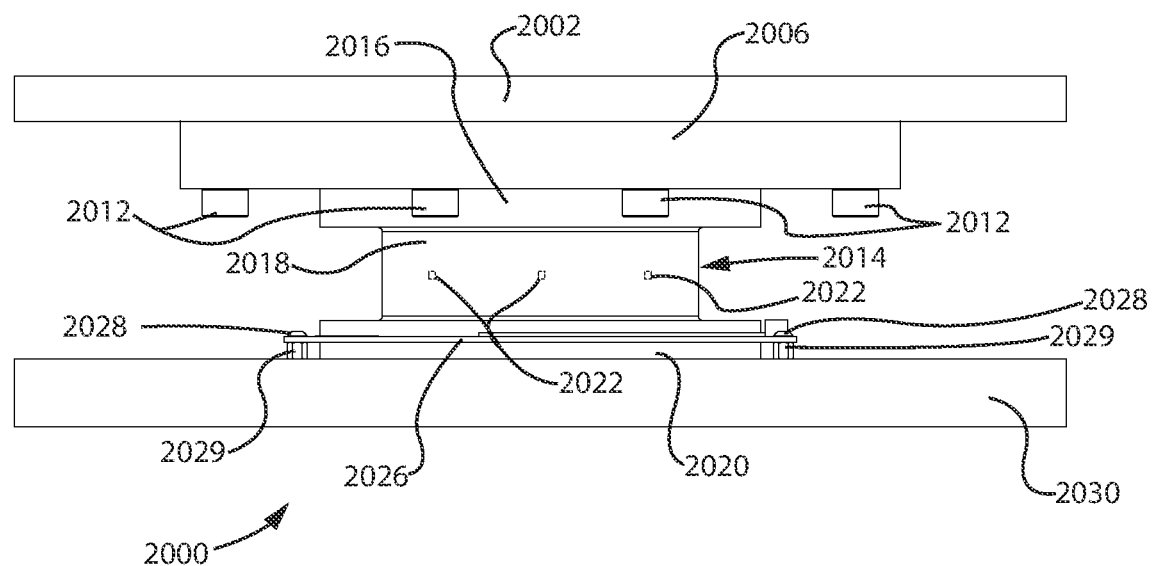
FIG. 26 is a side elevational view of the force measurement assembly of FIG. 24.

Referring again to FIGS. 24-27, it can be seen that the force measurement assembly 2000 of the illustrative embodiment is in the form of a force plate assembly with a top measurement surface. The force plate assembly includes a top plate 2002 supported on the single pylon-type load transducer 2014. In the illustrative embodiment, as shown in FIGS. 25 and 26, the single pylon-type load transducer 2014 may be mounted to the underside of the top plate 2002 by means of a top adapter plate 2006. In particular, with combined reference to FIGS. 24-27, it can be seen that the top adapter plate 2006 may be secured to the underside of the top plate 2002 by a plurality of fastener members 2012 (e.g., a plurality of machine screws) that are received within respective apertures 2010 in the top adapter plate 2006.

Figure 27:
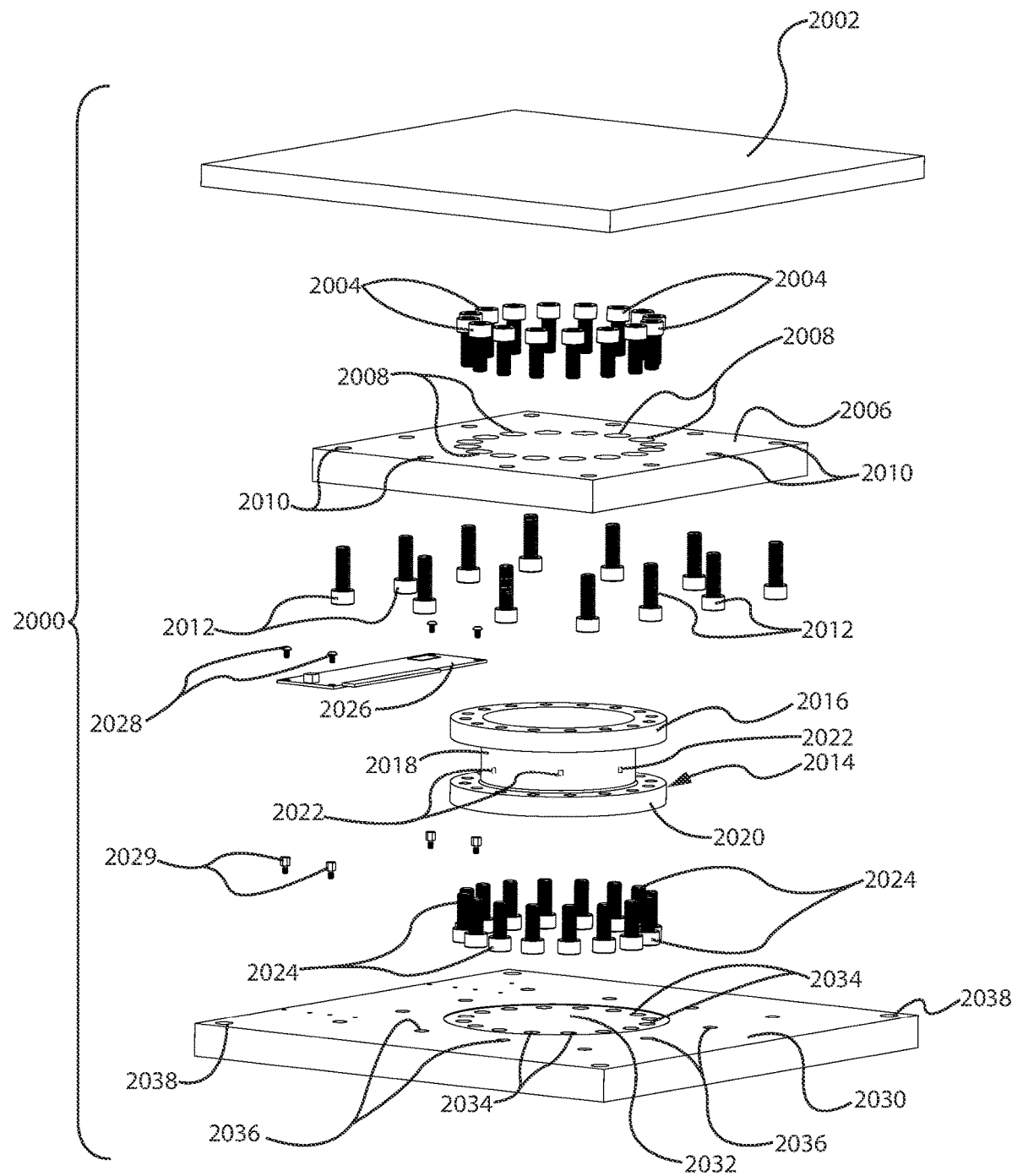
FIG. 27 is an exploded perspective view of the force measurement assembly of FIG. 24.

In the illustrative embodiment of FIGS. 24-27, the force measurement assembly 2000 comprises the single pylon-type load transducer 2014. The load transducer 2014 generally includes a one-piece compact transducer frame portion having a central cylindrical body portion 2018 and a pair of flanges 2016, 2020 disposed at opposite longitudinal ends of the central cylindrical body portion 2018. In particular, the load transducer 2014 includes a bottom flange 2020 disposed at the lower longitudinal end of the cylindrical body portion 2018, and a top flange 2016 disposed at the upper longitudinal end of the cylindrical body portion 2018. As best illustrated in the exploded perspective view of FIG. 27, the bottom flange 2020 comprises a plurality of circumferentially spaced-apart mounting apertures disposed therethrough. Each of the mounting apertures is configured to receive a respective fastener 2024 (e.g., a threaded screw or bolt) for securing the load transducer 2014 to the bottom base plate 2030. In the bottom base plate 2030, each of the fasteners 2024 is received in a respective fastener aperture 2034. As shown in FIG. 27, in the illustrative embodiment, the top surface of the bottom base plate 2030 is provided with a slight circular recess 2032 in the center thereof for receiving the bottom portion of the bottom flange 2020 of the load transducer 2014, which enables the load transducer 2014 to be essentially self-aligned on the bottom base plate 2030. Similarly, as shown in FIG. 27, the top flange 2016 also comprises a plurality of circumferentially spaced-apart mounting apertures disposed therethrough. Each of the mounting apertures is configured to receive a respective fastener 2004 (e.g., a threaded screw or bolt) for securing the load transducer 2014 to the top adapter plate 2006. In the top adapter plate 2006, each of the fasteners 2004 is received in a respective fastener aperture 2008. Similar to the circular recess 2032 in the bottom base plate 2030, the bottom surface of the top adapter plate 2006 may be provided with a slight circular recess in the center thereof for receiving the top portion of the top flange 2016 of the load transducer 2014, which would enable the load transducer 2014 also to be essentially self-aligned on the top adapter plate 2006 as well. The frame portion of the pylon-type load transducer 2014 is preferably machined in one piece from aluminum, titanium, steel, or any other suitable material that meets strength and weight requirements.

In the illustrative embodiment, with reference again to FIGS. 24 and 27, it can be seen that the bottom base plate 2030 may be provided with a first plurality of mounting apertures 2036 disposed around the circular recess 2032 for receiving respective fasteners for securing the force measurement assembly 2000 to a support surface (e.g., a floor of a building). The first plurality of mounting apertures 2036 are located between the peripheral edge of the bottom base plate 2030 and the circular recess 2032. In addition, as further shown in FIGS. 24 and 27, the bottom base plate 2030 may be provided with a second plurality of mounting apertures 2038 disposed in respective corners of the base plate 2030 for receiving respective fasteners for securing the force measurement assembly 2000 to the support surface (e.g., a floor of a building).

Referring collectively to FIGS. 25-27, it can be seen that a plurality of deformation sensing elements (e.g., strain gages 2022) are disposed on the outer periphery of the central cylindrical body portion 2018 of the load transducer 2014. In particular, in the illustrative embodiment, a first subset of the strain gages 2022 (see FIG. 27) is sensitive to a first force component (i.e., the z-component of the force, $F_Z$, which is the vertical force) of the load and the outputs one or more first output signals representative of the first force component ($F_Z$). A second subset of the strain gages 2022 (see FIG. 27) is sensitive to one or more second force components (i.e., the x-component or y-component of the force, $F_X$, $F_Y$, which are the shear forces) of the load and the outputs one or more second output signals representative of the one or more second force components ($F_X$, $F_Y$). In the illustrative embodiment, the load transducer 2014 may be a six-component load transducer that measures all three (3) orthogonal components of the resultant forces and moments acting on the top plate component 2002 of the force measurement assembly 2000 (i.e., $F_X$, $F_Y$, $F_Z$, $M_X$, $M_Y$, $M_Z$). The entire load applied to the top plate component 2002 of the load transducer 2014 is conveyed through the central cylindrical body portion 2018 such that the resulting deformation of the cylindrical body portion 2018 detected by the strain gages 2022 is indicative of the applied load to the top plate component 2002.

Referring again to FIGS. 24-27, it can be seen that the force measurement assembly 2000 further includes a printed circuit board (PCB) assembly 2026 for digitizing and conditioning the force output signal from the load transducer 2014. The printed circuit board assembly 2026 may include one or more Universal Serial Bus (USB) ports for operatively coupling the force measurement assembly 2000 to an external computing device (i.e., an electrical cable connected to the computing device may have a USB plug that is inserted into one of the USB ports of the printed circuit board assembly 2026). As shown in FIGS. 24-27, the printed circuit board assembly 2026 may be secured to the bottom base plate 2030 of the force measurement assembly 2000 by means of securement screws 2028 and threaded standoffs 2029. The threaded standoffs 2029 elevate the printed circuit board assembly 2026 slightly above the top surface of the bottom base plate 2030, and the securement screws 2028 fasten the printed circuit board assembly 2026 to the threaded standoffs 2029. In the illustrative embodiment, the threaded standoffs 2029 are secured into the top surface of the bottom base plate 2030. In one or more embodiments, the printed circuit board assembly 2026 also may compute the output forces, the output moments, and/or the center of pressure, and then the external computing device may perform the remainder of the computations that use the output forces, the output moments, and/or the center of pressure from the force measurement assembly 2000.

In an alternative embodiment, the single load transducer of the force measurement assembly 2000 may be in the form of a force transducer beam, rather than a pylon-type load transducer 2014.

In the illustrative embodiment, the top plate component 2002, the top adapter plate 2006, and the bottom base plate 2030 may be formed from aluminum or another suitable material.

Figure 28:
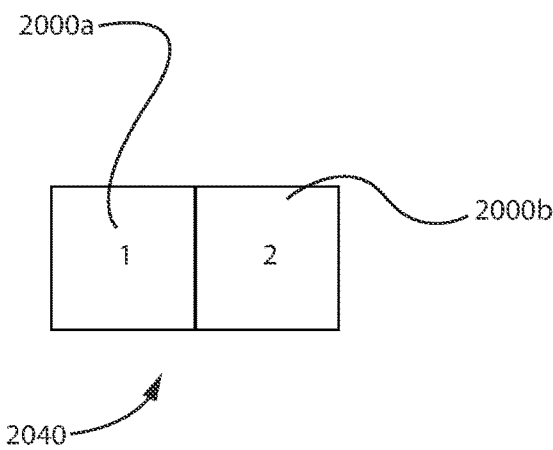
FIG. 28 is a top plan view illustrating two (2) of the force measurement assemblies of FIG. 24 arranged in a first configuration.
Figure 29:
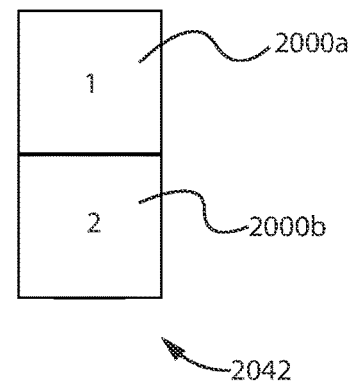
FIG. 29 is a top plan view illustrating two (2) of the force measurement assemblies of FIG. 24 arranged in a second configuration.
Figure 30:
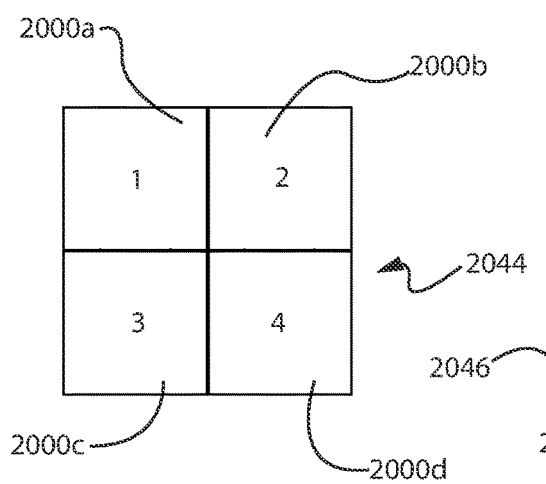
FIG. 30 is a top plan view illustrating four (4) of the force measurement assemblies of FIG. 24 arranged in a third configuration.
Figure 31:
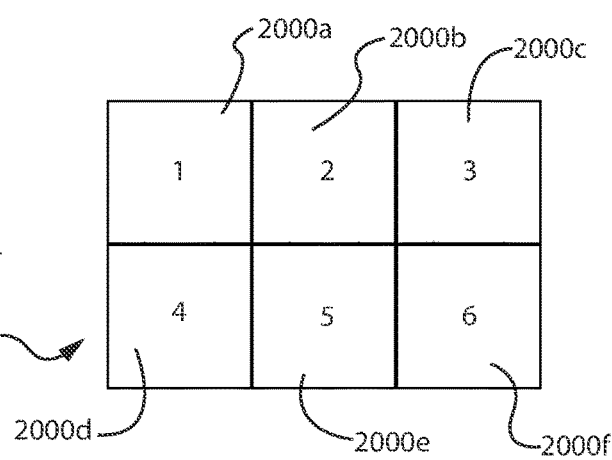
FIG. 31 is a top plan view illustrating six (6) of the force measurement assemblies of FIG. 24 arranged in a fourth configuration.

In the illustrative embodiment, a plurality of force measurement assemblies 2000 are designed to be combined in an array or matrix configuration. For example, a first illustrative arrangement 2040 of force measurement assemblies 2000 is depicted in FIG. 28. In the illustrative arrangement 2040 of FIG. 28, two (2) force measurement assemblies 2000a, 2000b are arranged in a horizontal configuration (e.g., a 1×2 matrix). As another example, a second illustrative arrangement 2042 of force measurement assemblies 2000 is depicted in FIG. 29. In the illustrative arrangement 2042 of FIG. 29, two (2) force measurement assemblies 2000a, 2000b are arranged in a vertical configuration (e.g., a 2×1 matrix). As yet another example, a third illustrative arrangement 2044 of force measurement assemblies 2000 is depicted in FIG. 30. In the illustrative arrangement 2044 of FIG. 30, four (4) force measurement assemblies 2000a, 2000b, 2000c, 2000d are arranged in a square matrix configuration (e.g., a 2×2 matrix). As still another example, a fourth illustrative arrangement 2046 of force measurement assemblies 2000 is depicted in FIG. 31. In the illustrative arrangement 2046 of FIG. 31, six (6) force measurement assemblies 2000a, 2000b, 2000c, 2000d, 2000e, 2000f are arranged in a rectangular matrix configuration (e.g., a 2×3 matrix).

Figure 32:
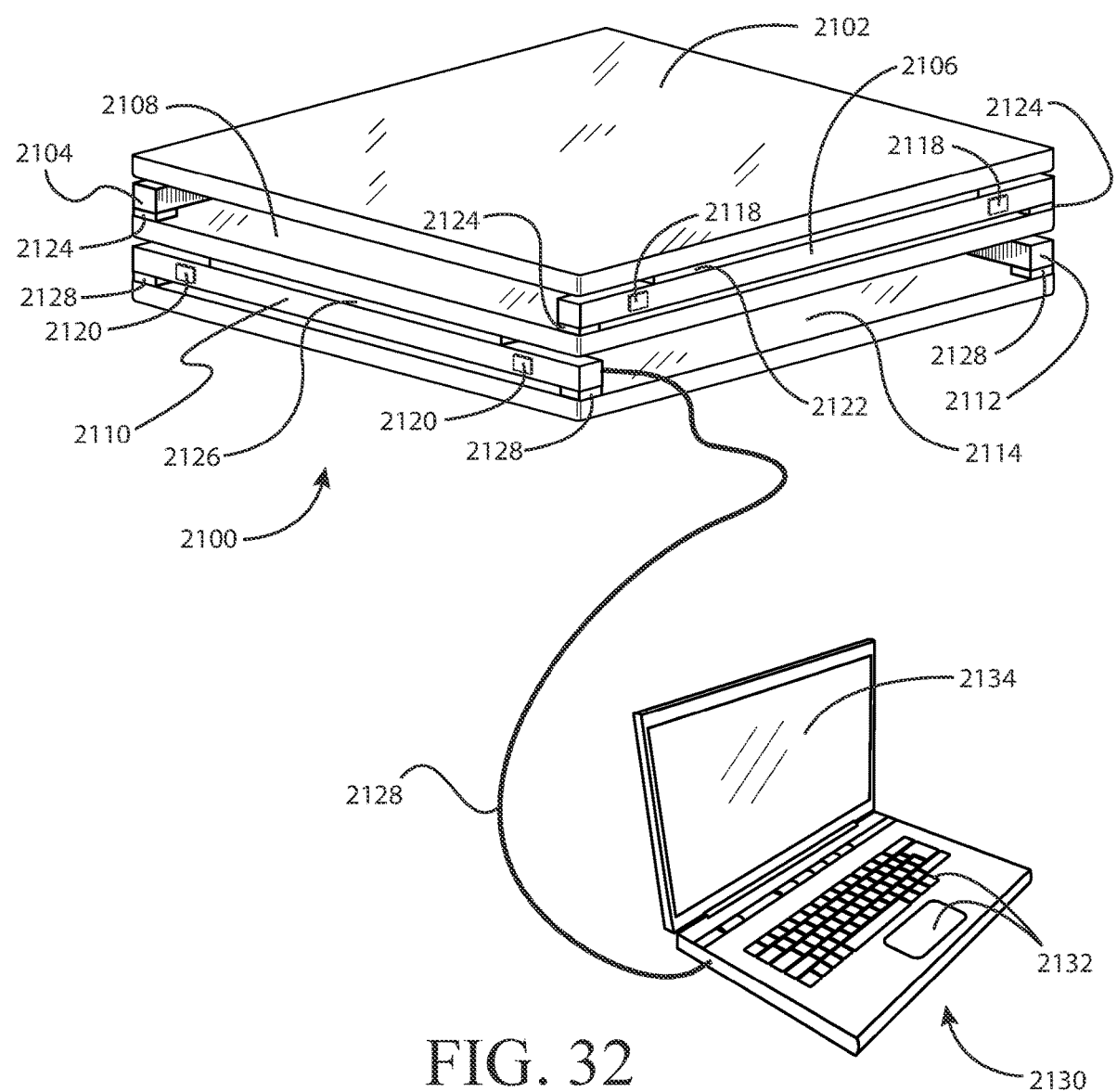
FIG. 32 is an assembled perspective view of a force measurement system, according to yet a further embodiment of the invention.
Figure 33:
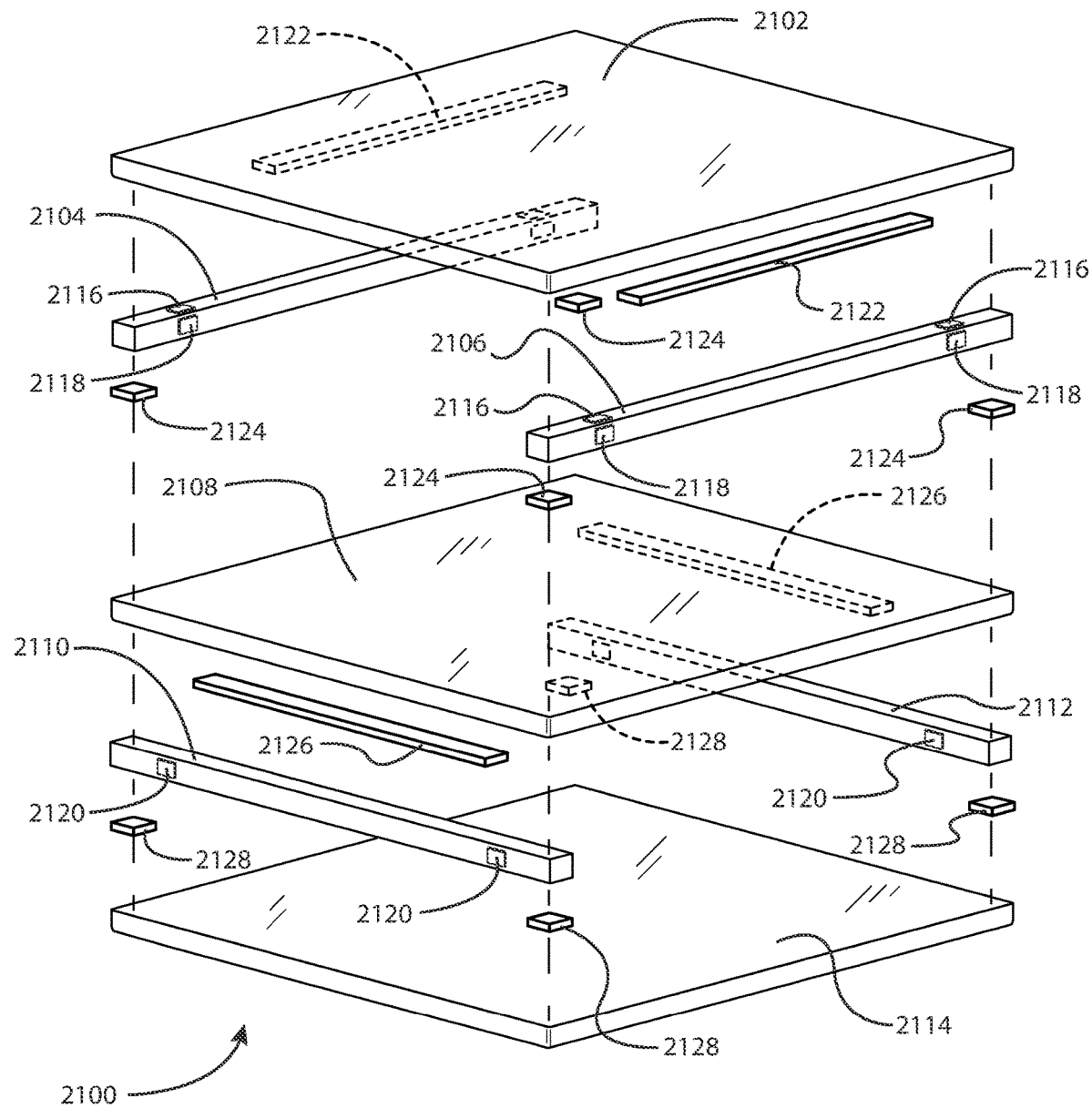
FIG. 33 is an exploded perspective view of the force measurement assembly of FIG. 32.

FIGS. 32 and 33 illustrate a force measurement assembly 2100 according to yet a further embodiment of the present invention. In the illustrative embodiment, the force measurement assembly 2100 of FIGS. 32 and 33 may be provided as part of a force measurement system 2140, and thus may be operatively coupled to a data acquisition/data processing device (e.g., a data acquisition/data processing device 2130 in a form of a laptop computing device shown in FIG. 32, and diagrammatically depicted in FIG. 34). Like the force measurement assembly 1800 described above, the force measurement assembly 2100 illustrated in FIGS. 32 and 33 is configured to receive a user/subject thereon, and is capable of measuring the forces and/or moments applied to its measurement surface by the user/subject.

Referring again to FIGS. 32 and 33, it can be seen that the force measurement assembly 2100 of the illustrated embodiment is in the form of a force plate assembly with a top measurement surface. The force plate assembly includes a top plate 2102 supported on a plurality of load transducer beams 2104, 2106, 2110, 2112. The top plate 2102 is configured to receive at least one portion of a body of a user (e.g., the legs of a user). In the illustrated embodiment, the force plate assembly further includes a bottom base plate 2114 disposed underneath the plurality of load transducer beams 2104, 2106, 2110, 2112. In the illustrated embodiment, each load transducer beam 2110, 2112 may be mounted to the upper surface of the bottom base plate 2114 by spacer plates 2128 disposed at the ends of each load transducer beam 2110, 2112. In the illustrated embodiment, the top plate 2102 and the bottom base plate 2114 may be formed from aluminum or another suitable metallic material.

In the illustrated embodiment of FIGS. 32 and 33, the force measurement assembly 2100 comprises the first pair of spaced-apart load transducer beams 2104, 2106 that are disposed underneath, and near each of the respective sides of the top plate component 2102. In the illustrated embodiment, each load transducer beam 2104, 2106 may be mounted to the underside of the top plate component 2102 by a respective spacer plate 2122. The force measurement assembly 2100 further comprises the second pair of spaced-apart load transducer beams 2110, 2112 that are disposed underneath, and near the ends of the load transducer beams 2104, 2106. In the illustrative embodiment of FIGS. 32 and 33, each of the force transducer beams 2104, 2106, 2110, 2112 is generally in the form of a linear force transducer beam with load cells disposed at the opposite ends of the beam 2104, 2106, 2110, 2112. In the illustrated embodiment, the frame portion of each load transducer 2104, 2106, 2110, 2112 is milled as one solid and continuous piece of a single material. That is, the frame portion of each load transducer beam 2104, 2106, 2110, 2112 is of unitary or one-piece construction. The frame portion of each load transducer beam 2104, 2106, 2110, 2112 is preferably machined in one piece from aluminum, titanium, steel, or any other suitable material that meets strength and weight requirements.

In the illustrated embodiment of FIGS. 32 and 33, the spaced-apart load transducer beams 2104, 2106 are disposed generally perpendicular relative to the spaced-apart load transducer beams 2110, 2112. Also, in the illustrated embodiment of FIGS. 32 and 33, the spaced-apart load transducer beams 2104, 2106 are supported on the spaced-apart second load transducer beams 2110, 2112.

Referring again to FIGS. 32 and 33, in the illustrated embodiment, it can be seen that the force measurement assembly 2100 may further comprise an intermediate plate 2108 disposed between the first pair of spaced-apart load transducer beams 2104, 2106 and the second pair of spaced-apart load transducer beams 2110, 2112, the pair of spaced-apart first load transducer 2104, 2106 beams being supported on the intermediate plate 2108, and the pair of spaced-apart load transducer beams 2110, 2112 being disposed underneath the intermediate plate 2108. In the illustrated embodiment, each load transducer beam 2104, 2106 may be mounted to the upper surface of the intermediate plate 2108 by spacer plates 2124 disposed at the ends of each load transducer beam 2104, 2106. Also, in the illustrated embodiment, each load transducer beam 2110, 2112 may be mounted to the underside of the intermediate plate 2108 by a respective spacer plate 2126. In the illustrated embodiment, the spacer plates 2122, 2124, 2126, 2128 ensure that the total load applied to the plate component 2102 is transmitted through the load cells of the load transducer beams 2104, 2106, 2110, 2112. As an alternative to the spacer plates 2122, 2124, 2126, 2128, the load transducer beams 2104, 2106, 2110, 2112 could be provided with raised portions or standoff portions, as described above for the force transducer beams 1732 in the embodiment of FIG. 4.

In an alternative embodiment, rather than the force measurement assembly 2100 being provided with the intermediate plate 2108, the first pair of spaced-apart load transducer beams 2104, 2106 may be directly supported on the second pair of spaced-apart load transducer beams 2110, 2112.

Also, as best shown in the exploded view of FIG. 33, it can be seen that a plurality of deformation sensing elements (e.g., strain gages 2116, 2118, 2120) are disposed on the outer surfaces of the frame portions of the load transducer beams 2104, 2106, 2110, 2112. In particular, in the illustrative embodiment, the strain gages 2116 disposed on the top surfaces of the load transducer beams 2104, 2106 (see FIG. 33) are sensitive to a first force component (i.e., the z-component of the force, $F_Z$) of the load and output one or more first output signals representative of the first force component ($F_Z$) or vertical force ($F_Z$). Also, in the illustrative embodiment, the strain gages 2120 disposed on the side surfaces of the load transducer beams 2110, 2112 (see FIG. 33) are sensitive to a second force component (i.e., the y-component of the force, $F_Y$) of the load and output one or more second output signals representative of the second force component ($F_Y$) or shear force ($F_Y$) in a fore/aft direction. In addition, in the illustrative embodiment, the strain gages 2118 disposed on the side surfaces of the load transducer beams 2104, 2106 (see FIG. 33) are sensitive to a third force component (i.e., the x-component of the force, $F_X$) of the load and output one or more second output signals representative of the third force component ($F_X$) or shear force ($F_X$) in a lateral direction. In the illustrative embodiment, the side surfaces of the load transducer beams 2104, 2106 on which the strain gages 2118 are disposed are perpendicular or generally perpendicular to the top surfaces of the load transducer beams 2104, 2106 on which the strain gages 2116 are disposed.

Figure 34:
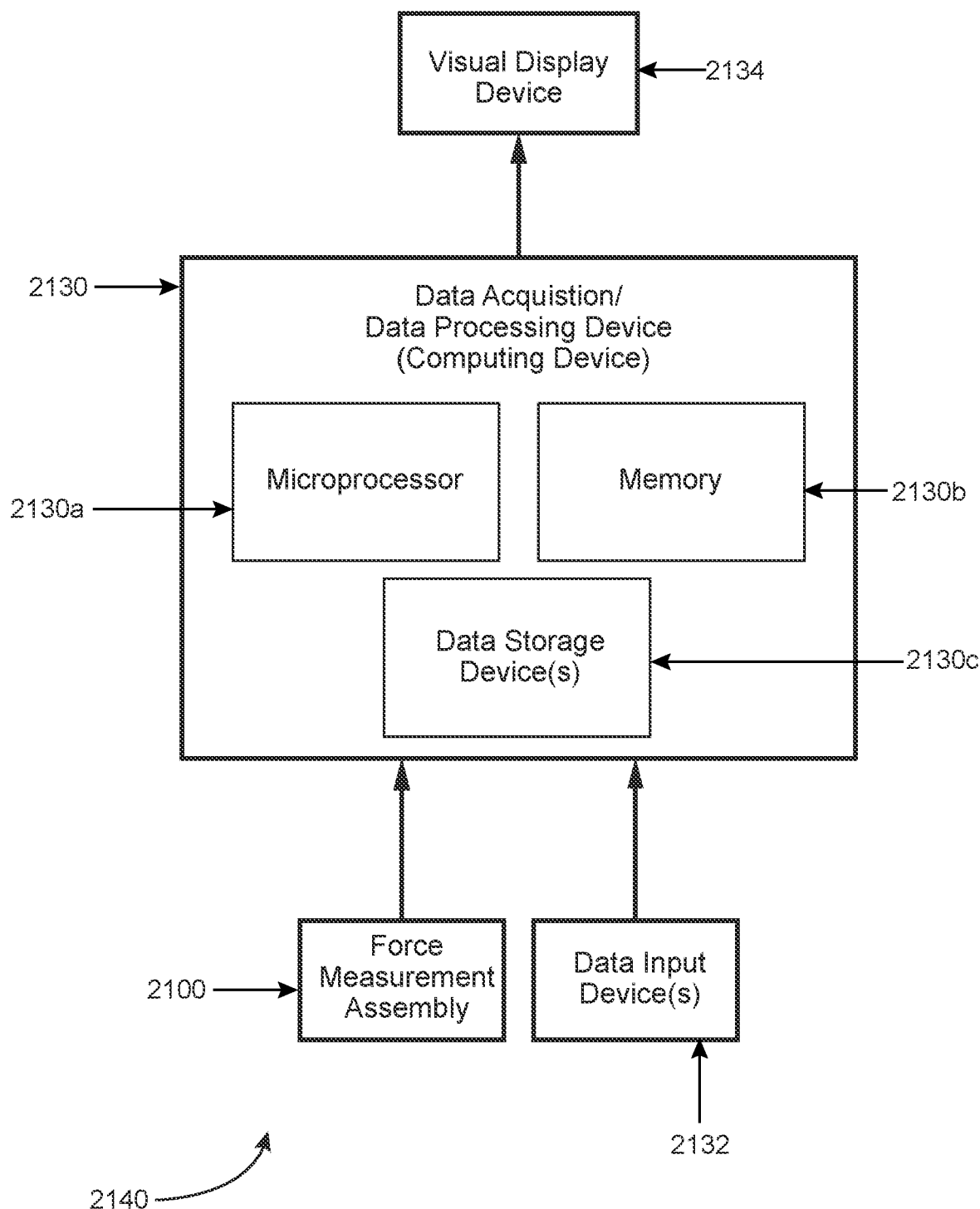
FIG. 34 is a block diagram of constituent components of the force measurement system of FIG. 32.

In the illustrated embodiment of FIGS. 32-34, the data acquisition/data processing device 2130 is operatively coupled to the first plurality of deformation sensing elements (e.g., strain gages 2116) of the load transducer beams 2104, 2106, the second plurality of deformation sensing elements (e.g., strain gages 2120) of the load transducer beams 2110, 2112, and the third plurality of deformation sensing elements (e.g., strain gages 2118) of the load transducer beams 2104, 2106, the data acquisition/data processing device 2130 is configured to receive the first, second, and third output signals from the deformation sensing elements 2116, 2118, 2120 of the load transducer beams 2104, 2106, 2110, 2112, and the data acquisition/data processing device 2130 is further configured to determine a first output force ($F_Z$) from the first output signal, a second output force ($F_Y$) from the second output signal, and a third output force ($F_X$) from the third output signal.

Now, turning to FIG. 34, it can be seen that the data acquisition/data processing device 2130 (i.e., the laptop computing device) of the force measurement system 2140 comprises a microprocessor 2130a for processing data, memory 2130b (e.g., random access memory or RAM) for storing data during the processing thereof, and data storage device(s) 2130c, such as one or more hard drives, compact disk drives, floppy disk drives, flash drives, or any combination thereof. As shown in FIG. 34, the force measurement assembly 2100 and the visual display device 2134 are operatively coupled to the core components 2130a, 2130b, 2130c of the data acquisition/data processing device 2130 such that data is capable of being transferred between these devices 2100, 2130a, 2130b, 2130c, and 2134. Also, as illustrated in FIG. 34, a plurality of data input devices 2132, such as the keyboard and mouse shown in FIG. 34, are operatively coupled to the core components 2130a, 2130b, 2130c of the data acquisition/data processing device 2130 so that a user is able to enter data into the data acquisition/data processing device 2130. In some embodiments, the data acquisition/data processing device 2130 can be in the form of a laptop computer, while in other embodiments, the data acquisition/data processing device 2130 can be embodied as a desktop computer.

Next, the acquisition and processing of the load data carried out by the exemplary force measurement system 2140 of FIGS. 32-34 will be described. Initially, a load is applied to the force measurement assembly 2100 (e.g., by a subject disposed thereon). The load is transmitted from the top plate component 2102 to the load transducer beams 2104, 2106, 2110, 2112 disposed underneath the top plate component 2102. As described above, in the illustrated embodiment, the load transducer beams 2104, 2106, 2110, 2112 include a plurality of strain gages 2116, 2118, 2120 wired in one or more Wheatstone bridge configurations, wherein the electrical resistance of each strain gage is altered when the associated beam portion of the load transducer beam 2104, 2106, 2110, 2112 undergoes deformation resulting from the load (i.e., forces and/or moments) acting on the plate component 2102. For each plurality of strain gages disposed on the load transducer beams 2104, 2106, 2110, 2112, the change in the electrical resistance of the strain gages brings about a consequential change in the output voltage of the Wheatstone bridge (i.e., a quantity representative of the load being applied to the measurement surface). Thus, in one embodiment, the four (4) load transducer beams 2104, 2106, 2110, 2112 disposed under the plate component 2102 output a total of twelve (12) analog output voltages (signals). In some embodiments, the twelve (12) analog output voltages from load transducer beams 2104, 2106, 2110, 2112 disposed under the plate component 2102 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 2100 transmits the force plate output signals $S_{FPO1}$-$S_{FP12}$ to a main signal amplifier/converter. Depending on whether the preamplifier board also includes an analog-to-digital (A/D) converter, the force plate output signals $S_{FPO1}$-$S_{FP12}$ could be either in the form of analog signals or digital signals. The main signal amplifier/converter further magnifies the force plate output signals $S_{FPO1}$-$S_{FP12}$, and if the signals $S_{FPO1}$-$S_{FP12}$ are of the analog-type (for a case where the preamplifier board did not include an analog-to-digital (A/D) converter), it may also convert the analog signals to digital signals. Then, the signal amplifier/converter may transform the digital signals into output load values by multiplying the voltage signals $S_{ACO1}$-$S_{AC12}$ by a calibration matrix. Alternatively, the signal amplifier/converter may transmit either the digital or analog signals $S_{ACO1}$-$S_{AC12}$ to the data acquisition/data processing device 2130 (computer 2130) so that the forces and/or moments that are being applied to the measurement surface of the force measurement assembly 2100 can be transformed into the output load values. In addition to the components 2130a, 2130b, 2130c, the data acquisition/data processing device 2130 may further comprise an analog-to-digital (A/D) converter if the signals $S_{ACO1}$-$S_{AC12}$ are in the form of analog signals. In such a case, the analog-to-digital converter will convert the analog signals into digital signals for processing by the microprocessor 2130a.

When the data acquisition/data processing device 2130 receives the voltage signals $S_{ACO1}$-$S_{AC12}$, it initially transforms the signals into output forces by multiplying the voltage signals $S_{ACO1}$-$S_{AC12}$ by a calibration matrix. If the load transducer beams 2104, 2106, 2110, 2112 are also capable of determining applied moments, the data acquisition/data processing device 2130 may additionally transform the signals into output moments by multiplying the voltage signals by the calibration matrix. After which, the force exerted on the surface of the force measurement assembly 2100, and the center of pressure of the applied force (i.e., the x and y coordinates of the point of application of the force applied to the measurement surface) is determined by the data acquisition/data processing device 2130.

In one exemplary embodiment, the data acquisition/data processing device 2130 determines all three (3) orthogonal components of the resultant forces acting on the plate component 2102 of the force measurement assembly 2100 (i.e., $F_X$, $F_Y$, $F_Z$). In yet other embodiments of the invention, all three (3) orthogonal components of the resultant forces and moments acting on the plate component 2102 of the force measurement assembly 2100 (i.e., $F_X$, $F_Y$, $F_Z$, $M_X$, $M_Y$, $M_Z$) may be determined.

FIGS. 35-39 illustrate a force measurement assembly 2200 according to still a further embodiment of the present invention. In the illustrative embodiment, the force measurement assembly 2200 of FIGS. 35-39 may be provided as part of a force measurement system (see FIGS. 35 and 36), and thus may be operatively coupled to a data acquisition/data processing device (e.g., a data acquisition/data processing device 2208 in a form of a laptop computing device shown in FIGS. 35 and 36) via an electrical cable 2206. The internal hardware of the data acquisition/data processing device 2208 is the same as that diagrammatically depicted in FIG. 34 for data acquisition/data processing device 2130. Like the force measurement assemblies 1800 and 2100 described above, the force measurement assembly 2200 illustrated in FIGS. 35-39 is configured to receive a user/subject thereon, and is capable of measuring the forces and/or moments applied to its measurement surface by the user/subject.

Referring again to FIGS. 35-39, it can be seen that the force measurement assembly 2200 of the illustrated embodiment is in the form of a force plate assembly with a top measurement surface. The force plate assembly includes a top plate 2202 supported on a plurality of load transducers 2210 (e.g., four (4) load transducers 2210). The top plate 2202 is configured to receive at least one portion of a body of a user (e.g., the legs of a user). In the illustrated embodiment, the force plate assembly further includes a bottom base plate 2204 disposed underneath the plurality of load transducers 2210. In the illustrated embodiment, each load transducer 2210 may be mounted to the lower surface of the top plate 2202 by a plurality of fasteners (e.g., screws or bolts) through the fastener apertures 2218 in standoff block portion 2216 of each load transducer 2210. Also, in the illustrated embodiment, each load transducer 2210 may be mounted to the upper surface of the bottom base plate 2204 by a plurality of fasteners (e.g., screws or bolts) through the fastener apertures 2230, 2234 in standoff portions 2228, 2232 of each load transducer 2210. In the illustrated embodiment, the top plate 2202 and the bottom base plate 2204 may be formed from aluminum or another suitable metallic material.

In the illustrated embodiment of FIGS. 35-39, each of the plurality of load transducers 2210 of the force measurement assembly 2200 is diagonally arranged relative to a first coordinate axis 2240 (e.g., an x-axis) and a second coordinate axis 2242 (e.g., a y-axis). In the illustrated embodiment, the plurality of load transducers 2210 are circumferentially spaced apart from one another around a periphery of the bottom base plate 2204 (see FIG. 36). In the illustrative embodiment of FIGS. 35-39, each of the load transducers 2210 is generally in the form of a T-shaped load transducer. In the illustrated embodiment, the frame portion of each load transducer 2210 is milled as one solid and continuous piece of a single material. That is, the frame portion of each load transducer 2210 is of unitary or one-piece construction. The frame portion of each load transducer 2210 is preferably machined in one piece from aluminum, titanium, steel, or any other suitable material that meets strength and weight requirements.

Now, referring to the perspective view of FIGS. 40-43, it can be seen that each load transducer 2210 generally includes a one-piece compact transducer frame having a first transducer beam section 2212 and a second transducer beam section 2214. The first transducer beam section 2212 is connected to a middle portion of the second transducer beam section 2214, and the load transducer frame portion is configured to receive a load that is applied thereto. As best shown in the perspective views of FIGS. 40-43, in the illustrated embodiment, the first transducer beam section 2212 of the load transducer frame portion is disposed generally perpendicular or perpendicular to the second transducer beam section 2214. As best illustrated in the perspective views of FIGS. 40-43, the first transducer beam section 2212 of the load transducer 2210 comprises a plurality of load cells or transducer elements for measuring the various components of an applied force, while the second transducer beam section 2214 of the load transducer frame portion contains no load cells or transducer elements. That is, in the illustrated embodiment, the first transducer beam section 2212 is instrumented, while the second transducer beam section 2214 is not instrumented.

As shown in FIGS. 40-43, the illustrated transducer beam sections 2212, 2214 are arranged in a generally T-shaped or T-shaped configuration (i.e., the load transducer frame portion of the load transducer 2210 is generally T-shaped). In the illustrated embodiment, the first transducer beam section 2212 forms the stem portion of the T-shaped load transducer frame portion and the second transducer beam section 2214 forms the arm portion of the T-shaped load transducer frame portion.

Figure 40:
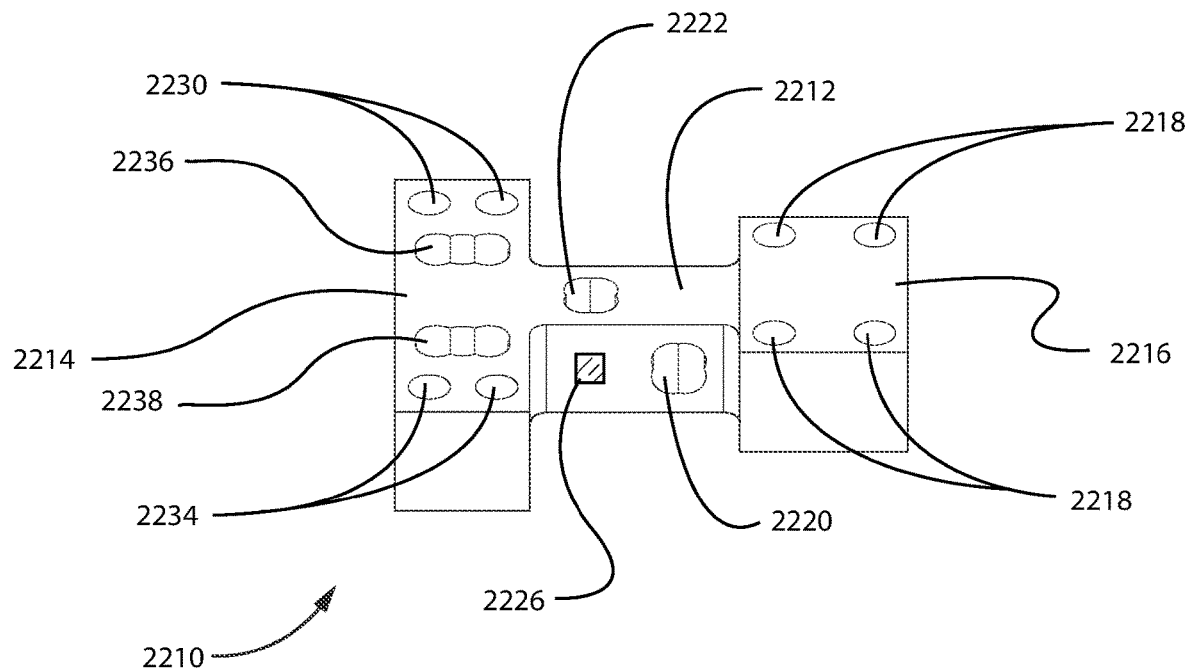
FIG. 40 is a top-side perspective view of the load transducer of the force measurement assembly of the force measurement system of FIG. 35.
Figure 41:
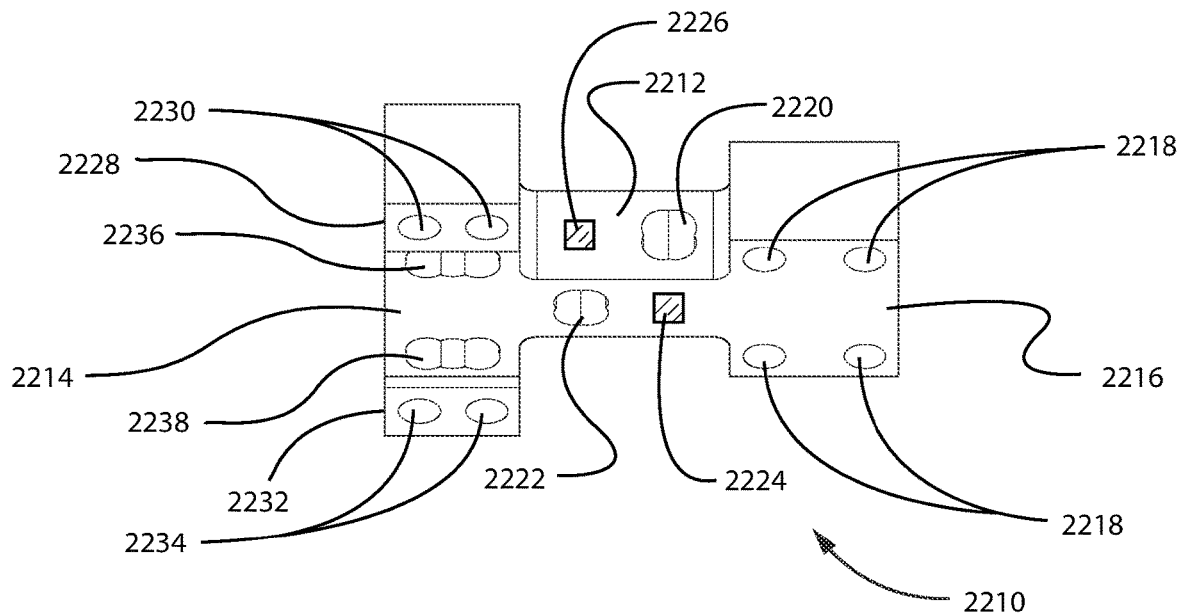
FIG. 41 is a bottom-side perspective view of the load transducer of the force measurement assembly of the force measurement system of FIG. 35.
Figure 42:
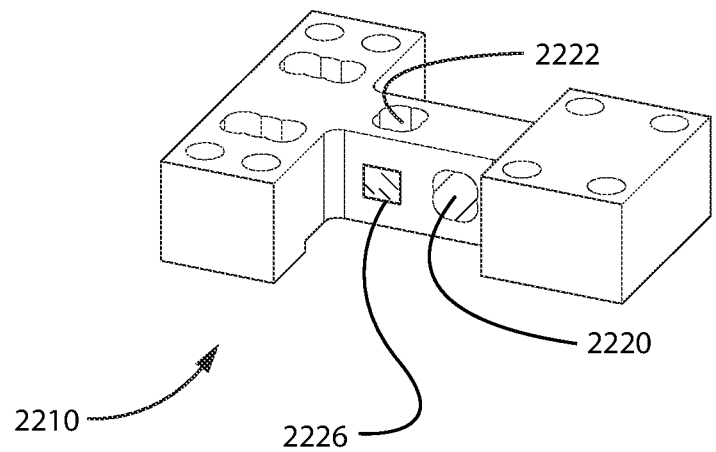
FIG. 42 is a top-side perspective view of the load transducer of the force measurement assembly of the force measurement system of FIG. 35.

In the illustrated embodiment of FIGS. 40-43, the first transducer beam section 2212 of each load transducer 2210 comprises load cells disposed on the beam section 2212. A first one of the load cells measures a vertical force (i.e., $F_Z$) exerted on the top plate component 2202 by the user, while a second one of the load cells measures a first shear force (i.e., $F_X$) and/or a second shear force (i.e., $F_Y$) exerted on the top plate component 2202 by the user. Also, as best shown in FIGS. 40 and 41, each of the load cells is provided with an aperture 2220, 2222 disposed through the beam section 2212. The apertures 2220, 2222 significantly increase the sensitivity of the load transducer beam section 2212 when a load is applied thereto by reducing the cross-sectional area of the load transducer beam section 2212 at the locations of the apertures 2220, 2222. Referring again to the illustrated embodiment of FIGS. 40-43, it can be seen that the end of the first transducer beam section 2212, which is opposite to the end of the beam section 2212 that is connected to the second transducer beam section 2214, is provided with a standoff block portion 2216 with a top surface that is disposed at a higher elevation than the top surface of the remainer of the load transducer 2210. Similarly, with reference again to the illustrated embodiment of FIGS. 40-43, it can be seen that the opposed ends of the second transducer beam section 2214 are provided with respective first and second standoffs 2228, 2232 with bottom surfaces that are disposed at lower elevations than the bottom surface of the remainder of the load transducer 2210. The standoff block portion 2216 and the first and second standoffs 2228, 2232 ensure that the total load applied to the plate component 2202 is transmitted through the load cells of the first transducer beam section 2212 of the load transducer 2210.

Referring again to the perspective views of FIG. 40-43, it can be seen that the second transducer beam section 2214 of the load transducer frame portion comprises third and fourth apertures 2236, 2238 disposed therein. Advantageously, the third and fourth apertures 2236, 2238 enhance the measurement sensitivity of the load transducer 2210 by increasing the flexing of the second transducer beam section 2214. In the illustrated embodiment, the second transducer beam section 2214 operates as a non-instrumented flexing element of the load transducer 2210 (i.e., the third and fourth apertures 2236, 2238 just provide sensitivity, but are not gaged).

As best shown in the perspective views of FIGS. 40-43, the illustrated load cells are located on the first transducer beam section 2212. In the illustrated embodiment, the load cells comprise deformation sensing elements in the form of strain gages 2224, 2226. Specifically, in the illustrated embodiment, the first transducer beam section 2212 of the load transducer 2210 comprises a strain gage 2224 disposed on the outer bottom surface thereof that is sensitive to a vertical force component (i.e., a $F_Z$ strain gage) and substantially centered on the aperture 2220. Turning again to FIGS. 40-43, in the illustrated embodiment, the first transducer beam section 2212 of the load transducer 2210 comprises a strain gage 2226 disposed on an outer side surface thereof that is sensitive to a first shear force component and/or a second shear force component (i.e., a $F_X$ and/or $F_Y$ strain gage) and substantially centered on the aperture 2222. In the illustrated embodiment, the first shear force component is generally perpendicular or perpendicular to the second shear force component, and each of the first and second shear force components are generally perpendicular or perpendicular to the vertical force component.

In the illustrated embodiment, the apertures 2220, 2222 have inner surfaces that are generally opposite or opposite to the respective outer bottom and side surfaces on which the strain gages 2224, 2226 are disposed.

Figure 43:
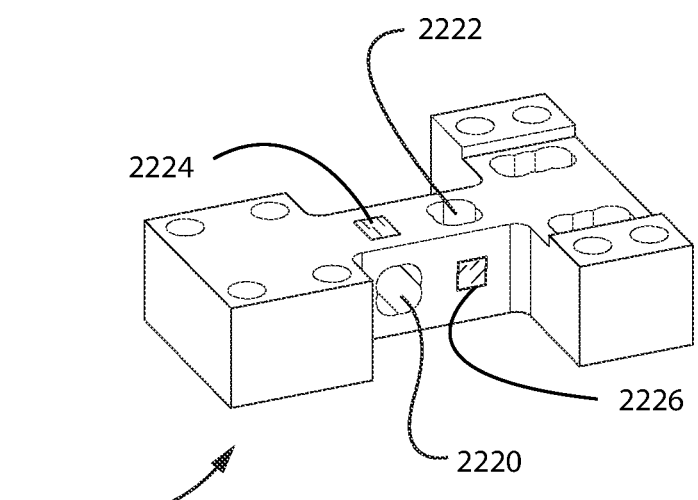
FIG. 43 is a side-bottom perspective view of the load transducer of the force measurement assembly of the force measurement system of FIG. 35.

As best shown in FIGS. 40-43, the illustrated load cells are mounted on the top or side surface of the first transducer beam section 2212 of the load transducer 2210 between the second transducer beam section 2214 and the standoff block portion 2216. Alternatively, the strain gage 2226 can be mounted to the opposite side surface of the first transducer beam section 2212, and the strain gage 2224 can be mounted to the top surface of the first transducer beam section 2212, rather than to the bottom of the first transducer beam section 2212 as illustrated in FIGS. 41 and 43. As force is applied to the ends of the first transducer beam section 2212, the first transducer beam section 2212 bends. This bending either stretches or compresses the strain gages 2224, 2226, which in turn changes the resistance of the electrical current passing therethrough. The amount of change in the electrical voltage or current is proportional to the magnitude of the applied force, as applied to the load transducer 2210.

In the illustrated embodiment, each of the strain gages 2224, 2226 comprises a half-bridge strain gage configuration wired in a Wheatstone bridge configuration for measuring the applied vertical and shear forces.

In the illustrated embodiment of FIGS. 35-39, the data acquisition/data processing device 2208 is operatively coupled to the plurality of deformation sensing elements (e.g., strain gages 2224, 2226) of the plurality of load transducers 2210. Also, the data acquisition/data processing device 2208 is configured to receive the first and second output signals from the plurality of deformation sensing elements 2224, 2226 of the plurality of load transducers 2210, and the data acquisition/data processing device 2208 is further configured to determine a first output force ($F_Z$) from the first output signals and a second output force ($F_X$) and/or a third output force ($F_Y$) from the second output signals.

In the illustrated embodiment, the first output force comprises a vertical output force ($F_Z$), the second output force comprises a first shear output force ($F_X$) in a first coordinate axis direction (e.g., a direction of x-axis 2240 in FIGS. 35, 36, and 39), and the third output force comprises a second shear output force ($F_Y$) in a second coordinate axis direction (e.g., a direction of y-axis 2242 in FIGS. 35, 36, and 39) that is perpendicular to the first coordinate axis direction (e.g., a direction of x-axis 2240 in FIGS. 35, 36, and 39) of the first shear output force ($F_X$). In the illustrated embodiment, the first shear output force ($F_X$) in the first coordinate axis direction (e.g., a direction of x-axis 2240 in FIGS. 35, 36, and 39) comprises a shear force in a lateral direction of the user, and the second shear output force ($F_Y$) in the second coordinate axis direction (e.g., a direction of y-axis 2242 in FIGS. 35, 36, and 39) comprises a shear force in a fore/aft direction of the user.

Figures 35, 36:
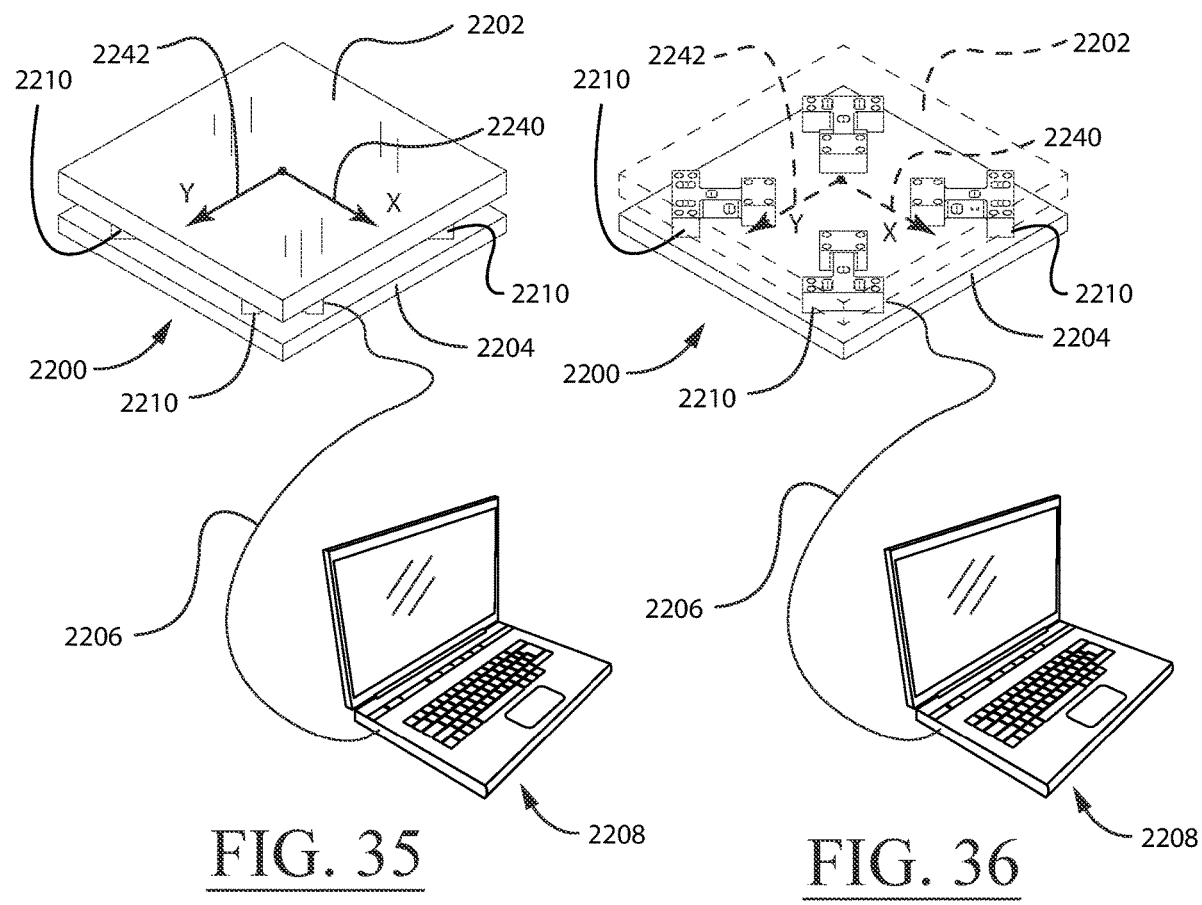
FIG. 35 is an assembled top-side perspective view of a force measurement system, according to still a further embodiment of the invention.
FIG. 36 is another assembled top-side perspective view of the force measurement system of FIG. 35, wherein the top plate of the force measurement assembly is shown in dashed lines.
Figure 37:
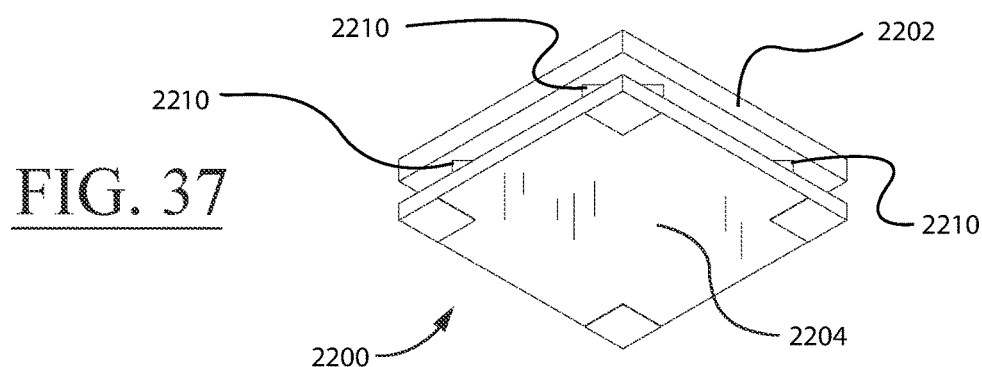
FIG. 37 is a bottom-side perspective view of the force measurement assembly of the force measurement system of FIG. 35.
Figure 38:
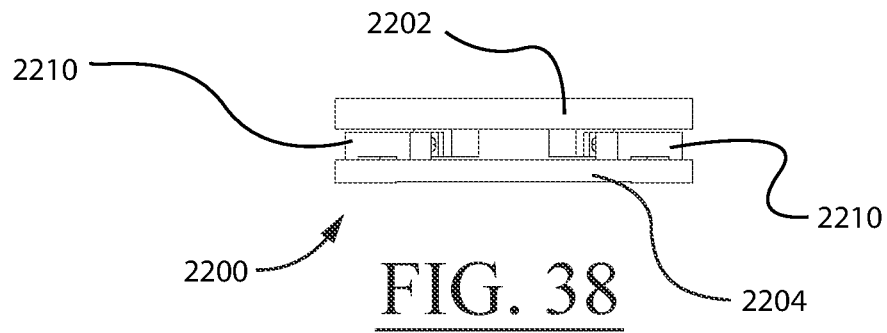
FIG. 38 is a side elevation view of the force measurement assembly of the force measurement system of FIG. 35.
Figure 39:
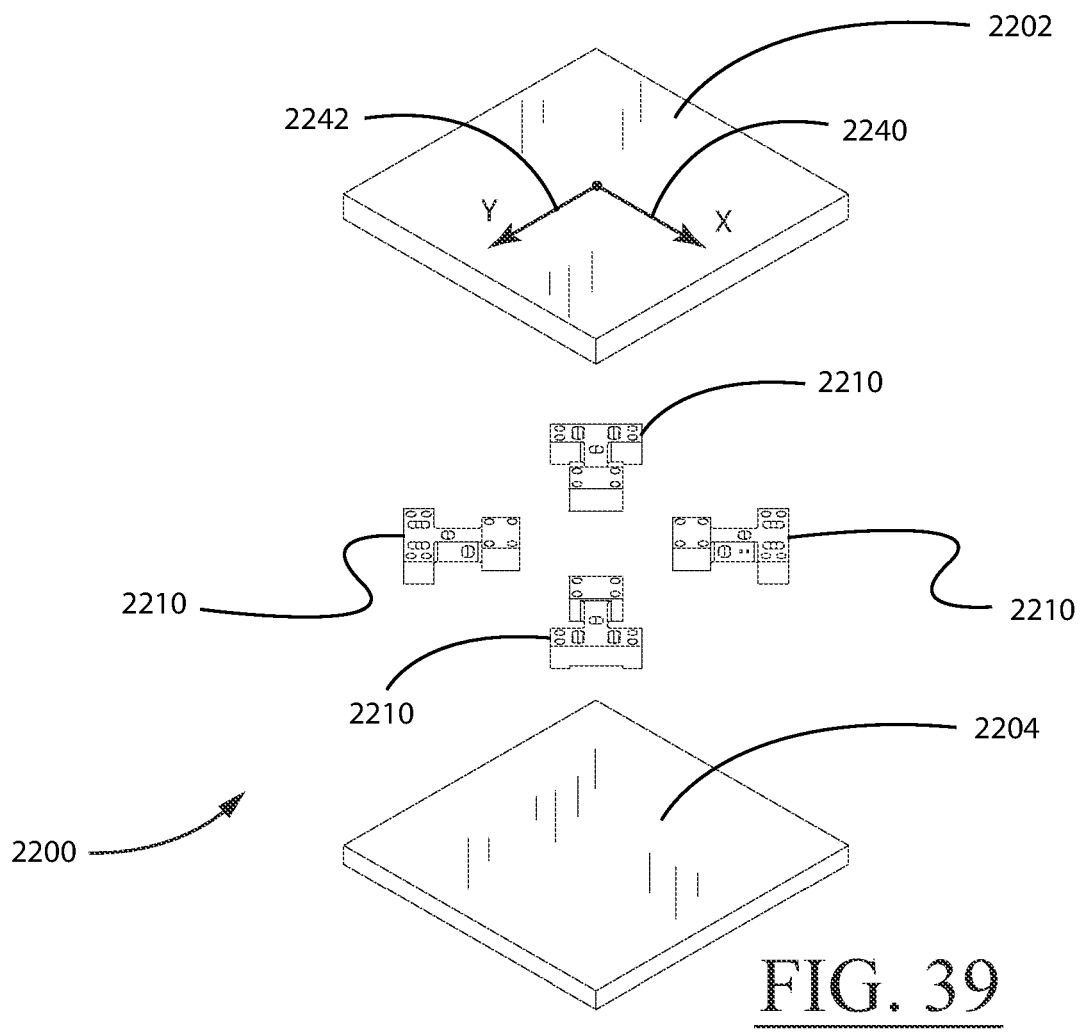
FIG. 39 is an exploded perspective view of the force measurement assembly of the force measurement system of FIG. 35.

In the illustrated embodiment, referring to FIG. 36, it can be seen that each of the plurality of load transducers 2210 of the force measurement assembly 2200 is diagonally arranged relative to the first coordinate axis direction (e.g., a direction of x-axis 2240) of the first shear output force ($F_X$) and a second coordinate axis direction (e.g., a direction of y-axis 2242) of the second shear output force ($F_Y$) such that: (i) when a first shear force ($F_X$) in the first coordinate axis direction (e.g., a direction of x-axis 2240) is applied to the force measurement assembly 2200, a summation of the second output signals from the plurality of deformation sensing elements 2226 of the plurality of load transducers 2210 by the data acquisition/data processing device 2208 produces a first shear force output value (i.e., $F_X$ value) above a measurement threshold (e.g., above 1.0 Newtons) in the first coordinate axis direction (e.g., a direction of x-axis 2240), but generally cancels out in the second coordinate axis direction (e.g., a direction of y-axis 2242); and (ii) when a second shear force ($F_Y$) in the second coordinate axis direction (e.g., a direction of y-axis 2242) is applied to the force measurement assembly 2200, a summation of the second output signals from the plurality of deformation sensing elements 2226 of the plurality of load transducers 2210 by the data acquisition/data processing device 2208 produces a second shear force output value ($F_Y$) above a measurement threshold (e.g., above 1.0 Newtons) in the second coordinate axis direction (e.g., a direction of y-axis 2242), but generally cancels out in the first coordinate axis direction (e.g., a direction of x-axis 2240). That is, in the illustrated embodiment, the first transducer beam sections 2212 of the load transducers 2210 are oriented at respective acute or obtuse angles relative to the force measurement assembly axes 2240, 2242 such that: (i) when the $F_X$ force is applied to the force measurement assembly 2200, a summation of the four (4) shear gages 2226 will show a large value in the $F_X$ direction, but cancel out in the $F_Y$ direction; and (ii) when the $F_Y$ force is applied to the force measurement assembly 2200, a summation of the four (4) shear gages 2226 will show a large value in the $F_Y$ direction, but cancel out in the $F_X$ direction. As a result, the $F_X/F_Y$ forces advantageously are able to be measured with only four (4) strain gages 2226 as opposed to a total of eight (8) strain gages (i.e., four (4) gages in the $F_X$ direction and four (4) gages in the $F_Y$ direction).

Now, the acquisition and processing of the load data carried out by the exemplary force measurement system of FIGS. 35 and 36 will be described. Initially, a load is applied to the force measurement assembly 2200 (e.g., by a subject disposed thereon). The load is transmitted from the top plate component 2202 to the plurality of load transducers 2210 disposed underneath the top plate component 2202. As described above, in the illustrated embodiment, the load transducers 2210 include a plurality of strain gages 2224, 2226 wired in one or more Wheatstone bridge configurations, wherein the electrical resistance of each strain gage is altered when the associated first transducer beam section 2212 of the load transducer 2210 undergoes deformation resulting from the load (i.e., forces and/or moments) acting on the plate component 2202. For each plurality of strain gages 2224, 2226 disposed on the load transducers 2210, the change in the electrical resistance of the strain gages brings about a consequential change in the output voltage of the Wheatstone bridge (i.e., a quantity representative of the load being applied to the measurement surface). Thus, in one embodiment, the four (4) load transducers 2210 disposed under the plate component 2202 output a total of eight (8) analog output voltages (signals). In some embodiments, the eight (8) analog output voltages from load transducers 2210 disposed under the plate component 2202 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 2200 transmits the force plate output signals $S_{FP01}$-$S_{FP08}$ to a main signal amplifier/converter. Depending on whether the preamplifier board also includes an analog-to-digital (A/D) converter, the force plate output signals $S_{FP01}$-$S_{FP08}$ could be either in the form of analog signals or digital signals. The main signal amplifier/converter further magnifies the force plate output signals $S_{FP01}$-$S_{FP08}$, and if the signals $S_{FP01}$-$S_{FP8}$ are of the analog-type (for a case where the preamplifier board did not include an analog-to-digital (A/D) converter), it may also convert the analog signals to digital signals. Then, the signal amplifier/converter may transform the digital signals into output load values by multiplying the voltage signals $S_{AC01}$-$S_{AC8}$ by a calibration matrix. Alternatively, the signal amplifier/converter may transmit either the digital or analog signals $S_{AC01}$-$S_{AC8}$ to the data acquisition/data processing device 2208 (computer 2208) so that the forces and/or moments that are being applied to the measurement surface of the force measurement assembly 2200 can be transformed into the output load values. In addition to its other hardware components, the data acquisition/data processing device 2208 may further comprise an analog-to-digital (A/D) converter if the signals $S_{AC01}$-$S_{AC08}$ are in the form of analog signals. In such a case, the analog-to-digital converter will convert the analog signals into digital signals for processing by the microprocessor of the data acquisition/data processing device 2208.

When the data acquisition/data processing device 2208 receives the voltage signals $S_{AC01}$-$S_{AC08}$, it initially transforms the signals into output forces by multiplying the voltage signals $S_{AC01}$-$S_{AC08}$ by a calibration matrix. If the load transducers 2210 are also capable of determining applied moments, the data acquisition/data processing device 2208 may additionally transform the signals into output moments by multiplying the voltage signals by the calibration matrix. After which, the force exerted on the surface of the force measurement assembly 2200, and the center of pressure of the applied force (i.e., the x and y coordinates of the point of application of the force applied to the measurement surface) is determined by the data acquisition/data processing device 2208.

Any of the features or attributes of the above-described embodiments and variations can be used in combination with any of the other features and attributes of the above described embodiments and variations as desired. The terms "generally" and "substantially" are used, for example, to account for accepted manufacturing tolerances and variations in the art.

It is readily apparent that the embodiments of the force measurement assemblies 1800, 1820, 1840, 1900a-1900f, 2000, 2100, 2200 and the force measurement systems using the same offer numerous advantages and benefits. As one example, the force measurement assemblies 1800, 1820, 1840 utilize load transducer beams that are capable of being interchangeably used with a myriad of different force plate sizes so that load transducers that are specifically tailored for a particular force plate size are unnecessary. As another example, the force measurement system 2140 employs a load transducer beam configuration that is able to be more easily machined. As yet another example, the load transducers 2210 of the force measurement system 2200 employ a configuration that reduces an overall length of the load transducer, while minimizing the twisting of the load transducer so as to reduce the non-linearities in the force measurements. Also, because of the reduced transducer length, the load transducers 2210 advantageously result in a higher natural frequency of the force measurement assembly 2200. The aforedescribed T-shaped load transducers 2210 maintain symmetry and are significantly stiffer than conventional load transducers.

From the foregoing disclosure and detailed description of certain preferred embodiments, it is also apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

The invention claimed is:

1. A force measurement system, comprising:
a force measurement assembly including at least one load transducer, the at least one load transducer including:
a load transducer frame portion, the load transducer frame portion including a first transducer beam section and a second transducer beam section, the first transducer beam section being connected to a middle portion of the second transducer beam section, and the load transducer frame portion configured to receive a load that is applied to the at least one load transducer, the load transducer frame portion of the at least one load transducer being generally T-shaped with a stem portion and an arm portion, the first transducer beam section forming the stem portion of the T-shaped load transducer frame portion and the second transducer beam section forming the arm portion of the T-shaped load transducer frame portion; and one or more deformation sensing elements disposed on the load transducer frame portion, the one or more deformation sensing elements being disposed on the stem portion of the T-shaped load transducer frame portion, a first one of the one or more deformation sensing elements being sensitive to a first force component of the load and outputting a first output signal representative of the first force component of the load, and the arm portion of the T-shaped load transducer frame portion containing no deformation sensing elements; and a data processing device operatively coupled to the one or more deformation sensing elements of the at least one load transducer, the data processing device configured to receive the first output signals from the one or more deformation sensing elements of the at least one load transducer, and the data processing device further configured to determine a first output force from the first output signal.

2. The force measurement system according to claim 1, wherein the first transducer beam section of the load transducer frame portion is disposed generally perpendicular to the second transducer beam section.

3. The force measurement system according to claim 1, wherein the one or more deformation sensing elements of the at least one load transducer comprise one or more strain gages configured to measure a deformation of one or more portions of the first transducer beam section of the load transducer frame portion.

4. The force measurement system according to claim 3, wherein the first transducer beam section of the load transducer frame portion comprises at least one first aperture disposed therein, the first transducer beam section having an outer surface and an inner surface, the inner surface circumscribing the at least one first aperture, and the at least one load transducer comprises at least one of the one or more strain gages disposed on the outer surface of the first transducer beam section generally opposite to the inner surface of the at least one first aperture.

5. The force measurement system according to claim 4, wherein the second transducer beam section of the load transducer frame portion comprises at least one second aperture disposed therein, the at least one second aperture of the second transducer beam section enhancing a measurement sensitivity of the at least one load transducer.

6. The force measurement system according to claim 1, wherein the one or more deformation sensing elements of the at least one load transducer comprise a plurality of deformation sensing elements, a first one of the plurality of deformation sensing elements being sensitive to the first force component of the load and a second one of the plurality of deformation sensing elements being sensitive to a second force component of the load and/or a third force component of the load.

7. The force measurement system according to claim 6, wherein the first force component of the load comprises a vertical force, the second force component of the load comprises a first shear force in a first direction, and the third force component of the load comprises a second shear force in a second direction that is perpendicular to the first direction of the first shear force.

8. The force measurement system according to claim 1, wherein the at least one load transducer of the force measurement assembly includes a plurality of load transducers spaced apart from one another, and each of the plurality of load transducers includes:

a load transducer frame portion, the load transducer frame portion including a first transducer beam section and a second transducer beam section, the first transducer beam section being connected to a middle portion of the second transducer beam section, and the load transducer frame portion configured to receive a load that is applied to the load transducer; and a plurality of deformation sensing elements disposed on the load transducer frame portion, a first one of the plurality of deformation sensing elements being sensitive to the first force component of the load and outputting a first output signal representative of the first force component of the load, and a second one of the plurality of deformation sensing elements being sensitive to a second force component of the load and/or a third force component of the load and outputting a second output signal representative of the second force component of the load and/or the third force component of the load;

wherein the data processing device is operatively coupled to the plurality of deformation sensing elements of the plurality of load transducers, and the data processing device is configured to receive the first and second output signals from the plurality of deformation sensing elements of the plurality of load transducers, and the data processing device is further configured to determine a first output force from the first output signal and a second output force and/or a third output force from the second output signal.

9. The force measurement system according to claim 8, wherein the first output force comprises a vertical output force, the second output force comprises a first shear output force in a first coordinate axis direction, and the third output force comprises a second shear output force in a second coordinate axis direction that is perpendicular to the first coordinate axis direction of the first shear output force.

10. The force measurement system according to claim 9, wherein each of the plurality of load transducers of the force measurement assembly is diagonally arranged relative to the first coordinate axis direction of the first shear output force and the second coordinate axis direction of the second shear output force such that:

when a first shear force in the first coordinate axis direction is applied to the force measurement assembly, a summation of the second output signals from the plurality of deformation sensing elements of the plurality of load transducers by the data processing device produces a first shear force output value above a measurement threshold in the first coordinate axis direction, but generally cancels out in the second coordinate axis direction; and when a second shear force in the second coordinate axis direction is applied to the force measurement assembly, a summation of the second output signals from the plurality of deformation sensing elements of the plurality of load transducers by the data processing device produces a second shear force output value above a measurement threshold in the second coordinate axis direction, but generally cancels out in the first coordinate axis direction.

11. The force measurement system according to claim 9, wherein the force measurement assembly further comprises a top component configured to receive at least one portion of a body of a user, the top component being supported by the plurality of load transducers; and wherein the first shear output force in the first coordinate axis direction comprises a shear force in a lateral direction of the user, and the second shear output force in the second coordinate axis direction comprises a shear force in a fore/aft direction of the user.

12. The force measurement system according to claim 8, wherein the force measurement assembly further comprises a top component and a base component, the top component configured to receive at least one portion of a body of a user, the top component being supported on the plurality of load transducers, and the base component being disposed underneath the plurality of load transducers.

13. The force measurement system according to claim 12, wherein the top component is in a form of a top plate with the top surface for receiving the at least one portion of the body of the user.

14. The force measurement system according to claim 12, wherein the base component is in a form of a bottom plate configured to be disposed on a support surface.

15. A force measurement system, comprising:
a force measurement assembly including a plurality of load transducers spaced apart from one another, each of the plurality of load transducers including:
 a load transducer frame portion, the load transducer frame portion including a first transducer beam section and a second transducer beam section, the first transducer beam section being connected to a middle portion of the second transducer beam section, and the load transducer frame portion configured to receive a load that is applied to the load transducer; and
 a plurality of deformation sensing elements disposed on the load transducer frame portion, a first one of the plurality of deformation sensing elements being sensitive to a first force component of the load and outputting a first output signal representative of the first force component of the load, and a second one of the plurality of deformation sensing elements being sensitive to a second force component of the load and/or a third force component of the load and outputting a second output signal representative of the second force component of the load and/or the third force component of the load; and
a data processing device operatively coupled to the plurality of deformation sensing elements of the plurality of load transducers, the data processing device configured to receive the first and second output signals from the plurality of deformation sensing elements of the plurality of load transducers, and the data processing device further configured to determine a first output force from the first output signal and a second output force and/or a third output force from the second output signal;
wherein the first output force comprises a vertical output force, the second output force comprises a first shear output force in a first coordinate axis direction, and the third output force comprises a second shear output force in a second coordinate axis direction that is perpendicular to the first coordinate axis direction of the first shear output force;

wherein each of the plurality of load transducers of the force measurement assembly is diagonally arranged relative to the first coordinate axis direction of the first shear output force and the second coordinate axis direction of the second shear output force such that:

when a first shear force in the first coordinate axis direction is applied to the force measurement assembly, a summation of the second output signals from the plurality of deformation sensing elements of the plurality of load transducers by the data processing device produces a first shear force output value above a measurement threshold in the first coordinate axis direction, but generally cancels out in the second coordinate axis direction; and when a second shear force in the second coordinate axis direction is applied to the force measurement assembly, a summation of the second output signals from the plurality of deformation sensing elements of the plurality of load transducers by the data processing device produces a second shear force output value above a measurement threshold in the second coordinate axis direction, but generally cancels out in the first coordinate axis direction.

16. The force measurement system according to claim 15, wherein the force measurement assembly further comprises a top component configured to receive at least one portion of a body of a user, the top component being supported by the plurality of load transducers; and
wherein the first shear output force in the first coordinate axis direction comprises a shear force in a lateral direction of the user, and the second shear output force in the second coordinate axis direction comprises a shear force in a fore/aft direction of the user.

17. The force measurement system according to claim 15, wherein the force measurement assembly further comprises a top component and a base component, the top component configured to receive at least one portion of a body of a user, the top component being supported on the plurality of load transducers, and the base component being disposed underneath the plurality of load transducers.

18. The force measurement system according to claim 15, wherein the load transducer frame portion of at least one of the plurality of load transducers is generally T-shaped with a stem portion and an arm portion; and
wherein the first transducer beam section forms the stem portion of the T-shaped load transducer frame portion and the second transducer beam section forms the arm portion of the T-shaped load transducer frame portion.

19. The force measurement system according to claim 18, wherein some of the plurality of deformation sensing elements are disposed on the stem portion of the T-shaped load transducer frame portion, and the arm portion of the T-shaped load transducer frame portion contains no deformation sensing elements.

20. The force measurement system according to claim 19, wherein the some of the plurality of deformation sensing elements of the at least one of the plurality of load transducers comprise one or more strain gages configured to measure a deformation of one or more portions of the stem portion of the T-shaped load transducer frame portion.

* * * * *